US009222096B2

(12) United States Patent
Spangenberg et al.

(10) Patent No.: US 9,222,096 B2
(45) Date of Patent: Dec. 29, 2015

(54) FUNGI AND PRODUCTS THEREOF

(75) Inventors: German Carlos Spangenberg, Bundoora (AU); Timothy Ivor Sawbridge, Coburg (AU); Simone Jane Rochfort, Reservoir (AU); Scott W. Mattner, Thornbury (AU); Ross C. Mann, Wendouree (AU)

(73) Assignee: Agriculture Victoria Services PTY LTD, Attwood, Victoria (AU)

( * ) Notice: Subject to any disclaimer, the term of this patent is extended or adjusted under 35 U.S.C. 154(b) by 0 days.

(21) Appl. No.: 14/119,247

(22) PCT Filed: May 22, 2012

(86) PCT No.: PCT/AU2012/000574
§ 371 (c)(1),
(2), (4) Date: Nov. 21, 2013

(87) PCT Pub. No.: WO2012/159161
PCT Pub. Date: Nov. 29, 2012

(65) Prior Publication Data
US 2014/0082771 A1 Mar. 20, 2014

(30) Foreign Application Priority Data
May 23, 2011 (AU) ................................ 2011901995

(51) Int. Cl.
C12N 9/88 (2006.01)
C12N 15/80 (2006.01)
A01H 15/00 (2006.01)
A01H 17/00 (2006.01)
A01N 63/04 (2006.01)
C12N 1/14 (2006.01)
C12P 5/00 (2006.01)
C12R 1/645 (2006.01)

(52) U.S. Cl.
CPC ............... *C12N 15/80* (2013.01); *A01H 15/00* (2013.01); *A01H 17/00* (2013.01); *A01N 63/04* (2013.01); *C12N 1/14* (2013.01); *C12N 9/88* (2013.01); *C12P 5/007* (2013.01); *C12R 1/645* (2013.01)

(58) Field of Classification Search
None
See application file for complete search history.

(56) References Cited

U.S. PATENT DOCUMENTS

2011/0097769 A1* 4/2011 Del Cardayre et al. ....... 435/134
2011/0182862 A1* 7/2011 Green et al. ................. 424/93.5

FOREIGN PATENT DOCUMENTS

WO 2009058943 A1 5/2009
WO 2010115156 A2 10/2010
WO 2011146634 A1 11/2011

OTHER PUBLICATIONS

International Preliminary Report on Patentability for PCT/AU2012/000574, Nov. 26, 2013.
Tomsheck, A.R. et al., *Hypoxylon* sp., an Endophyte of Persea indica, Producing 1,8-Cineole and Other Bioactive Volatiles with Fuel Potential, Microbial Ecology, 2010, pp. 903-914, vol. 60.
Strobel, G. et al., Endophyte Strain NRRL 50072 producing volatile organics is a species of *Ascocoryne*, Mycology, 2010, pp. 187-194, vol. 1, No. 3.
Cane, D. E. et al., Aristolochene synthase: purification, molecular cloning, high-level expression in *Escherichia coli*, and characterization of the Aspergillus terreus cyclase, Archives of Biochemistry and Biophysics, 2000, pp. 354-364.
Van Den Berg, M.A. et al., Genome sequencing and analysis of the filamentous fungus Penicullium chrysogenum, Nature Biotechnology, 2008, pp. 1161-1168, vol. 26, No. 10.
Edgar, R.C., Muscle: multiple sequence alignment with high accuracy and high throughput, Nucleic Acids Research, 2004, pp. 1792-1797, vol. 32, No. 5.
Felsenstein, J., Confidence limits on phylogenies: An approach using the bootstrap, Evolution, 1985, pp. 783-7941, vol. 39, No. 4.
Kimura, M., A simple method for estimating evolutionary rates of base substitutions through comparative studies of nucleotide sequences, Journal of Molecular Evolution, 1980, pp. 111-120, vol. 16.
Marchler-Bauer, A. et al., CDD: specific functional annotation with the Conserved Domain Database, Nucleic Acids Research, 2009, pp. D205-D210, vol. 37.
Pruitt, K.D., et al., NCBI reference sequences (RefSeq): a curated non-redundant sequence database of genomes, transcripts and proteins, Nucleic Acids Research, 2007, pp. D61-D65, vol. 35.
Saitou, N. et al, The Neighbor-joining Method: A New Method for Reconstructing Phylogenetic Trees, Molecular Biology and Evolution, 1987, pp. 406-425, vol. 4, No. 4.
Stanke, M. et al., AUGUSTUS: ab initio prediction of alternative transcripts, Nucleic Acids Research, 2006, pp. W435-W439, vol. 34.
Tamura, K., et al., MEGA4: Molecular Evolutionary Genetics Analysis (MEGA) software version 4.0, Molecular Biology and Evolution, 2007, pp. 1596-1599, vol. 24, No. 8.
Van Zijll De Jong, E. et al.. Development and characterization of EST-derived simple sequence repeat (SSR) markers for pasture grass endophytes, Genome, 2003, pp. 277-290, vol. 46.

(Continued)

*Primary Examiner* — Anne Gussow
*Assistant Examiner* — Mindy G Brown
(74) *Attorney, Agent, or Firm* — Larson & Anderson, LLC

(57) ABSTRACT

The present invention provides substantially purified or isolated fungi of *Nodulisporium* spp. or *Ascocoryne* spp., plants infected with said fungi, organic compounds produced by said fungi, and related nucleic acids, polypeptides and methods.

17 Claims, 29 Drawing Sheets

(56) References Cited

OTHER PUBLICATIONS

White, T.J., et al., Amplification and direct sequencing of fungal ribosomal RNA genes for phylogenetics, 1990. pp. 315-322, In M. A. Innis, D.H. Gelfand, J. J. Sninsky, and T. J. White (ed.) PCR protocols: a guide to methods and applications, Academic Press, Inc., New York, N.Y.

* cited by examiner

```
Query   15   WAPLIHPLSERVTREVDSYFLQHWPFPDEKSRKKFVAAGFSR TCF FPKALNDRIHFAC   74
             +  ++P +    E   + L+    P EK+ K+F++A F        +P A ++R+  A
Sbjct    4   FPYRLNPYVKEAQDEYLEWVLEEMLIPSEKAEKRFLSADFGD AAL YPDADDERLMLAA   63

Query   75   R  t                YM--SLEDGKAYNEKLIPISRGDVL--PDRSVPVEYITVDLWESMR   130
                                   S EDG+A  +L+ I RGD L   PD + P+E+    DLW
Sbjct   64   DL AW  VF    L  RDQKSPEDGEAGVTRLLDILRGDGLDSPDDATPLEFGLADLWRRTL   123

Query  131   AHDRV-MADDILEPVFTFQRAQTD  SV  EAM--DLGK LEY EKDV ALLGA MR S   185
             A       +       + A              D+  +LE    ++       E
Sbjct  124   ARMSAEWFNRFAHYTEDYFDAVIWEGKN LNGHVPDVAE LEM RFNI DPCLQ SE I   183

Query  186   MGLVVPPE--DLAIARQIDFNCARHLSVL            LASKNAHEEGGVLCSAVSILA   243
               G  VP      + R ++    +  +++                 + G +++ V +LA
Sbjct  184   GGPEVPAAVRLDPVMRALEALASDAIAL        +-----IKANGEVHNLVKVLA      236

Query  244   EQVGISIDGAKRILYYLCREWEHRHETLVKEMLQVRD----TPALRSYVKGLEYQMIGNE   299
             E+ G+S++  A  ++   E   + E L   +++  D      +PA+R+YV+GL   + GN
Sbjct  237   EEHGLSLEEAISVVRDMHNERITQFEELEASLIKSGDLEEESPAVRAYVEGLHNWISGNL   296

Query  300    SR   305
              RT+
Sbjct  297   D HRTS  302
```

Query = g9560 Contig 4951
Subject = Conserved Domain Database (NCBI)

FIGURE 12

```
  1 MSVAVETRTA PTVTLSTSKP LIKETWKIPA SGWTPMIHPR AEEVSREVDN YFLEHWNFPD
 61 DGAKSTFLKA GFSRVTCLYF PLAKDDRIHF ACRLLTVLFL IDDILEEMSF ADGEALNNRL
121 IELSKGPEYA TPDRSIPAEY VIYDLWESMR KHDLELANEV LEPTFVFMRS QTDRVRLSIK
181 ELGEYLRYRE KDVGKALLSA LMRYSMELRP TAEELAALKP LEENCSKHIS IVNDIYSFEK
241 EVIAAKTGHE EGSFLCSAVK VVATETTLGI SATKRVLWSM VREWELVHDA MCEALLAAAG
301 TSSQTVKDYM RGLQYQMSGN ELWSCTTPRY IEAIDQAAR
```

FIGURE 13

```
  1 MSTNNQADIQ ALLAKCVGQK VKIPDLFALC PWDVEITPWN AKLEKEIEQW RSRWIIDPVS
 61 LKRNRIVDPG LFARAGAPRA SFDGQLIVAL WAAWTFYWDD AHDFGEFDDK PEEVVAHCAQ
121 TIELFRQSLY NENPLAIDPA KISPDYLTVQ SVHEWAAVVG EKCVSPSLKD WLFKVFADTC
181 IGISRVQHEF ESKTILDLDT YQKIRRDSSG SLTTLACILY ADNVAFPDWF FDHELVLKAA
241 DLTDIIIWVV NDITSARHEL QCKHIDNYVP LLVYHKGLIP QEAVDEAGRV AHQAYLDFEA
301 LEPQLFQLGD SRGCAHEMGK FIDSCKFECS GIINWHYEVK RYVPWKPGMD RDSLYVVLGE
361 DLPTE
```

FIGURE 14

```
  1 MQGTRVAHFG ASWWPYASFE TLFIATCLSL WLFIWDDETD SLEFSDLSND FERSCMFRRE
 61 TMAYIEHSLK SDDSEILSQI SGNPIITNFK EVGEAIRSSC NEEQTATFLH ALDFFVKMCE
121 EEQHLQLSQG LPTIDQYIKR RMGSSGVEVC LAIQEYCFGM TIPSEYMQCE PMKTIWHETN
181 LIIATMNDMM SIKKEVDNSQ VDTLVPLLFV QLGSVQEAID KVAEMTRSAV QRFEDAERDI
241 KTLYASNPEL LSDLTKFIDG CKHACTGNMT WSLTSGRYKL STPDSDGFIR IKL
```

FIGURE 15

```
  1 MSLPIPTEGN ALRDAPFSGV TEKERDYVTE TGLAGWQDTQ DARNAYQWIL TEENCESSDV
 61 RSSEDSVLEN NAETLASLGE HLRDDSEAKL GTSSNPTSIR VQQTTTMALS KDQKTSSRVL
121 VAYLRYTALA YQTIHTPLTG VLEQVAEVGA DAIPRHQHLP TKFNMPLDIR PTTCAFDPVG
181 ISFSSDTAKQ ESFEFLREAI SQTIPGLENC NVFDPRSVGV PWPTSLPGAA QSKYWRDCEE
241 AVEDLMNAIV GAKPGEQGSL PAEMASVGLK AAKRKELFDT SVTAPMNMFP AANGPRARIM
301 GKANLLIFMH DDVIESETVE IPTIIDSALA DTVGDVKGAD ILWKNTIFKE YAEETIKVDP
361 VVGPVFLKGI LNWVQHTRDK LPGSMTFNSL NEYIDYRIGD FAVDFCDAAT MLTCEIFLTP
421 ADMEPLRKLH RLYMTHFSLT NDLYSYNKEL WAFEQNGSAL VNAVRVLELL LDTSPRGAKV
481 ILRAFLWDLE LQVNEELTKL SQSNLTPAQW RFARGMVEVL AGNTYYSATC LRYAKPGLRG
541 V
```

FIGURE 16

```
  1 MAPDIDQIWP STLDVPASAI DERKALVNRA LNQKILVPNI LSLMPAWISE LQPDIDEINK
 61 EIDEWLLIVN VAGAKKAKHR ARGNYTFLTA VYYPHCKKDK MLTLSKFLYW IFFWDDEIDN
121 GGELTEDEEG TQQCCDETNK CIDDCLGPNP NYTPPFNSRG TVEMFYPILR DLRAGLGPIS
181 TERLRLELHD YVNGVGRQQK VRQGDRLPDP WYHFQIRSDD VGVIPSITQN EYAMEFELPE
241 HVRRHEAMEF IVLECTKLTI LLNDVLSLQK EPRVSQLENL VLLFMNKYDL TLQAAIDKIL
301 DLIREHYAIC VAAEERLPWS KDDEKLNKDI REYVRGCQRL ATGTAYWSYS CERYFKQTQL
361 NDKWEVLLDL SYE
```

FIGURE 17

```
  1 MNFSFKITLK KPTFSGLQSF FPRHKPSISQ SSSSSTSSTS SIKLETTSTP QCITTFPVYV
 61 HRDEAQISQG ALDARSNFQH LLPDAEYRPH SAGPHGNFFA ICWPDSKMER AKLATEIIET
121 LWLYDDVIED IPHTGALEAH ASVRDSLVGK PEKTQSKGRI ATLFKTFGER VSQMDKDGAP
181 RVIGSLKSYL DNYDSQKTFF STIAEYTEFR IVNVGFGIME SFMQWTLGIH LDEDETELSR
241 DYYSSCGRVM GLTNDLYSWK VERIEPGDRQ WNAVPIIMKQ YNIREKDATV FLRGLIMYHE
301 QETRRLGLEL LRKTGESPKM IQYVGAMGLM LGGNCYWSST CPRYNPEP
```

FIGURE 18

```
  1 MSLASSFGDY PSSHWAPLIH PLSERVTREV DSYFLQHWPF PDEKSRKKFV AAGFSRVTCF
 61 YFPKALNDRI HFACRLLTVL FLIDDLLEYM SLEDGKAYNE KLIPISRGDV LPDRSVPVEY
121 ITYDLWESMR AHDRVMADDI LEPVFTFQRA QTDSVRLEAM DLGKYLEYRE KDVGKALLGA
181 LMRFSMGLVV PPEDLAIARQ IDFNCARHLS VLNDIWSFEK ELLASKNAHE EGGVLCSAVS
241 ILAEQVGISI DGAKRILYYL CREWEHRHET LVKEMLQVRD TPALRSYVKG LEYQMIGNEA
301 WSRTTLRYLA
```

FIGURE 19

```
  1 MARPKRITIT LLSLARRTQS KISSILFPSP LPAEGSSGAV VQYAPEKKPG AQQGLCGEAL
 61 VLASQLDGQT FRLPDLWKVL ADWPLAANPH AERLEGLVNS ILERHITSEK KLRALKQANF
121 ARLISLWYPD AEWPELEAAT AYSVWIFVWD DEVDAGDTDV SLDEELSRAY YKKSLSTIHR
181 LLGLDDAGGD DQGGSEEEET LHPNMVLFGD AARSLRSSTD KIQRERFYRE MENFMIQVGV
241 EHSHRMRGSI PTVDKYMEIR SGSVGCAPQI AITDFMLKIR LPESIMESAA MKALWRETVV
301 ICLILNDVYS VQKEIAQGSL LNLVFVIFKN CIPEKQNLDT VTADVEVALQ GSIRGFEDAA
361 ASLGQMVADD AQLDKDVQSF IRWCRYFITG VQQWSIESAR YGMAECLQED GSLSIVL
```

FIGURE 20

```
  1 ATGTCTGTCG CAGTAGAAAC CCGCACGGCC CCCACCGTTA CTCTAAGCAC TTCTAAGCCC
 61 CTTATCAAGG AGACTTGGAA GATCCCCGCC TCTGGCTGGA CGCCCATGAT CCACCCTAGA
121 GCTGAGGAGG TCTCTCGTGA GGTAGACAAC TACTTCCTCG AGCACTGGAA CTTCCCCGAC
181 GACGGCGCCA AATCTACTTT CCTCAAGGCG GGCTTCTCTC GTGTTACTTG CCTTTACTTC
241 CCTCTAGCCA AGGATGACAG AATACACTTT GCCTGCCGTC TCCTTACCGT CCTGTTCTTG
301 ATTGATGATA TTCTCGAGGA GATGTCCTTC GCTGATGGCG AGGCCCTCAA CAACAGACTG
361 ATTGAACTCT CCAAGGGTCC CGAGTATGCC ACCCCTGACC GGTCCATCCC GGCCGAGTAT
421 GTCATCTACG ACCTGTGGGA GAGCATGCGC AAGCACGATC TCGAGCTCGC CAATGAGGTT
481 CTCGAGCCCA CCTTTGTCTT CATGCGCTCG CAAACCGACC GTGTCCGACT GAGCATCAAG
541 GAGCTCGGCG AGTACCTGCG ATATCGTGAG AAGGATGTCG GCAAGGCTCT TCTATCAGCC
601 CTCATGCGCT ACTCCATGGA ATTGCGCCCC ACGGCGGAAG AGCTGGCAGC GCTCAAGCCC
661 CTAGAAGAGA ACTGCTCCAA GCACATCTCC ATCGTCAACG ACATCTACAG CTTCGAGAAG
721 GAAGTGATCG CGGCCAAGAC GGGCCACGAG GAGGGATCCT TCCTATGCTC TGCCGTCAAG
781 GTCGTCGCGA CGGAGACGAC GCTAGGCATC TCAGCCACCA ACGCGTGCT GTGGTCCATG
841 GTGCGCGAGT GGGAGCTCGT CCACGACGCC ATGTGCGAGG CCCTCCTCGC CGCCGCCGGC
901 ACCAGCAGCC AGACCGTCAA GGACTACATG CGCGGCCTGC AGTACCAGAT GAGCGGAAAC
961 GAGCTGTGGA GCTGCACGAC CCCGCGCTAC ATCGAGGCTA TCGACCAGGC CGCCCGA
```

FIGURE 21

```
   1 ATGTCTACAA ATAACCAAGC CGACATCCAG GCACTTCTCG CCAAGTGTGT AGGCCAAAAG
  61 GTCAAGATTC CGGATCTCTT CGCCCTGTGT CCGTGGGATG TGGAGATAAC CCCTTGGAAT
 121 GCAAAGCTGG AGAAGGAAAT AGAGCAGTGG CGATCGAGAT GGATTATAGA CCCGGTAAGC
 181 CTCAAGCGTA ACCGTATCGT CGATCCGGGT CTATTCGCGA GAGCCGGTGC TCCGAGGGCT
 241 TCTTTTGATG GCCAGTTGAT TGTTGCTTTG TGGGCTGCTT GGACCTTCTA CTGGGACGAT
 301 GCTCACGATT TCGGCGAATT TGACGACAAG CCCGAGGAAG TAGTCGCTCA TTGCGCACAG
 361 ACAATTGAGC TCTTCCGCCA GAGTCTGTAC AATGAGAACC CATTGGCTAT CGACCCCGCC
 421 AAGATCTCTC CCGACTACCT TACCGTCCAG TCAGTCCACG AGTGGGCAGC AGTGGTGGGA
 481 GAAAAGTGTG TTTCGCCCTC CTTGAAGGAC TGGCTCTTCA AGGTCTTCGC AGACACTTGT
 541 ATAGGGATTT CCCGAGTCCA ACACGAGTTC GAGAGTAAAA CGATACTAGA TCTTGATACG
 601 TATCAGAAGA TACGCAGGGA CTCGAGCGGT TCATTGACCA CTCTGGCATG CATTCTATAC
 661 GCCGATAATG TTGCTTTCCC AGATTGGTTC TTCGACCACG AACTCGTTCT AAAAGCCGCG
 721 GATCTAACTG ATATCATTAT CTGGGTTGTC AACGATATTA CGTCTGCACG ACACGAACTC
 781 CAATGCAAGC ACATCGACAA CTACGTACCG CTCCTAGTCT ACCACAAGGG TCTTACGCCG
 841 CAAGAAGCCG TCGATGAGGC AGGCAGGGTT GCGCACCAAG CCTACCTAGA CTTCGAGGCG
 901 CTGGAACCGC AACTCTTTCA GCTTGGGGAC AGCCGCGGCT GCGCTCACGA GATGGGGAAG
 961 TTTATCGATA GTTGTAAATT TGAGTGTTCG GGTATTATTA ACTGGCACTA CGAGGTTAAG
1021 CGCTATGTTC CTTGGAAGCC TGGTATGGAT CGTGATAGCC TGTATGTTGT GTTGGGTGAA
1081 GATCTACCAA CTGAG
```

FIGURE 22

```
  1 ATGCAAGGTA CCAGGGTAGC CCATTTTGGT GCTTCTTGGT GGCCCTACGC ATCGTTCGAG
 61 ACACTGTTCA TTGCGACGTG CCTTTCACTT TGGCTCTTCA TCTGGACGA CGAAACTGAC
121 TCACTCGAAT TCTCCGACCT CAGTAACGAC TTTGAACGAT CATGCATGTT TAGAAGAGAG
181 ACAATGGCAT ACATAGAGCA CAGTCTTAAA TCTGATGACT CTGAGATACT CTCTCAGATA
241 TCAGGCAACC CCATCATTAC TAACTTCAAA GAGGTTGCGG AAGCAATCAG ATCGTCATGC
301 AATGAAGAAC AGACCGCCAC CTTCTTACAC GCTTTGGATT TCTTCGTGAA AATGTGTGAG
361 GAGGAGCAGC ACCTGCAGCT AAGCCAAGGG CTACCGACAA TCGACCAATA TATTAAGCGC
421 CGAATGGGAT CTAGTGGGGT GGAAGTTTGC CTGGCCATTC AGGAATACTG CTTCGGCATG
481 ACAATTCCGA GTGAATACAT GCAATGCGAG CCGATGAAGA CGATTGGCA TGAGACCAAC
541 CTAATAATTG CTACAATGAA CGATATGATG TCTATCAAGA AGAGGTTGA TAATTCACAA
601 GTTGATACTC TGGTCCCACT GCTCTTCGTC CAGCTTGGTT CGGTCCAGGA GGCCATTGAC
661 AAGGTTGCAG AGATGACAAG ATCTGCTGTC CAGCGCTTTG AGGACGCTGA GAGAGACATA
721 AAGACACTTT ATGCTTCCAA TCCAGAACTC CTAAGTGACC TCACCAAATT CATCGATGGG
781 TGTAAGCATG CCTGTACGGG AAACATGACT TGGAGCTTGA CTTCCGGTCG GTACAAGCTA
841 AGTACCCCAG ATTCTGATGG CTTCATCAGG ATAAAATTA
```

FIGURE 23

```
   1 ATGTCGTTGC CGATACCGAC AGAAGGAAAC GCTCTAAGGG ACGCGCCATT TTCGGGTGTC
  61 ACCGAGAAGG AGAGAGATTA TGTAACCGAG ACAGGGCTTG CAGGCTGGCA GGATACGCAA
 121 GATGCGAGAA ATGCGTATCA GTGGATCCTC ACGGAAGAAA ACTGCGAGTC TAGTGACGTG
 181 AGGTCAAGCG AGGACTCTGT GCTGGAAAAT AACGCCGAAA CTTTGGCGAG CTTGGGTGAA
 241 CATCTTCGCG ATGATTCCGA GGCTAAGCTA GGTACGTCTT CGAACCCCAC GTCCATTCGT
 301 GTCCAGCAAA CAACCACGAT GGCTTTGTCT AAGGACCAAA AGACCAGTAG CAGGGTCCTA
 361 GTAGCATACC TGCGTTACAC TGCTTTAGCC TACCAGACTA TACATACGCC GCTGACGGGC
 421 GTTCTCGAAC AAGTTGCCGA AGTAGGTGCA GACGCAATAC CTAGACATCA ACACCTTCCA
 481 ACAAAGTTCA ACATGCCACT AGATATCCGA CCCACAACCT GCGCGTTCGA TCCCGTTGGG
 541 ATCTCATTCA GCTCAGACAC TGCCAAGCAA GAGAGCTTCG AGTTCCTAAG AGAGGCCATC
 601 TCTCAGACCA TACCAGGACT CGAGAACTGC AATGTCTTCG ATCCGCGCTC TGTGGGAGTA
 661 CCATGGCCAA CCTCGCTGCC GGGCGCAGCC CAGAGCAAGT ATTGGAGAGA CTGCGAAGAA
 721 GCAGTAGAAG ATCTGATGAA CGCAATCGTC GGCGCGAAGC CAGGCGAGCA GGGCTCCCTG
 781 CCAGCAGAGA TGGCCAGTGT AGGCTTGAAG GCAGCGAAAC GAAAGGAACT CTTCGATACA
 841 TCTGTCACCG CCCCGATGAA CATGTTTCCC GCAGCGAACG GTCCACGAGC GAGGATAATG
 901 GGTAAAGCAA ACTTGCTTAT CTTTATGCAT GATGATGTTA TTGAATCCGA GACGGTCGAG
 961 ATACCAACCA TAATTGACTC CGCCCTCGCC GACACAGTTG GCGACGTCAA AGGTGCAGAT
1021 ATACTCTGGA AGAACACCAT CTTCAAAGAA TATGCGGAGG AGACCATCAA GGTAGACCCT
1081 GTTGTCGGAC CGGTCTTCTT GAAAGGCATA CTGAACTGGG TACAACACAC GCGTGACAAG
1141 CTGCCCGGCT CTATGACATT CAATTCTCTA AATGAATACA TCGATTACCG AATCGGGGAT
1201 TTCGCTGTCG ACTTCTGCGA CGCAGCCATC ATGTTGACAT GTGAAATCTT TCTAACACCG
1261 GCCGACATGG AGCCTCTCAG GAAGCTTCAC AGACTTTACA TGACTCACTT CTCGTTGACG
1321 AACGACCTCT ATTCTTATAA CAAAGAACTC TGGGCCTTTG AGCAAAACGG CTCTGCGCTC
1381 GTGAACGCCG TCCGAGTTCT GGAGCTGCTC CTGGACACCT CCCCTCGAGG AGCGAAGGTT
1441 ATCCTTCGAG CTTTCCTGTG GGACCTCGAG CTCCAGGTCA ATGAAGAACT CACAAAACTC
1501 TCCCAGAGCA ACCTAACACC AGCCCAGTGG CGCTTCGCAC GGGGCATGGT CGAGGTGCTT
1561 GCGGGAAACA CATACTACTC CGCGACTTGT CTACGATACG CGAAGCCGGG ATTGCGAGGA
1621 GTC
```

FIGURE 24

```
   1 ATGGCACCCG ACATAGATCA GATCTGGCCA TCTACATTGG ATGTGCCAGC CAGCGCCATC
  61 GATGAACGCA AAGCCCTGGT TAATAGAGCG TTGAACCAAA AGATTCTAGT CCCGAACATC
 121 CTGTCTTTAA TGCCAGCATG GATCAGCGAG TTGCAACCGG ACATTGATGA AATCAATAAG
 181 GAAATAGACG AGTGGCTTCT AATCGTCAAT GTGGCCGGGG CTAAGAAAGC GAAACATCGA
 241 GCTCGTGGAA ATTACACATT TCTTACGGCT GTTTACTATC CTCATTGTAA GAAGGATAAG
 301 ATGCTTACCC TGTCGAAGTT TCTTTACTGG ATATTCTTCT GGGATGATGA AATCGACAAC
 361 GGTGGAGAAC TGACCGAGGA CGAGGAGGGC ACACAACAAT GCTGTGATGA GACAAACAAA
 421 TGCATTCACG ACTGTCTCGG GCCTAACCCC AACTACACGC CCCCTCCAAA CTCGCGAGGG
 481 ACAGTCGAGA TGTTCTACCC GATTCTACGA GATCTTCGAG CAGGCCTCGG CCCAATCTCA
 541 ACAGAACGGC TTCGTCTCGA GCTCCACGAC TACGTGAACG GAGTAGGAAG ACAGCAGAAG
 601 GTTCGCCAAG GAGATCGCCT GCCGGATCCG TGGTATCACT TCCAGATTCG ATCTGACGAT
 661 GTCGGTGTCA TCCCCAGTAT CACACAGAAT GAATACGCCA TGGAATTCGA GCTCCCGGAG
 721 CATGTCCGCA GACATGAGGC CATGGAGTTC ATTGTTCTGG AGTGCACTAA ACTCACCATC
 781 CTCCTTAACG ACGTGCTCTC TCTACAAAAA GAATTTCGCG TGTCTCAGCT TGAGAACCTT
 841 GTCCTTCTTT TCATGAACAA GTACGATCTC ACCCTTCAAG CAGCCATCGA TAAGATCCTA
 901 GATCTCATCC GCGAGCACTA TGCAATCTGT GTTGCGGCCG AGGAGAGGCT TCCTTGGAGC
 961 AAAGACGACG AGAAGCTGAA CAAGGATATC AGAGAATATG TTCGTGGCTG CCAGAGGCTG
1021 GCTACTGGCA CTGCTTACTG GAGTTACTCG TGCGAGCGGT ATTTTAAGCA AACGCAACTA
1081 AATGATAAAT GGGAGGTCCT TCTGGATCTA TCCTATGAA
```

FIGURE 25

```
   1 ATGAACTTCA GCTTCAAAAT TACTCTCAAG AAGCCGACAT TCAGCGGACT TCAAAGCTTC
  61 TTTCCTAGAC ACAAGCCTTC AATAAGCCAG TCTTCATCAT CTTCAACTTC TTCAACCTCT
 121 TCAATCAAGC TTGAGACCAC GTCAACGCCT CAATGCATTA CAACATTCCC TGTTTACGTT
 181 CACCGAGACG AAGCTCAAAT TTCCCAAGGT GCCTTGGACG CTCGGAGCAA CTTTCAACAC
 241 CTCCTTCCAG ATGCTGAATA TCGACCTCAT TCAGCCGGGC CACATGGCAA TTTCTTTGCC
 301 ATCTGTTGGC CAGACAGCAA AATGGAAAGG GCAAAACTAG CCACTGAAAT CATCGAGACG
 361 TTGTGGCTAT ATGATGACGT TATCGAGGAT ATACCACACA CGGGGGCCTT GGAAGCACAC
 421 GCCAGCGTCC GCGACTCATT GGTAGGAAAG CCCGAGAAAA CACAGTCCAA GGGTCGGATT
 481 GCTACCCTTT TCAAAACCTT CGGTGAGCGC GTGAGTCAGA TGGACAAAGA CGGGGCGCCG
 541 CGTGTCATTG GCTCTCTTAA GTCGTACCTT GACAATTACG ACAGCCAAAA GACCCCATTC
 601 TCCACGATTG CGGAATATAC AGAGTTTAGA ATAGTAAACG TTGGATTTGG GATTATGGAA
 661 AGTTTTATGC AGTGGACCCT TGGTATCCAT CTGGATGAAG ATGAGACAGA GCTGTCTCGG
 721 GACTATTACT CCTCCTGTGG GCGAGTTATG GGGTTGACCA ACGACTTGTA TTCATGGAAG
 781 GTCGAGCGGA TAGAACCTGG TGATCGACAA TGGAATGCCG TGCCAATCAT CATGAAGCAG
 841 TACAACATAC GCGAGAAGGA TGCTACAGTA TTCCTCAGAG GGTTGATTAT GTACCATGAA
 901 CAAGAGACAC GCCGACTTGG TCTAGAGCTT TTAAGGAAAA CCGGGGAATC GCCGAAGATG
 961 ATCCAGTATG TGGGCGCGAT GGGACTGATG CTGGGTGGAA ATTGTTACTG GAGCTCGACT
1021 TGCCCGCGCT ACAATCCGGA GCCG
```

FIGURE 26

```
  1 ATGTCTTTGG CATCGTCGTT TGGGGATTAT CCCAGCTCGC ACTGGGCGCC ACTGATACAC
 61 CCCCTTTCTG AGAGGGTCAC GCGGGAAGTC GACAGCTACT TCCTGCAGCA TTGGCCTTTC
121 CCCGATGAGA AATCGAGGAA GAAATTCGTC GCAGCTGGGT TCTCGCGTGT AACGTGCTTC
181 TACTTCCCTA AGCTCTCAA CGACCGAATT CATTTTGCTT GTCGACTACT TACAGTCCTG
241 TTTCTCATCG ATGACCTCCT TGAGTACATG TCTTTGGAAG ATGGGAAAGC ATATAATGAA
301 AAGCTCATCC CTATTTCCCG CGGTGACGTA CTGCCGGATC GATCAGTCCC CGTGGAATAC
361 ATCACGTATG ACTTATGGGA AAGCATGAGA GCACATGACC GCGTTATGGC AGATGACATA
421 CTCGAGCCCG TATTCACATT CCAGAGGGCA CAAACTGACT CCGTGCGCCT GGAGGCCATG
481 GACCTAGGAA AATATCTCGA ATATCGAGAG AAAGATGTTG GCAAGGCACT ACTTGGAGCC
541 TTGATGAGAT CTCCATGGG CCTTGTCGTG CCTCCAGAGG ACCTCGCTAT TGCAAGGCAG
601 ATTGATTTTA ACTGTGCAAG GCACCTTTCA GTTCTGAATG ACATATGGAG CTTTGAAAAA
661 GAGCTGCTGG CATCCAAGAA TGCACACGAA GAAGGTGGTG TGTTGTGCTC GGCCGTATCT
721 ATCTTAGCTG AGCAGGTCGG AATATCAATT GATGGAGCAA AACGTATACT ATACTACCTC
781 TGTCGTGAAT GGGAGCATCG ACACGACACG CTAGTTAAGG AGATGCTCCA GGTCCAGAC
841 ACACCAGCCT TAAGATCATA TGTCAAGGGG CTTGAGTACC AGATGATCGG GAACGAGGCG
901 TGGAGCAGGA CTACACTGAG GTATCTGGCC CCAACAGAT
```

FIGURE 27

```
   1 ATGGCGAGGC CCAAGCGAAT CACCACGACA CTGCTGAGTC TCGCGCGGCG GACGCAGTCA
  61 AAGATATCAT CTATCCTATT CCCGTCCCCC CTGCCCGCGG AAGGGAGCTC AGGCGCCGTC
 121 GTCCAATACG CTCCCGAGAA GAAGCCCGGC GCACAGCAGG GTCTCTGCGG TGAGGCGTTG
 181 GTCTTAGCTT CTCAGCTCGA CGGGCAAACA TTCCGCCTCC CAGACCTGTG GAAGGTCTTA
 241 GCAGACTGGC CTCTGGCCGC CAACCCGCAC GCGGAGCGGC TCGAGGGTCT CGTCAACAGC
 301 ATACTAGAGC GCCACATCAC CAGCGAGAAG AAGCTCAGGG CTCTAAAACA GGCTAACTTT
 361 GCCCGTCTCA TCTCCCTCTG GTATCCCGAC GCAGAATGGC CCGAGCTGGA GGCGGCAACA
 421 GCCTACTCTG TGTGGATCTT CGTGTGGGAC GACGAAGTCG ACGCCGGTGA TACTGACGTG
 481 TCTCTCGACG AGGAGCTCTC GAGAGCCTAT TACAAGAAAT CTCTCAGCAC GATCCACCGC
 541 CTCTTAGGTT TAGATGATGC TGGCGGAGAT GACCAGGGGG GCTCCGAGGA GGAGGAGACA
 601 TTGCATCCCA ACATGGTCCT GTTTGGCGAT GCAGCACGCA GCCTGCGCAG CTCAACAGAC
 661 AAGATCCAGC GGGAGCGATT CTACCGCGAG ATGGAGAACT TCATGATCCA AGTGGGTGTA
 721 GAGCACAGTC ACCGCATGCG CGGCTCCATC CCCACCGTGG ACAAATACAT GGAGATACGC
 781 TCCGGGTCTG TTGGTTGTGC GCCCCAGATC GCCATCACCG ATTTTATGCT AAAGATCCGA
 841 CTCCCCGAGT CCATCATGGA ATCTGCGGCC ATGAAAGCGC TCTGGAGAGA GACGGTTGTA
 901 ATATGTCTTA TTCTTAACGA TGTTTACTCT GTTCAGAAAG AAATAGCGCA AGGGTCATTG
 961 TTAAACCTAG TCCCAGTAAT ATTCAAGAAC TGCATTCCTG AAAAGCAGAA CCTCGATACG
1021 GTAACGGCGG ATGTCGAGGT AGCGCTGCAG GGAAGCATAA GGGGTTTCGA GGACGCAGCG
1081 GCGTCCCTCG GTCAGATGGT GGCTGATGAC GCGCAACTAG ACAAGGATGT CCAGTCTTTC
1141 ATTAGATGGT GCCGCTACTT CATCACCGGG GTCCAGCAAT GGAGTATAGA ATCGGCTCGG
1201 TACGGCATGG CGGAGTGTTT GCAAGAGGAT GGCTCGCTCA GCATAGTGCT G
```

FUNGI AND PRODUCTS THEREOF

FIELD OF THE INVENTION

The present invention relates to fungi, plants infected with fungi, products produced by fungi, and related nucleic acids, polypeptides and methods.

BACKGROUND OF THE INVENTION

Microbes represent an invaluable source of novel genes and compounds that have the potential to be utilised in a range of industrial sectors. Scientific literature gives numerous accounts of microbes being the primary source of antibiotics, immunosuppressants, anticancer agents and cholesterol-lowering drugs, in addition to their use in environmental decontamination and in the production of food and cosmetics. A relatively unexplored group of microbes known as endophytes, which reside in the tissues of living plants, offer a particularly diverse source of novel compounds and genes that may provide important benefits to society, and in particular, agriculture.

Endophytes often form mutualistic relationships with their hosts, with the endophyte conferring increased fitness to the host, often through the production of defence compounds. At the same time, the host plant offers the benefits of a protected environment and nutriment to the endophyte.

Recent discoveries highlight the diversity of applications of endophytes such as in the agricultural (e.g. bioprotectants) and energy (e.g. biofuels) sectors. For instance, the fungus *Muscodor albus* from *Cinnamomum zeylanicum* in Honduras produces a suite of volatile antimicrobial compounds that are effective against soil borne pathogens, and this has enabled development of a commercial preparation which has been utilised as a biological alternative (e.g. mycofumigant) to the ozone depleting fumigant methyl bromide. Furthermore, the discovery of the endophytic fungus *Gliocladium roseum*, which produces a variety of hydrocarbons commonly found in diesel, petrol and biodiesel, offers mankind a potential alternative to fossil fuels.

Bioprotectant endophytes that have been developed and commercialised include *Neotyphodium* species that produce insecticidal alkaloids, including peramine (a pyrrolopyrazine) and the lolines (pyrrolizidines). These compounds can accumulate to high levels in planta where they act as potent feeding deterrents against a range of insect pests, including a major pest of graminaceous species, *Listronotus bonariensis* (Argentine stem weevil). The gene responsible for peramine biosynthesis is a non-ribosomal peptide synthase (NRPS) and has been identified as perA.

The insecticidal compounds, destruxins, have also been well characterised as secondary metabolites of fungi. Their mode of action is still unclear however it is widely recognised that they induce cytological changes to the target organism, in particular $Ca^{2+}$ dependent processes. It is thought that a NRPS is also responsible for the production of this compound. Another antimicrobial compound of fungi that is regulated by NRPS is the peptaibols. *Trichoderma virens* possesses a 62.8 kb NRPS gene (tex1) that codes for a 20,925 amino acid NRPS regulating the production of its peptaibol. Similarly, an endophyte of *Quercus suber*, *Trichoderma citrinoviridae*, produces another peptaibol that shows antifungal activity against a range of plant pathogens, including *Biscogniauxia mediterranea* and *Apiognomonia quercine*.

In recent years molecular breeding of endophytes has also been employed to overcome pathogen and pest infections. The xylem limited bacterium *Clavibacter xyli* subsp *cynodontis* (Cxc) was inserted with the gene encoding the insectidal protein from *Bacillus thuringiensis* subsp *kurstaki*, the Bt-toxin. Similarly, Cxc was also engineered to encode β-1,3-glucanase which degrades an essential structural component of cell walls of fungal phytopathogens, β-1,3-glucan.

It is estimated that there are up to 1 million endophytic organisms which may possess genes and compounds that offer enormous benefits to agriculture, particularly in the area of disease management. As such, there exists a need to isolate and identify these endophytes, and characterise the compounds and genes responsible for the bioprotectant activity.

It is an objection of the present application to overcome, or at least alleviate, one or more of the difficulties or deficiencies associates with the prior art.

SUMMARY OF THE INVENTION

This patent application documents bioprotectant fungi of *Nodulisporium* spp. and *Ascocoryne* spp. that may exhibit broad spectrum activity against important plant pathogenic organisms. Antibiotic compounds responsible for the activity are characterised, along with the genes that regulate their production.

In a first aspect, the present invention provides a substantially purified or isolated fungus of *Nodulisporium* spp. or *Ascocoryne* spp. Preferably, the fungus is selected from the group consisting of Dandenong Ranges isolate 1 and Yarra Ranges isolates 7, 10, 11, 12, 13 and 15 and Otway Ranges isolates 1, 3, 4 and 5.

Representative samples, namely Dandenong Ranges isolate 1, Yarra Ranges isolate 11 and Otway Ranges isolate 4, were deposited at The National Measurement Institute on 3 May 2011 with accession number V11/011039 (Dandenong Ranges 1) and 17 Feb. 2010 with accession numbers V10/000244 (Yarra Ranges isolate 11) and V10/000245 (Otway Ranges isolate 4).

Preferably, the fungus is of a species selected from the group consisting of *Nodulisporium* sp. (asexual stage), *Ascocoryne sarcoides* (sexual stage) and *Coryne* sp. (asexual stage).

By 'substantially purified' is meant that the fungus is free of other organisms. The term therefore includes, for example, a fungus in axenic culture. Preferably, the fungus is at least approximately 90% pure, more preferably at least approximately 95% pure, even more preferably at least approximately 98% pure.

The term 'isolated' means that the fungus is removed from its original environment (e.g. the natural environment if it is naturally occurring). For example, a naturally occurring fungus present in a living plant is not isolated, but the same fungus separated from some or all of the coexisting materials in the natural system, is isolated.

In its natural environment, the fungus may be an endophyte, i.e. live mutualistically within a plant. Alternatively, the fungus may be an epiphyte, i.e. grow attached to or upon a plant.

The fungus of the present invention may in its natural environment be associated with a plant of the genus *Lomatia*, *Nothofagus* or *Picea*, more particularly *Lomatia fraseri* or *Nothofagus cunninghamii*.

By 'associated with' in this context is meant that the fungus lives on, in or in close proximity to the plant. For example, it may be endophytic, for example living within the internal tissues of the plant, or epiphytic, for example growing externally on the plant.

The fungus may be a heterotroph that uses organic carbon for growth, more particularly a saprotroph that obtains nutrients by consuming detritus.

In a further aspect, the present invention provides a plant inoculated with a fungus as hereinbefore described, said plant comprising a fungus-free host plant stably infected with said fungus.

Preferably, the plant is an agricultural plant, including horticultural crops such as potato, tomato, broccoli and apple, grains and pulses such as wheat, barley, beans, peas and lentils, and pasture grasses and legumes such as ryegrass, fescue, clover and lucerne.

Preferably, the plant is infected with the fungus by a method selected from the group consisting of inoculation, breeding, crossing, hybridization and combinations thereof.

The fungus-infected plants may be cultured by known techniques. The person skilled in the art can readily determine appropriate culture conditions depending on the plant to be cultured.

In a further aspect, the present invention provides a method of culturing a fungus as hereinbefore described, said method including growing said fungus on a medium including a source of carbohydrates, for example a starch/sugar-based agar or broth such as potato dextrose agar or potato dextrose broth, or a cereal-based agar or broth such as oatmeal agar or oatmeal broth.

The fungus may be cultured under aerobic or anaerobic conditions.

In a particularly preferred embodiment, the fungus may be cultured in a culture medium including potato dextrose or oatmeal, for example potato dextrose agar, oatmeal agar, potato dextrose broth or oatmeal broth.

The fungus may be cultured for a period of approximately 1 to approximately 100 days, more preferably from approximately 1 to approximately 50 days more preferably from approximately 10 to approximately 25 days.

In a preferred embodiment, the fungus may be cultured in a bioreactor. By a 'bioreactor' is meant a device or system that supports a biologically active environment, such as a vessel in which is carried out a chemical process involving fungi of the present invention and/or products thereof. The chemical process may be aerobic or anaerobic. The bioreactor may have a volume ranging in size from milliliters to cubic meters, for example from approximately 50 ml to approximately 50,000 liters. The bioreactor may be operated via batch culture, batch feed culture, perfusion culture or continuous culture, for example continuous culture in a stirred-tank bioreactor. Fungi cultured in the bioreactor may be suspended or immobilized.

In a preferred embodiment, the method may include the further step of recovering an organic compound produced by the fungus from within fungal cells, including intracellular tissues (e.g. terpenes), from the culture medium (e.g. secreted liquids) or from the air space (e.g. secreted vapours) associated with the culture medium or fungus.

Vapours may arise directly from the fungus or from the secreted liquids which transition between vapour and liquid phases.

The step of recovering the organic compound is preferably done by separating cells from the culture medium or capturing vapours associated with the culture medium or fungus.

Preferably the organic compound is then isolated or purified by a method selected from the group consisting of gas chromatography, liquid chromatography, fractional distillation and absorption chromatography, such as pressure swing adsorption.

By an 'organic compound' is meant a chemical compound whose molecules contain carbon.

In a preferred embodiment, the organic compound may be a hydrocarbon such as a volatile hydrocarbon or a liquid hydrocarbon.

By a 'hydrocarbon' is meant an organic compound comprising the elements carbon and hydrogen.

In another preferred embodiment, the organic compound may be a terpene, more preferably a monoterpene or a sesquiterpene.

By a 'terpene' is meant a molecule formed from units of isoprene and having a molecular formula $(C_5H_8)_n$ where n is the number of linked isoprene units. The isoprene units may be linked together 'head to tail' to form linear chains or they may be arranged to form rings.

In a preferred embodiment, the organic compound may be selected from the group consisting of ($C_{10}H_{16}$, $C_{10}H_{14}$, $C_7H_{10}$, $C_9H_{12}$, $C_{10}H_{18}O$, $C_9H_{18}O_2$, $C_{10}H_{14}O$, $C_{15}H_{24}$), or a derivative and/or salt thereof.

In a particularly preferred embodiment, the organic compound may be selected from the group consisting of α-Thujene, β-Sabinene, β-Myrcene, α-Phellendrene, α-Terpinene, p-Cymene, (R)-(+)-Limonene, Eucalyptol, α-Ocimene, 1,4-Cyclohexadiene,1-methyl-, Cyclohexane,1,2,4-tris(methylene)-, β-Ocimene, γ-Terpinene, α-Terpinolene, Allo-Ocimene, (−)-Terpinen-4-ol, α-Terpineol, 2H-pyran,tetrahydro-2-(propan-2-ylidene)-5-methoxy, 2H-pyran,tetrahydro-2-isopropyl-5-methoxy, 3-Cyclohexene-1-acetaldehyde,4-methyl-α-methylene-, 1-Cyclohexene-1-carboxaldehyde,4-(1-methylethenyl)-, p-Mentha-1,4 (8)-dien-3-one (isomers), Bicyclo[2.2.2]octan-1-ol-ethyl, β-Elemene, α-Guajene, Bicyclo[5.3.0]decane,2 methylene-5-(1-methylvinyl)-8-methyl, δ-Guaijene, cyclohexane derivatives, cyclohexene derivatives and pyran derivatives.

By a 'derivative' is meant an organic compound obtained from, or regarded as derived from, a compound of the present invention. Examples of derivatives include compounds where the degree of saturation of one or more bonds has been changed (e.g., a single bond has been changed to a double or triple bond) or wherein one or more atoms are replaced with a different atom or functional group. Examples of different atoms and functional groups may include, but are not limited to hydrogen, halogen, oxygen, nitrogen, sulphur, hydroxy, alkoxy, alkyl, alkenyl, alkynyl, amine, amide, ketone and aldehyde.

Preferably, said organic compound is produced by a method as hereinbefore described.

In a preferred embodiment, derivatives of the organic compound of the present invention may be obtained by chemical dehydration (for example using a strong acid) and/or hydrogenation.

The organic compound of the present invention may also be converted to lower molecular weight alkanes and alkenes, for example by cracking (e.g., catalytic or thermal).

In a preferred embodiment, the organic compound may be obtained from a fungus of the present invention.

In a still further aspect of the present invention, there is provided use of an organic compound according to the present invention as a biofuel or biofuel precursor, in biofumigation or bioprotection, or in the cosmetic or pharmaceutical industry, for example as a surfactant.

In a further aspect of the present invention, there is provided a method of producing an organic compound, said method including culturing a fungus as hereinbefore described under conditions suitable to produce said organic compound. Preferably the conditions are as hereinbefore described.

Preferably the organic compound is a hydrocarbon or terpene, including a hydrocarbon or terpene as hereinbefore described.

In a preferred embodiment, the method may include the further step of recovering an organic compound produced by the fungus as hereinbefore described.

On the basis of the deposits referred to above, the entire genome of a fungus of *Nodulisporium* spp. or *Ascocoryne* spp., selected from the group consisting of Dandenong Ranges isolate 1 and Yarra Ranges isolates 7, 10, 11, 12, 13 and 15 and Otway Ranges isolates 1, 3, 4 and 5, is incorporated herein by reference.

In a preferred embodiment, the entire genomes of Dandenong Ranges isolate 1, Yarra Ranges isolate 11 and Otway Ranges isolate 4, which were deposited at The National Measurement Institute on 3 May 2010 and 17 Feb. 2010 with accession numbers V11/011039, V10/000244 and V10/000245, respectively, are incorporated herein by reference.

Thus, in a further aspect, the present invention includes identifying and/or cloning nucleic acids including genes encoding polypeptides that are involved in the production of organic compounds of the present invention, for example genes encoding enzymes from one or more biochemical pathways which result in the synthesis of said organic compounds.

By a 'biochemical pathway' is meant a plurality of chemical reactions occurring within a cell which are catalysed by more than one enzyme or enzyme subunit and result in the conversion of a substrate into a product. This includes, for example, a situation in which two or more enzyme subunits (each being a discrete protein coded by a separate gene) combine to form a processing unit that converts a substrate into a product. A 'biochemical pathway' is not constrained by temporal or spatial sequentiality.

Methods for identifying and/or cloning nucleic acids encoding such genes are known to those skilled in the art and include creating nucleic acid libraries, such as cDNA or genomic libraries, and screening such libraries, for example using probes, for genes encoding enzymes from synthetic pathways for said organic compounds; or mutating the genome of the fungus of the present invention, for example using chemical or transposon mutagenesis, identifying changes in the production of an organic compound of the present invention, and thus identifying genes encoding enzymes from synthetic pathways for said organic compound.

Thus, in a further aspect of the present invention, there is provided a substantially purified or isolated nucleic acid encoding a polypeptide involved in the production of an organic compound of the present invention.

In a preferred embodiment, the nucleic acid may encode a polypeptide involved in the production of a terpene, or a hydrocarbon such as a volatile hydrocarbon or a liquid hydrocarbon. Preferably, the organic compound is a terpene or hydrocarbon as hereinbefore described.

In a preferred embodiment, the nucleic acid may encode a polypeptide involved in the production of an organic compound. Preferably, the organic compound is a terpene, more preferably a monoterpene or a sesquiterpene. In a particularly preferred embodiment, the nucleic acid may encode a terpene synthase.

More preferably, the organic compound is selected from the group consisting of $C_{10}H_{16}$, $C_{10}H_{14}$, $C_7H_{10}$, $C_9H_{12}$, $C_{10}H_{18}O$, $C_9H_{18}O_2$, $C_{10}H_{14}O$, $C_{15}H_{24}$ and derivatives and salts thereof.

More preferably the organic compound is selected from the group consisting from the group consisting α-Thujene, β-Sabinene, β-Myrcene, α-Phellendrene, α-Terpinene, p-Cymene, (R)-(+)-Limonene, Eucalyptol, α-Ocimene, 1,4-Cyclohexadiene,1-methyl-, Cyclohexane, 1,2,4-tris(methylene)-, β-Ocimene, γ-Terpinene, α-Terpinolene, Allo-Ocimene, (−)-Terpinen-4-ol, α-Terpineol, 2H-pyran, tetrahydro-2-(propan-2-ylidene)-5-methoxy, 2H-pyran, tetrahydro-2-isopropyl-5-methoxy, 3-Cyclohexene-1-acetaldehyde,4-methyl-α-methylene-, 1-Cyclohexene-1-carboxaldehyde,4-(1-methylethenyl)-, p-Mentha-1,4(8)-dien-3-one (isomers), Bicyclo[2.2.2]octan-1-ol,4-ethyl, β-Elemene, α-Guajene, Bicyclo[5.3.0]decane,2 methylene-5-(1-methylvinyl)-8-methyl, δ-Guaijene, cyclohexane derivatives, cyclohexene derivatives and pyran derivatives.

In a particularly preferred embodiment, the nucleic acid may encode a polypeptide including an amino acid sequence selected from the group consisting of sequences shown in FIGS. 12 to 19 hereto and functionally active fragments and variants thereof.

In a particularly preferred embodiment, the nucleic acid may include a nucleotide sequence selected from the group consisting of shown in FIGS. 20 to 27 hereto and functionally active fragments and variants thereof.

By 'nucleic acid' is meant a chain of nucleotides capable of carrying genetic information. The term generally refers to genes or functionally active fragments or variants thereof and or other sequences in the genome of the organism that influence its phenotype. The term 'nucleic acid' includes DNA (such as cDNA or genomic DNA) and RNA (such as mRNA or microRNA) that is single- or double-stranded, optionally containing synthetic, non-natural or altered nucleotide bases, synthetic nucleic acids and combinations thereof.

By a 'nucleic acid encoding a polypeptide involved in the production of an organic compound of the present invention' is meant a nucleic acid encoding an enzyme normally present in a fungus of the present invention, which catalyses a step in the pathway that results in synthesis of the organic compound of the present invention.

The present invention encompasses functionally active fragments and variants of the nucleic acids of the present invention. By 'functionally active' in relation to the nucleic acid is meant that the fragment or variant (such as an analogue, derivative or mutant) is capable of manipulating synthesis of an organic compound of the present invention, for example by being translated into an enzyme that is able to participate in the pathway that results in synthesis of the organic compound. Such variants include naturally occurring allelic variants and non-naturally occurring variants. Additions, deletions, substitutions and derivatizations of one or more of the nucleotides are contemplated so long as the modifications do not result in loss of functional activity of the fragment or variant. Preferably the functionally active fragment or variant has at least approximately 80% identity to the relevant part of the above mentioned sequence to which the fragment or variant corresponds, more preferably at least approximately 90% identity, even more preferably at least approximately 95% identity, most preferably at least approximately 98% identity. Such functionally active variants and fragments include, for example, those having conservative nucleic acid changes.

Preferably the fragment has a size of at least 20 nucleotides, more preferably at least 50 nucleotides, more preferably at least 100 nucleotides, more preferably at least 200 nucleotides, more preferably at least 500 nucleotides.

By 'conservative nucleic acid changes' is meant nucleic acid substitutions that result in conservation of the amino acid in the encoded protein, due to the degeneracy of the genetic code. Such functionally active variants and fragments also include, for example, those having nucleic acid changes which result in conservative amino acid substitutions of one or more residues in the corresponding amino acid sequence.

By 'conservative amino acid substitutions' is meant the substitution of an amino acid by another one of the same class, the classes being as follows:

Nonpolar: Ala, Val, Leu, Ile, Pro, Met Phe, Trp
Uncharged polar: Gly, Ser, Thr, Cys, Tyr, Asn, Gln
Acidic: Asp, Glu
Basic: Lys, Arg, His Other conservative amino acid substitutions may also be made as follows:

Aromatic: Phe, Tyr, His
Proton Donor: Asn, Gln, Lys, Arg, His, Trp
Proton Acceptor: Glu, Asp, Thr, Ser, Tyr, Asn, Gln In a further aspect of the present invention, there is provided a genetic construct including a nucleic acid according to the present invention.

By 'genetic construct' is meant a recombinant nucleic acid molecule.

In a preferred embodiment, the genetic construct according to the present invention may be a vector.

By a 'vector' is meant a genetic construct used to transfer genetic material to a target cell.

The vector may be of any suitable type and may be viral or non-viral. The vector may be an expression vector. Such vectors include chromosomal, non-chromosomal and synthetic nucleic acid sequences, e.g. derivatives of plant viruses; bacterial plasmids; derivatives of the Ti plasmid from *Agrobacterium tumefaciens*; derivatives of the Ri plasmid from *Agrobacterium rhizogenes*; phage DNA; yeast artificial chromosomes; bacterial artificial chromosomes; binary bacterial artificial chromosomes; vectors derived from combinations of plasmids and phage DNA. However, any other vector may be used as long as it is replicable or integrative or viable in the target cell.

In a preferred embodiment of this aspect of the invention, the genetic construct may further include a promoter and a terminator; said promoter, gene and terminator being operatively linked.

By a 'promoter' is meant a nucleic acid sequence sufficient to direct transcription of an operatively linked nucleic acid sequence.

By 'operatively linked' is meant that the nucleic acid(s) and a regulatory sequence, such as a promoter, are linked in such a way as to permit expression of said nucleic acid under appropriate conditions, for example when appropriate molecules such as transcriptional activator proteins are bound to the regulatory sequence. Preferably an operatively linked promoter is upstream of the associated nucleic acid.

By 'upstream' is meant in the 3'→5' direction along the nucleic acid.

The promoter and terminator may be of any suitable type and may be endogenous to the target cell or may be exogenous, provided that they are functional in the target cell.

A variety of terminators which may be employed in the genetic constructs of the present invention are also well known to those skilled in the art. The terminator may be from the same gene as the promoter sequence or a different gene. Particularly suitable terminators are polyadenylation signals, such as the (CaMV) 35S polyA and other terminators from the nopaline synthase (nos) and the octopine synthase (ocs) genes.

The genetic construct, in addition to the promoter, the gene and the terminator, may include further elements necessary for expression of the nucleic acid, in different combinations, for example vector backbone, origin of replication (ori), multiple cloning sites, spacer sequences, enhancers, introns (such as the maize Ubiquitin Ubi intron), antibiotic resistance genes and other selectable marker genes [such as the neomycin phosphotransferase (nptll) gene, the hygromycin phosphotransferase (hph) gene, the phosphinothricin acetyltransferase (bar or pat) gene], and reporter genes (such as beta-glucuronidase (GUS) gene (gusA)]. The genetic construct may also contain a ribosome binding site for translation initiation. The genetic construct may also include appropriate sequences for amplifying expression.

Those skilled in the art will appreciate that the various components of the genetic construct are operably linked, so as to result in expression of said nucleic acid. Techniques for operably linking the components of the genetic construct of the present invention are well known to those skilled in the art. Such techniques include the use of linkers, such as synthetic linkers, for example including one or more restriction enzyme sites.

Preferably, the genetic construct is substantially purified or isolated. By 'substantially purified' is meant that the genetic construct is free of the genes, which, in the naturally-occurring genome of the organism from which the nucleic acid or promoter of the invention is derived, flank the nucleic acid or promoter. The term therefore includes, for example, a genetic construct which is incorporated into a vector; into an autonomously replicating plasmid or virus; or into the genomic DNA of a prokaryote or eukaryote; or which exists as a separate molecule (e.g. a cDNA or a genomic or cDNA fragment produced by PCR or restriction endonuclease digestion) independent of other sequences. It also includes a genetic construct which is part of a hybrid gene encoding additional polypeptide sequence. Preferably, the substantially purified genetic construct is at least approximately 90% pure, more preferably at least approximately 95% pure, even more preferably at least approximately 98% pure.

The term "isolated" means that the material is removed from its original environment (e.g. the natural environment if it is naturally occurring). For example, a naturally occurring nucleic acid present in a living plant is not isolated, but the same nucleic acid separated from some or all of the coexisting materials in the natural system, is isolated. Such nucleic acids could be part of a vector and/or such nucleic acids could be part of a composition, and still be isolated in that such a vector or composition is not part of its natural environment.

As an alternative to use of a selectable marker gene to provide a phenotypic trait for selection of transformed host cells, the presence of the genetic construct in transformed cells may be determined by other techniques well known in the art, such as PCR (polymerase chain reaction), Southern blot hybridisation analysis, histochemical assays (e.g. GUS assays), thin layer chromatography (TLC), northern and western blot hybridisation analyses.

The genetic constructs of the present invention may be introduced into plants or fungi by any suitable technique. Techniques for incorporating the genetic constructs of the present invention into plant cells or fungal cells (for example by transduction, transfection, transformation or gene targeting) are well known to those skilled in the art. Such techniques include *Agrobacterium*-mediated introduction, *Rhizobium*-mediated introduction, electroporation to tissues, cells and protoplasts, protoplast fusion, injection into reproductive organs, injection into immature embryos and high velocity projectile introduction to cells, tissues, calli, immature and mature embryos, biolistic transformation, Whiskers transformation, and combinations thereof. The choice of technique will depend largely on the type of plant or fungus to be transformed, and may be readily determined by an appropriately skilled person. For transformation of protoplasts, PEG-mediated transformation is particularly preferred. For transformation of fungi electroporation is particularly preferred.

Cells incorporating the genetic constructs of the present invention may be selected, as described below, and then cultured in an appropriate medium to regenerate transformed plants or fungi, using techniques well known in the art. The culture conditions, such as temperature, pH and the like, will be apparent to the person skilled in the art. The resulting plants may be reproduced, either sexually or asexually, using methods well known in the art, to produce successive generations of transformed plants or fungi.

Accordingly, in a further aspect of the present invention there is provided a transgenic plant cell, plant, plant seed or other plant part, or a transgenic fungus, fungal cell or other fungal part, capable of producing an organic compound as hereinbefore defined in greater quantities than an untransformed control plant cell, plant, plant seed or other plant part, or an untransformed fungus, fungal cell or other fungal part.

In a preferred embodiment the a transgenic plant cell, plant, plant seed or other plant part or the transgenic fungus, fungal cell or other fungal part has an increase in the quantity of the organic compound produced of at least approximately 10%, more preferably at least approximately 20%, more preferably at least approximately 30%, more preferably at least approximately 40% relative to the untransformed control.

For example, the quantity of the organic compound may be increased by between approximately 10% and 300%, more preferably between approximately 20% and 200%, more preferably between approximately 30% and 100%, more preferably between approximately 40% and 80% relative to the untransformed control.

Preferably the transgenic plant cell, plant, plant seed or other plant part or the transgenic fungus, fungal cell or other fungal part includes a nucleic acid, genetic construct or vector according to the present invention. Preferably the transgenic plant cell, plant, plant seed or other plant part, or the transgenic fungus, fungal cell or other fungal part, is produced by a method according to the present invention.

The present invention also provides a transgenic plant, plant seed or other plant part, or a transgenic fungus, fungal cell or other fungal part, derived from a plant or fungal cell of the present invention and including a nucleic acid, genetic construct or vector of the present invention.

The present invention also provides a transgenic plant, plant seed or other plant part, or a transgenic fungus, fungal cell or other fungal part, derived from a plant or fungus of the present invention and including a nucleic acid, genetic construct or vector of the present invention.

By 'plant cell' is meant any self-propagating cell bounded by a semi-permeable membrane and containing a plastid. Such a cell also requires a cell wall if further propagation is desired. Plant cell, as used herein includes, without limitation, algae, cyanobacteria, seeds suspension cultures, embryos, meristematic regions, callus tissue, leaves, roots, shoots, gametophytes, sporophytes, pollen and microspores.

By 'fungal cell' is meant any cell of a fungus. The term 'fungus' refers to whole fungi, fungal organs and tissues (e.g., asci, hyphae, pseudohyphae, rhizoid, sclerotia, sterigmata, spores, sporodochia, sporangia, synnemata, conidia, ascostroma, cleistothecia, mycelia, perithecia, basidia and the like), spores, fungal cells and the progeny thereof. Fungi may either exist as single cells or make up a multicellular body called a mycelium, which consists of filaments known as hyphae. Most fungal cells are multinucleate and have cell walls, composed chiefly of chitin.

Preferably, the fungus is of *Nodulisporium* spp. or *Ascocoryne* spp.

By 'transgenic' is meant any cell which includes a DNA sequence which is inserted by artifice into a cell and becomes part of the genome of the organism which develops from that cell.

The present invention also provides a substantially purified or isolated polypeptide involved in the production of an organic compound of the present invention.

In a preferred embodiment, the polypeptide may be involved in the production of a terpene, or a hydrocarbon such as a volatile hydrocarbon or a liquid hydrocarbon. Preferably, the organic compound is a terpene or hydrocarbon as hereinbefore described.

In a particularly preferred embodiment, the polypeptide may include an amino acid sequence selected from the group consisting of sequences shown in FIGS. 12 to 19 hereto and functionally active fragments and variants thereof. In a particularly preferred embodiment, the polypeptide may be a terpene synthase.

In a particularly preferred embodiment, the polypeptide may be encoded by a nucleic acid including a sequence selected from the group consisting of sequences shown in FIGS. 20 to 27 hereto and functionally active fragments and variants thereof. The present invention encompasses functionally active fragments and variants of the polypeptides of the present invention. By functionally active' in this context is meant that the fragment or variant has one or more of the biological properties of the corresponding protein from which the fragment or variant is derived. Additions, deletions, substitutions and derivatizations of one or more of the amino acids are contemplated so long as the modifications do not result in loss of functional activity of the fragment or variant. Preferably the fragment or variant has at least approximately 80% identity to the relevant part of the above mentioned sequence to which the fragment or variant corresponds, more preferably at least approximately 90% identity, more preferably at least approximately 95% identity, most preferably at least approximately 98% identity. Such functionally active variants and fragments include, for example, those having conservative amino acid substitutions of one or more residues in the corresponding amino acid sequence.

Preferably the fragment has a size of at least 10 amino acids, more preferably at least 20 amino acids, more preferably at least 50 amino acids, more preferably at least 100 amino acids, more preferably at least 200 amino acids. As used herein, except where the context requires otherwise, the term "comprise" and variations of the term, such as "comprising", "comprises" and "comprised", are not intended to exclude further additives, components, integers or steps.

In a further aspect of the present invention, there is provided use of an organic compound, nucleic acid, genetic construct, vector, polypeptide, fungus, transgenic plant cell, plant, plant seed or other plant part, or transgenic fungus, fungal cell or other fungal part, according to the present invention in biofumigation or bioprotection.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

DETAILED DESCRIPTION OF THE EMBODIMENTS

Eleven fungal isolates were collected from two plant species at cool temperate rainforests within the Dandenong Ranges, Yarra Ranges and the Otway Ranges (Victoria, Australia). One isolate was collected from foliar tissue of *Lomatia fraseri* in the Dandenong Ranges, while the other 10 isolates were collected from decaying wood of *Nothafagus cunninghamii* in the Yarra Ranges and Otway Ranges. All isolates were morphologically and genetically (5.8S-ITS rRNA gene) identified. The isolate from *L. fraserii* was identified as *Nodulisporium* sp. (teleomorph: *Hypoxylon* sp., Xylariaceae), while the 10 isolates from *N. cunninghamii* were identified as *Ascocoryne sarcoides* (anamorph: *Coryne* sp., Helotiaceae). Molecular markers based on single sequence repeats from expressed sequence tags (EST-SSR markers) detected genetic diversity amongst *A. sarcoides* isolates, separating them according to origin (i.e. either Yarra Ranges or Otway Ranges). All eleven isolates exhibited bioactivity in in vitro bioassays against a range of plant pathogenic fungi, including *Fusarium oxysporum, Sclerotinia minor* and *Pythium ultimum*. The in vitro bioassays indicated that the isolate of *Nodulisporium* produced volatile bioactive compounds, while isolates of *A. sarcoides* produced liquid bioactive compounds. GC/MS analysis of *Nodulisporium* identified 58 volatile organic compounds, including many monoterpenes (e.g. eucalyptol) and, sesquiterpenes (e.g. β-Elemene), which may be produced by plants as defence compounds (e.g. eucalyptol—eucalyptus oil). The genes regulating the production of the terpenes were identified following the sequencing of the genome of the *Nodulisporium* isolate. A total of 8 terpene synthases were identified that are thought to regulate the production of the mono- and sesquiterpene compounds in *Nodulisporium*.

The two fungi were morphologically characterised via micro- and macroscopic features of in vitro states and identified as *Nodulisporium* sp. and *A. sarcoides* (and in vivo state). The identification of the isolates were supported by comparing sequences of the rRNA gene (5.8S/ITS) to closely related *Ascocoryne* and *Nodulisporium* species from around the world (closest matches from Genbank). Isolates of *A. sarcoides* clustered together with a bootstrap support of 81.0%. Similarly, the isolate of *Nodulisporium* clustered closest to species of *Nodulisporium* and *Hypoxylon* (the teleomorph of *Nodulisporium*), with a bootstrap support of 80.0%.

Isolates of *A. sarcoides* were genotyped using EST-SSR markers derived from *Neotyphodium* species. Amplification was expected as markers were derived from expressed genes, some of which were likely to be universally found across the fungal kingdom. Isolates clustered according to origin.

In vitro bioassays were established to determine the bioactivity of *Nodulisporium* and *A. sarcoides* isolates against 3 plant pathogenic fungi, *F. oxysporum, S. minor* and *P. ultimum*. Both *Nodulisporium* and *A. sarcoides* reduced the growth of the plant pathogenic fungi by up to 100%. Bioassays indicated that volatile compounds were responsible for the bioactivity observed with *Nodulisporium*, whereas the bioactive compounds of *A. sarcoides* were liquid.

To evaluate the production of volatile compounds from *Nodulisporium*, growth conditions were chosen to enhance the production (diversity and quantity) of these compounds. For example, high nutrient media (e.g. potato dextrose agar) was used as the carbon source for growth. As a result a total of 58 compounds were produced by *Nodulisporium* including a range of terpenes, which are low molecular weight organic compounds that may be produced by plants as defence compounds. These terpenoid compounds included 21 monoterpenes (α-Thujene, β-Sabinene, β-Myrcene, α-Phellendrene, α-Terpinene, p-Cymene, (R)-(+)-Limonene, Eucalyptol, α-Ocimene, β-Ocimene, γ-Terpinene, α-Terpinolene, Allo-Ocimene, (−)-Terpinen-4-ol, α-Terpineol, 2H-pyran,tetrahydro-2-(propan-2-ylidene)-5-methoxy, 2H-pyran,tetrahydro-2-isopropyl-5-methoxy, 3-Cyclohexene-1-acetaldehyde,4-methyl-α-methylene-, 1-Cyclohexene-1-carboxaldehyde,4-(1-methylethenyl)-, p-Mentha-1,4(8)-dien-3-one (isomers), Bicyclo[2.2.2]octan-1-ol,4-ethyl,) and four sesquiterpenes (β-Elemene, α-Guajene, Bicyclo[5.3.0]decane,2 methylene-5-(1-methylvinyl)-8-methyl, δ-Guaijene). A further 16 monoterpene-like compounds and seven sesquiterpene-like compounds were produced by *Nodulisporium*. These terpenes had masses consistent with mono and sesquiterpenes, and were structurally similar based on their ion fragmentation (cyclohexane-, cyclohexene- and pyran-derivatives). A major constituent of the volatile metabolome of *Nodulisporium* was eucalyptol which is major component of eucalyptus oil, a potent antimicrobial extract found within leaves of *Eucalyptus* species. While the applicant does not wish to be restricted by theory, it is proposed that the volatile terpene compounds of *Nodulisporium* are acting synergistically to deliver the biocidal activity in in vitro bioassays.

The genome of the *Nodulisporium* isolate was sequenced in an effort to determine the genes responsible for the regulation of the bioactive terpenes. Mono- and sesqui-terpenes are produced via the mevalonate pathway through a series of condensation and phosphorylation reactions to yield prenyl pyrophosphate chains with 10 or 15 carbons. These products are then converted to monoterpenes (10 carbons) or sesquiterpenes (15 carbons) by a terpene synthase. Terpene synthases promote the metal (e.g. $Mg^{2+}$) ion-dependent expulsion of pyrophosphate and catalyse the formation of acyclic and cyclic terpenes from the prenyl groups via a common ionization reaction, followed by various reactions such as isomerisation, cyclization, rearrangement (hydride shifts, methyl shifts, alkyl shifts, Wagner-Meerwein shifts), hydration and deprotonation. The majority of sesquiterpene synthases have been functionally characterised from microbes, unlike monoterpene synthases that have predominantly been characterised from plants. The enormous diversity of terpenes can be attributed to the unique ability of terpene synthases to synthesise multiple products from the one enzyme. While some terpenes synthases produce a single product, a large majority of mono- and sesqui-terpene synthases catalyse the formation of multiple terpene structures, often with high regio- and stereo-selectivity. For instance, in *Arabidopsis thaliana*, the enzyme At-TPS-Cin was responsible for catalysing the formation of 10 acyclic (e.g. myrcene and (E)-β-ocimene) and cyclic (e.g. sabinene, α-pinene) monoterpenes, with eucalyptol predominating (52%). The genome of *Nodulisporium* contained 8 terpene synthases, as these genes possessed structural domains specific to terpene synthases, including aspartate rich regions that form the substrate binding site. It is proposed that these 8 terpene synthases regulate the production of the volatile bioactive mono- and sesquiterpenes of *Nodulisporium*.

*Nodulisporium* and *A. sarcoides* represent a highly valuable microbial resource, principally due to there unique metabolism and ability to produce organic bioactive compounds via novel genes. These organisms, metabolites and genes are of commercial interest in the agricultural sector, particularly in the area of plant protection.

DESCRIPTION OF THE FIGURES

FIG. 8 shows images of in vitro bioassays of *Ascocoryne* isolates from the Yarra Ranges (Victoria) against *S. minor* (including an untreated control).

Figure 1:
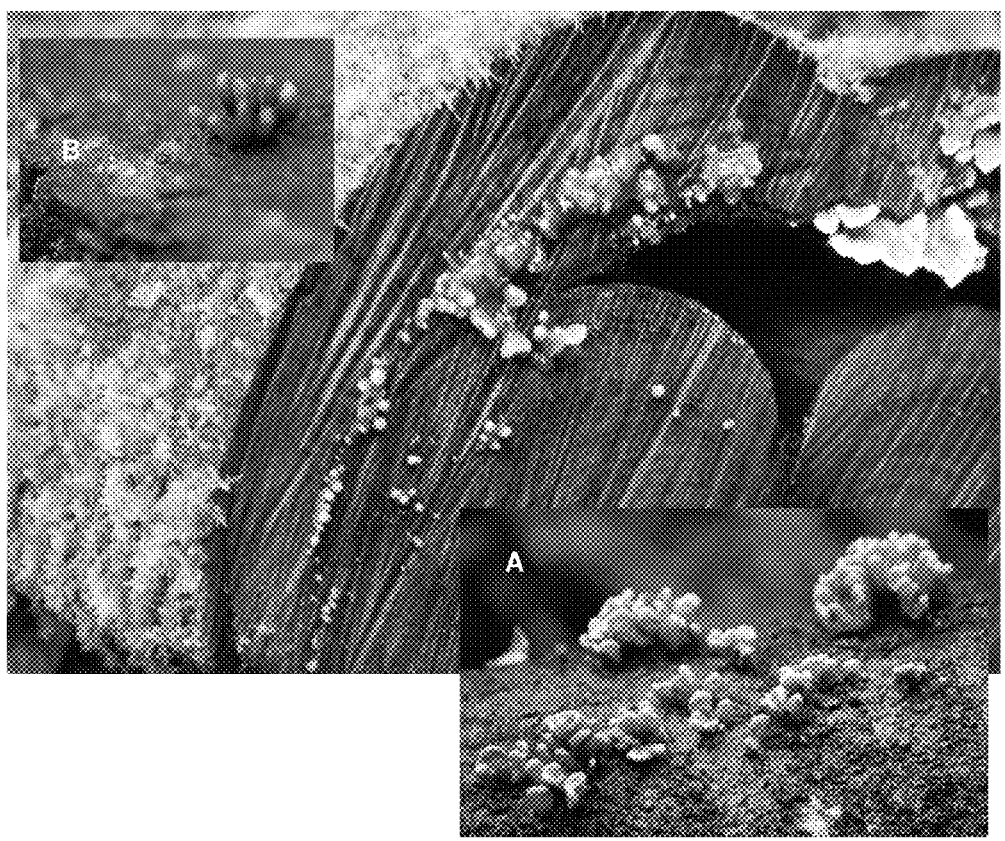
FIG. 1 shows apothecia (A) and conidiomata (B) of *Ascocoryne sarcoides* growing on fallen logs of *Nothafagus cunninghamii*.

1-Butanol, 3-methyl—(4.098 min)
1,4 Cyclohexadiene, 1-methyl (5.032 min)
α-Thujene (9.312 min)
β-Sabinene (10.868 min)
β-Myrcene (11.425 min)
α-Phellandrene (11.806 min)
p-Cymene (12.578 min)
(R)-(+)-Limonene (12.575 min)
Eucalyptol (12.825 min)
α-Ocimene (12.941 min)
Cyclohexane, 1,2,4-tris(methylene)—(13.075 min)
β-Ocimene (13.249 min)
γ-Terpinene (13.558 min)
α-Terpinolene (14.469 min)
Phenylethyl alcohol (14.469 min)
Allo-Ocimene (15.725 min)
Benzoic acid ethyl ester (16.972 min)
(−)-Terpinen-4-ol (17.159 min)
α-Terpineol (17.566 min)
2H-pyran, tetrahydro-2-(propan-2-ylidene)-5-methoxy (19.987 min)
2H-pyran, tetrahydro-2-isopropyl-5-methoxy (20.124 min)
3-Cyclohexene-1-acetaldehyde, 4-methyl-α-methylene— (20.506 min)
1-Cyclohexene-1-carboxaldehyde, 4-(1-methylethenyl)— (20.676 min)
p-Mentha-1,4(8)-dien-3-one (and isomer) (21.744/22.849 min)
Bicyclo[2.2.2]octan-1-ol4-ethyl (22.526 min)
β Elemene (23.129 min)
α-Guajene (24.297 min)
Bicyclo[5.3.0]decane,2 methylene-5-(1-methylvinyl)-8-methyl (25.580 min)
δ-Guaijene (25.998 min)

FIG. 11 shows a representative terpene synthase sequence from *Nodulisporium* (g9560, 313 amino acids; SEQ ID NO: 1), aligned against a "type" terpene synthase from the Conserved Domain Database (NCBI; SEQ ID NO: 2). The highlighted areas represent common domains associated with terpene synthases. The medium grey area identifies the aspartate rich regions that form the substrate binding site. The dark grey area identifies the regions that form the substrate binding pocket. The light grey area identifies the regions that form the active site lid residues.

FIG. 12 shows an amino acid sequence of a terpene synthase of *Nodulisporium* (g226.t1, 339 amino acids; SEQ ID NO: 3).

FIG. 13 shows an amino acid sequence of a terpene synthase of *Nodulisporium* (g1080.t1, 365 amino acids; SEQ ID NO: 4).

FIG. 14 shows an amino acid sequence of a terpene synthase of *Nodulisporium* (g2861.t1, 293 amino acids; SEQ ID NO: 5).

FIG. 15 shows an amino acid sequence of a terpene synthase of *Nodulisporium* (g4788.t1, 541 amino acids; SEQ ID NO: 6).

FIG. 16 shows an amino acid sequence of a terpene synthase of *Nodulisporium* (g5351.t1, 373 amino acids; SEQ ID NO: 7).

FIG. 17 shows an amino acid sequence of a terpene synthase of *Nodulisporium* (g6654.t1, 348 amino acids; SEQ ID NO: 8).

FIG. 18 shows an amino acid sequence of a terpene synthase of *Nodulisporium* (g9560.t1, 313 amino acids; SEQ ID NO: 9).

FIG. 19 shows an amino acid sequence of a terpene synthase of *Nodulisporium* (g11102.t1, 417 amino acids; SEQ ID NO: 10).

FIG. 20 shows a nucleic acid sequence of a gene encoding terpene synthase from *Nodulisporium* (g226.t1, 1017 base pairs; SEQ ID NO: 11).

FIG. 21 shows a nucleic acid sequence of a gene encoding terpene synthase from *Nodulisporium* (g1080.t1, 1095 base pairs; SEQ ID NO: 12).

FIG. 22 shows a nucleic acid sequence of a gene encoding terpene synthase from *Nodulisporium* (g2861.t1, 879 base pairs; SEQ ID NO: 13).

FIG. 23 shows a nucleic acid sequence of a gene encoding terpene synthase from *Nodulisporium* (g4788.t1, 1623 base pairs; SEQ ID NO: 14).

FIG. 24 shows a nucleic acid sequence of a gene encoding terpene synthase from *Nodulisporium* (g5351.t1, 1119 base pairs; SEQ ID NO: 15).

FIG. 25 shows a nucleic acid sequence of a gene encoding terpene synthase from *Nodulisporium* (g6654.t1, 1044 base pairs; SEQ ID NO: 16).

FIG. 26 shows a nucleic acid sequence of a gene encoding terpene synthase from *Nodulisporium* (g9560.t1, 939 base pairs; SEQ ID NO: 17).

FIG. 27 shows a nucleic acid sequence of a gene encoding terpene synthase from *Nodulisporium* (g11102.t1, 1251 base pairs; SEQ ID NO: 18).

EXAMPLE 1

Fungal Isolates

Pieces of leaf and stem of *Lomatia fraserii* were collected during surveys in the Dandenong Ranges. Sections of leaf and stem were surface sterilised (70% Ethanol for 30 secs, flame sterilisation) prior to the excision of internal tissues, which were then plated onto potato dextrose agar (PDA) (39 g/L) (Amyl Media, Dandenong, Australia) amended with achromycin (50 ppm). Endophytic fungi growing from the plant tissue were removed by excising a hyphal tip from each colony, and plated onto PDA. Each hyphal tip constituted one endophytic fungal isolate. Isolates then underwent a preliminary screen for bioactivity by challenging them against *Rhizoctonia solani* on PDA. One isolate inhibited the growth of *R. solani* and was selected for further analysis.

In addition, pieces of wood from fallen logs of *Nothafagus cunninghamii* containing apothecia (gelatinous purple discs, sexual stage) or coniodamata (gelatinous purple fingers, asexual stage) characteristic of *Ascocoryne sarcoides* (FIG. 1) were collected during surveys in the Yarra Ranges and the Otway Ranges respectively. Sections of apothecia or conidiomata were surface sterilised (2% NaOCl for 30 secs, 2 washes in sterile distilled water, SDW) and plated onto PDA (39 g/L) (Amyl Media, Dandenong, Australia) amended with achromycin (50 ppm). Each apothecium or conidioma section comprised one isolate, with ten isolates collected in total, 6 from the Yarra Ranges and 4 from the Otway Ranges.

Pure cultures of the eleven fungal isolates (i.e. hyphal plugs) were placed in SDW and stored at room temperature and at 4° C., and in 15% glycerol at −70° C. Sections of conidiomata were placed in SDW and stored at room temperature.

EXAMPLE 2

Morphology

Isolates were removed from storage and placed onto PDA and allowed to grow at 25° C. (in the dark) until the formation of conidiophores. Sections of hyphae containing conidiophores were mounted in lactic acid and examined under light microscopy (in vitro description). In addition, sections of conidiomata from the *Ascocoryne* isolates were mounted in lactic acid and examined under light microscopy (in vivo description).

*Nodulisporium* State of *Hypoxylon*
Description in Vitro

Figure 2:
FIG. 2 shows Conidiophore ex-culture (*Nodulisporium*).

Colonies on PDA initially white, becoming pale yellow to grey yellow. Conidiophores branching loosely, pale brown, paler towards the apex, verruculose, 2.5-3 um wide. Conidiogenous cells usually produced singly, pale brown, verruculose, 12-20×2.5-3 um. Conidia borne from minutely visible denticles, pale brown, more or less smooth, ellipsoidal, 6-8×3-4 um (FIG. 2).

By evaluating the microscopic features of the isolates growing in culture (in vitro stage) we confirmed that they were characteristic of an undescribed species of *Nodulisporium*.

*Coryne* State of *Ascocoryne sarcoides*
Description in Vitro

Figure 3:
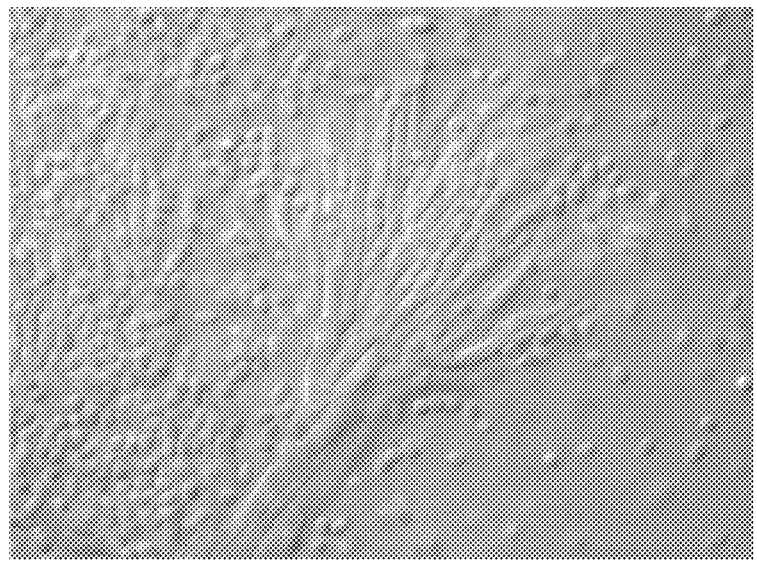
FIG. 3 shows Conidiophore ex culture (*A. sarcoides*).
Figure 4:
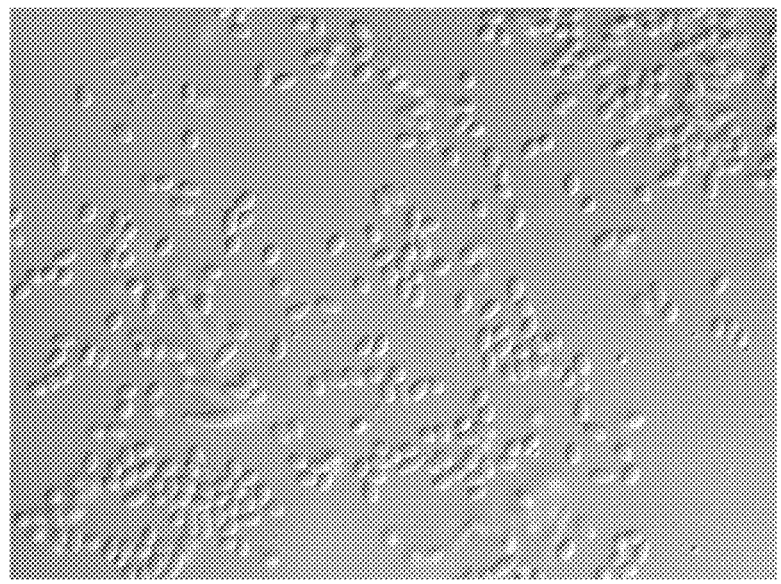
FIG. 4 shows Conidia ex culture (*A. sarcoides*).

Colonies on PDA initially white, becoming dark violet to grey violet, forming violet crystals in the medium. Conidiophores complex, branching 3-5 times, hyaline, thin walled (FIG. 3). Phialides hyaline, narrowly obclavate to cylindrical, straight to slightly curved, thin walled, 10-14×1.5-2 µm. Conidia hyaline, subglobose to ellipsoid, sometimes slightly curved, 2-5×1-2 µm (FIG. 4).

Description in Vivo

Conidiomata synemmatous, determinate, 3-5 mm×1-5 mm, dark purple, gelatinous, unbranched, subulate to capitate, gregarious. Hyphae of the stipe in two zones; the ectal excipulum a textura angularis, the medullary excipulum a textura intricata. Conidiophores complex, branching 3-4 times, hyaline, thin walled. Phialides hyaline, narrowly obclavate to cylindrical, straight to slightly curved, thin walled, 10-14×1.5-2 µm. Conidia hyaline, subglobose to ellipsoid, sometimes slightly curved, 2-5×1-2 µm.

By evaluating the microscopic features of the gelatinous purple fingers (conidomata, in vivo stage) and the isolates growing in culture (in vitro stage) we confirmed that they were characteristic of *A. sarcoides*.

EXAMPLE 3

Genotyping

A. DNA Sequencing—Ribosomal RNA

Genomic DNA was extracted from cultures of the *Nodulisporium* and *A. sarcoides* isolates grown in either PDA or potato dextrose broth (PDB) using a DNeasy Plant Mini Kit (Qiagen). A section of the ribosomal RNA loci (5.8S/ITS) was amplified with primers ITS4 and ITS5 (White et al., 1990). PCR amplifications were performed in 25 µL reaction volumes containing 1.0 U of Platinum Taq DNA Polymerase (Invitrogen), ×1 PCR buffer, 0.2 mM of each dNTP, 1.5 mM $MgCl_2$, 0.5 µM of each primer, and 15-25 µg DNA. Reactions were performed in a thermocycler (Gradient Palm-Cycler, Corbett Research) with cycling conditions consisting of denaturation at 94° C. (3 min), followed by 35 cycles at 94° C. (30 s), 50° C. (30 s), and 72° C. (2 min), with a final extension step at 72° C. (3 min) to complete the reaction. PCR products were separated by electrophoresis at 100 V for 45 min in a 1.5% (w/v) agarose gel (containing ethidium bromide, 0.1 ppm) in 0.5×TBE running buffer and visualised under UV light. Amplification products were purified using a PCR Purification Kit (Qiagen), and sequenced using the BigDye Terminator Cycle v 3.1 sequencing kit (Applied Biosystems) on the ABI 3730xl Capillary Sequencer (Applied Biosystems), according to manufacturers' instructions.

Sequences of Victorian isolates were compared to reference sequences from known *Nodulisporium* (or related teleomorphs, i.e. *Hypoxylon* and *Daldinia*) and *Ascocoryne* species (*A. sarcoides* or *A. cylichnium*) from around world (closest matches from GenBank). A total of 55 *Nodulisporium*-related sequences were aligned with MUSCLE (Edgar, 2004), while 26 *Ascocoryne*-related sequences were aligned. Aligned sequences were adjusted with ClustalW/Alignment Explorer in MEGA 4.1 (Tamura et al, 2007). Based on these sequences phylogenetic relationships were inferred using distance and maximum parsimony (MP) analyses. For distance analysis, phenograms were obtained using the neighbour-joining (NJ) algorithm (Saitou et al, 1987), applying the Kimura-2-parameter model (Kimura, 1980), as implemented in MEGA4.1. For MP analysis, phenograms were obtained using the Close-Neighbour-Interchange algorithm (search level 3) (Nei et al, 2000), as implemented in MEGA4.1. To find the global optimum phenogram 10 random sequences were added. Measurements calculated for MP included tree length, consistency index, retention index and rescaled consistency index (TL, CI, RI, RCI). In both analyses, alignment gaps and missing data were eliminated from the dataset (Complete deletion option) and the confidence of branching was assessed by computing 1000 bootstrap replications (Felsenstein, 1985).

Figure 5:
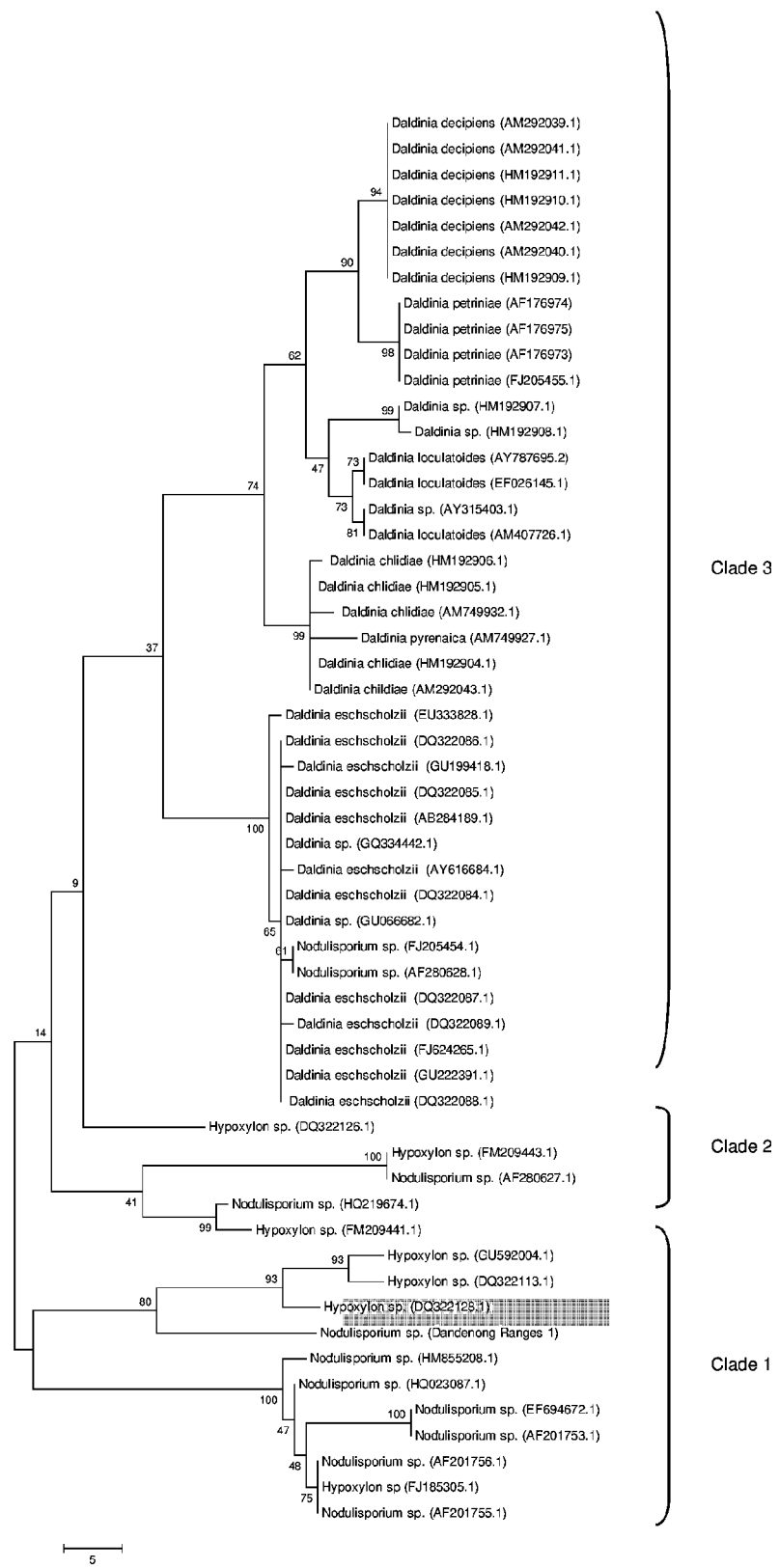
FIG. 5 shows A MP phenogram (1 of 8631) based on 5.8S/ITS rRNA gene sequences from 55 isolates of *Nodulisporium* and *Hypoxylon* species. Highlighted area (red) shows Victorian *Nodulisporium* isolate. The phenogram was obtained using the Close-Neighbour-Interchange algorithm of MEGA4.1 (deletion of gaps and missing data). Numbers on the nodes represent frequency (in per cent) with which a cluster appears in 1000 bootstrap tests. Scale bar equals 5 changes per 100 bases.

Of the 55 *Nodulisporium*-related isolates the size of the rRNA (5.8S/ITS) gene sequence ranged from 436-664 base pairs, of which 371 were included in the final data set for analysis. In the NJ analysis the optimal phenogram had a sum of branch length of 0.525. The MP analysis yielded 8631 most parsimonious phenograms (TL=211, CI=0.654 RI=0.916, RCI=0.569, for the parsimony informative sites). NJ and MP analyses yielded phenograms with similar topology and bootstrap values. Therefore, only the MP phenogram is presented (1 of 8631, FIG. 5).

Isolates tended to cluster according to the teleomorph of *Nodulsporium* species, *Hypoxylon* and *Daldinia*. The Dandenong Ranges isolate clustered with *Hypoxylon* species, with an 80% bootstrap support. This group formed a cluster with other *Nodulisporium* and *Hypoxylon* isolates, with a bootstrap support of 14% (Clade 1) This cluster was alongside another group of *Hypoxylon* isolates with a bootstrap support of 41% (Clade 2). A large group of *Daldinia* isolates formed the next related cluster with a 37% bootstrap support (Clade 3).

Figure 6:
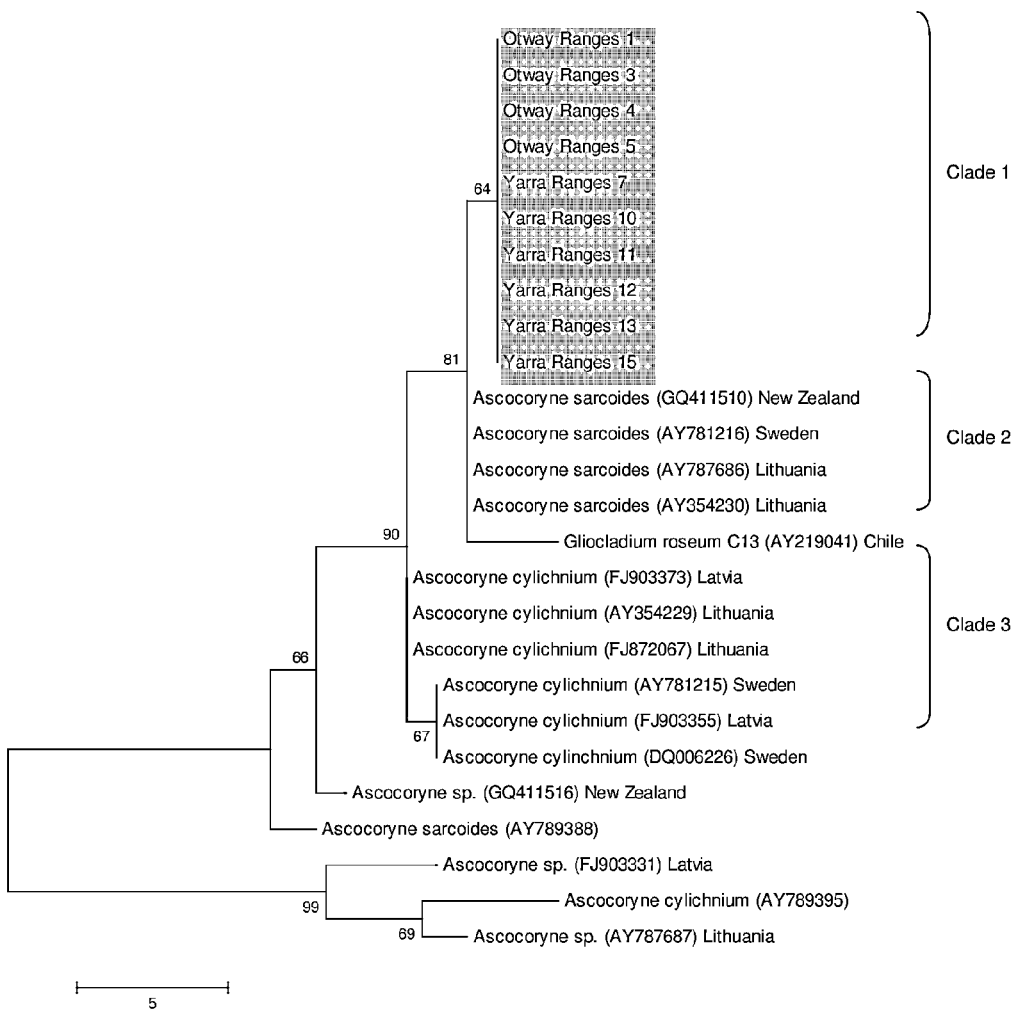
FIG. 6 shows A MP phenogram (199 of 330) based on 5.8S/ITS rRNA gene sequences from 26 isolates of *Ascocoryne* species. Highlighted area (grey) shows Victorian *A. sarcoides* isolates. The phenogram was obtained using the Close-Neighbour-Interchange algorithm of MEGA4.1 (deletion of gaps and missing data). Numbers on the nodes represent frequency (in per cent) with which a cluster appears in 1000 bootstrap tests. Scale bar equals 5 changes per 100 bases.

Of the 26 *Ascocoryne* isolates the average size of the rRNA (5.8S/ITS) gene sequence was approximately 569 base pairs, of which 436 were included in the final data set for analysis. In the NJ analysis the optimal phenogram had a sum of branch length of 0.103. The MP analysis yielded 330 most parsimonious phenograms (TL=46, CI=0.921, RI=0.964, RCI=0.888, for the parsimony informative sites). NJ and MP analyses yielded phenograms with similar topology and bootstrap values. Therefore, only the MP phenogram is presented (199 of 330, FIG. 6).

Isolates tended to cluster according to *Ascocoryne* species. All Victorian isolates clustered together, with 64% bootstrap support (Clade 1). They clustered alongside a group of *A. sarcoides* isolates from Lithuania, Sweden and New Zealand, with 81% bootstrap support (Clade 2). *Gliocladium roseum* also clustered with these *A. sarcoides* isolates. Finally, six isolates of *A. cylichnium* from Latvia, Lithuania and Sweden clustered together, with 90% bootstrap support (Clade 3).

B. Microsatellites—Simple Sequence Repeats (SSR)

Expressed sequence tag-simple sequence repeat (EST-SSR) markers developed by van Zijll de Jong (2003) were used to evaluate genetic diversity amongst ten Victorian *Ascocoryne* isolates. A total of 34 EST-SSR markers were initially evaluated, of which four were selected for routine genotyping based on their ability to detect levels of polymorphism between isolates (Table 1). PCR amplifications were performed in 20 µL reaction volumes containing 0.5 U Immolase (Bioline), 1×PCR buffer, 0.2 mM of each dNTP, 0.25 µM each primer, and 10 ng fungal genomic DNA. The forward primer was 5'-end labelled with a fluorescent phosphoramidite dye (6-FAM, HEX, or NED). Amplification was performed in a thermocycler using an appropriate touchdown profile depending on the $T_m$ value of the primer pairs: (Program 1, P1) 95° C. (10 min), 10 cycles at 94° C. (30 s), 55° C. (30 s) and 72° C. (1 min) with a reduction of annealing temperature of 1° C. every cycle, followed by 20 cycles at 94° C. (30 s), 45° C. (30 s), 72° C. (1 min); (Program 2, P2) a similar profile to (P1) with an initial annealing temperature of 60° C. and final annealing temperature of 50° C.; (Program 3, P3) a similar profile to (P1) with an initial annealing temperature of 65° C. and final annealing temperature of 55° C. PCR products (2 mL) were diluted 1:99 (P1 and P3) or 1:199 (P2), and analysed on the ABI 3730xl Capillary Sequencer (Applied Biosystems), according to manufacturers instructions.

TABLE 1

EST-SSR markers for determining genetic variation in *Ascocoryne* isolates from Victoria, Australia.

| Primer | | Primer sequence (5' → 3') | SEQ ID No | Label | PCR | Motif | No. of alleles | Size of products |
|---|---|---|---|---|---|---|---|---|
| NCESTA1DH04 | F | CAGTCCAAATCAGGCGGTAGCAGA | 19 | FAM | 1 | $(GTC)_8$ | 2 | 150/397 |
| | R | TGAGAAGGATCGGAATCGAGTGGT | 20 | | | | | |
| NCESTA1HA02 | F | TGCTCCTCGTCGACAGTTTCAAGT | 21 | HEX | 1 | $(CAG)_5$ | 1 | 259 |
| | R | CTTCATATTGGTTGTGCTGGACCC | 22 | | | | | |
| NLESTA1NF04 | F | AACCCGCTCCTACACTCGCCCAAT | 23 | NED | 2 | $(TGC)_8(TGA)_3$ $(TGG)_1(TGA)_3$ | 3 | 366/416/ 450 |
| | R | TCGGTAGCCGAGCAGCCTGCCTTG | 24 | | | | | |
| NLESTA1TA10 | F | TTTCCGACCCGCCAGACACC | 25 | FAM | 3 | $(TC)_{11}$ | 2 | 252/313 |
| | R | CCGGTCCTGCGATTCCTCCA | 26 | | | | | |

Products or alleles for each of the Victorian *Ascocoryne* isolates were characterised by size (i.e. number of base pairs) using GeneMapper version 3.7 software (Applied Biosystems). Isolates were then scored for the presence (1) and absence (0) of each allele. A similarity matrix was generated with this data using the Dice coefficient (Dice, 1945; NTSYSpc version 2.10t). Phenograms were constructed by the unweighted pair group method of arithmetic averages (SAHN program—UPGMA clustering method, NTSYSpc version 2.10t). The resulting genetic relationships were evaluated by cophenetic correlation and principle coordinate analysis (MXCOMP and EIGEN programs, NTSYSpc version 2.10t).

Of the 34 EST-SSR markers initially evaluated, 18 (53%) produced amplification products, but only four (12%) detected genetic polymorphism between the Victorian *Ascocoryne* isolates. Analysis of SSR polymorphism across the 10 Victorian isolates identified 8 different alleles.

Figure 7:
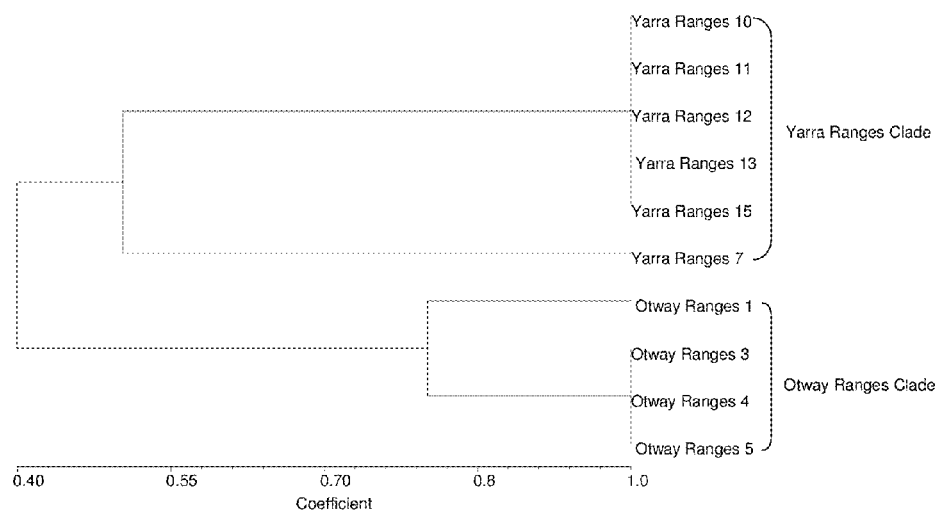
FIG. 7 shows UPGMA phenogram for Victorian *Ascocoryne* isolates using measurements of average taxonomic distance based on EST-SSRs.

A UPGMA phenogram constructed using the average taxonomic distance based on SSR polymorphism across the ten Victorian isolates, showed a separation largely based on the origin of the isolate (e.g. Otway Ranges cluster or Yarra Ranges cluster) (FIG. 7). Within the Yarra Ranges cluster the Yarra Ranges 7 isolate branched apart from the core cluster. Similarly, the Otway Ranges cluster branched apart leaving Otway Ranges 1 separated from the remaining Otway Ranges isolates. The cophonetic correlation between distance matrices was high (r=0.90).

EXAMPLE 4

Bioactivity

In vitro bioassays were established to test the bioactivity of Victorian *Nodulisporium* and *A. sarcoides* (Yarra Ranges only) isolates against a range of plant pathogenic fungi, *Fusarium oxysporum, Sclerotinia minor* and *Pythium ultimum*. *Nodulisporium* was compared against the bioactive endophytes *Muscodor albus* (CZ620) and Endophyte A. The bioassays used two types of Petri plates—standard 90 mm Petri plates for *A. sarcoides*, and 90 mm split Petri plates for *Nodulisporium*. The split plates consisted of an impermeable barrier through the centre of the plate, which completely separated the plate into two halves, with only volatile compounds capable of passing over the septum (i.e. no direct contact between test fungi or their liquid exudates). The isolates were inoculated on to Petri plates containing PDA by placing a 6 mm agar plug containing actively growing mycelia, 13 mm from the edge of the plate (i.e. on one half of the plate). Isolates were allowed to grow at 25 C (in the dark) for 7 days for *Nodulisporium* and 20 days for *A. sarcoides*. Subsequently, the plant pathogenic fungi were inoculated on to the other half of the plate by placing a 6 mm agar plug containing actively growing mycelia, 13 mm from the edge of the plate. Plates were sealed with LDPE plastic film (approximately 0.01 mm thick). After 5 days the growth of the plant pathogenic fungi were determined by measuring the radius of the colony (toward the centre of the plate). Measurements were compared to the control and expressed as percentage inhibition versus the control. Data were analysed using ANOVA as performed in GenStat, version 11 (Payne et al, 2008). The experiment was fully randomised with 3 replicates for *Nodulisporium* and *A. sarcoides*.

The *Nodulisporium* isolate showed strong levels of activity against the 3 horticultural crop pathogens, completely inhibiting the mycelial growth of *P. sulcatum* and *S. minor*, and inhibited the growth of *F. oxysporum* by up to 46.4% (Table 2). *Nodulisporium* also provided equivalent (or better) control of pathogens to the bioactive endophytes, *Muscodor albus* (CZ620) and Endophyte A.

TABLE 2

Percent inhibition of 3 plant pathogens (*Pythium sulcatum*, *Fusarium oxysporum* and *Sclerotinia minor*) following exposure (5 days) to volatile secondary metabolites produced by an isolate of Nodulisporium from the Dandenong Ranges, Victoria, compared to *Muscodor albus* and Endophyte A.

| Isolate | Pythium sulcatum (% Inhibition) | Fusarium oxysporum (% Inhibition) | Sclerotinia minor (% Inhibition) |
|---|---|---|---|
| Dandenong Ranges 1 | 100.0% $^a$ | 46.4% $^a$ | 100.0% $^a$ |
| Muscodor albus (CZ620) | 100.0% $^a$ | 32.3% $^b$ | 100.0% $^a$ |
| Endophyte A | 55.5% $^b$ | 2.9% $^c$ | 44.7% $^b$ |
| LSD (5%) | 5.9% | 8.5% | 18.2% |
| F Pr. | 0.01 | 0.01 | 0.01 |

Figure 8:
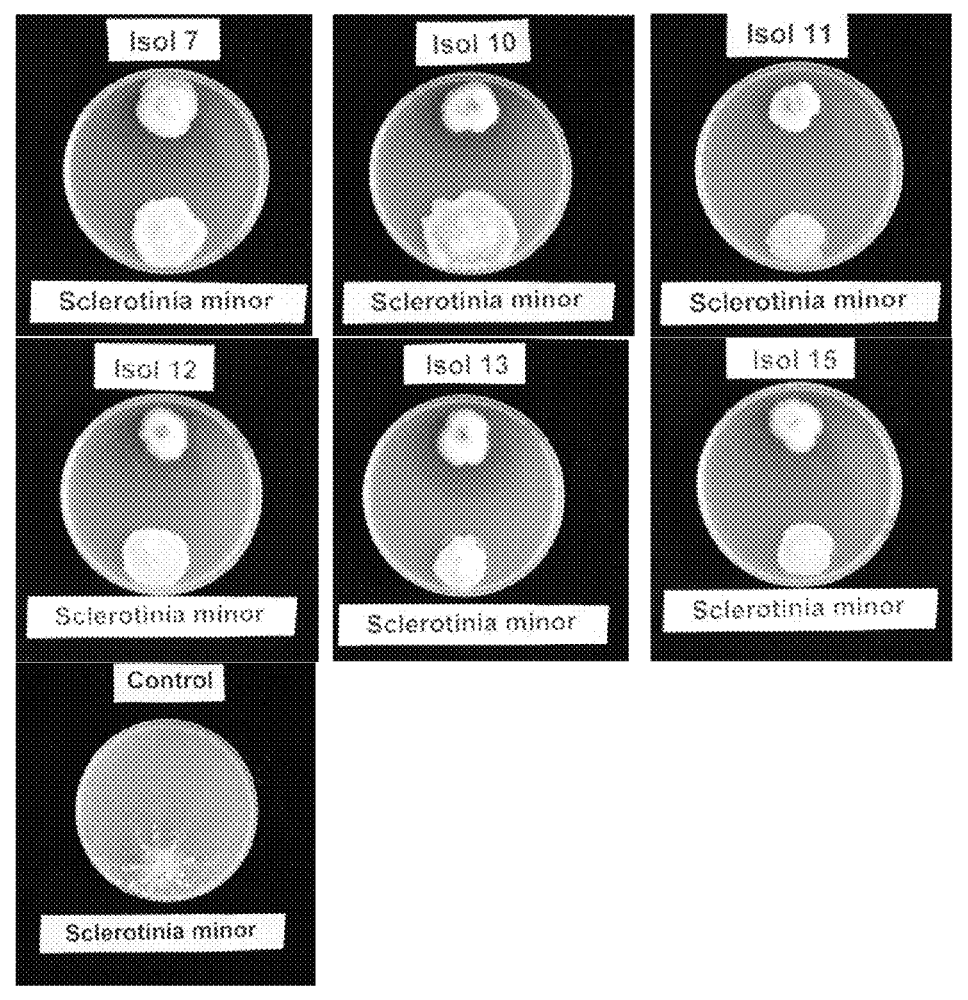

Isolates of *A. sarcoides* from the Yarra Ranges inhibited mycelial growth of *F. oxysporum* and *S. minor* (Table 3, FIG. 8). Yarra Ranges 11 was the most active isolate against *F. oxysorum* and *S. minor*, inhibiting mycelial growth by 31.8% and 85.0% respectively. Yarra Ranges 11 had significantly greater activity against *F. oxysporum* than all other isolates. Yarra Ranges 11, 12, 13 and 15 were the most active isolates against *S. minor*, significantly greater than Yarra Ranges 7 and 10.

TABLE 3

Percent inhibition of two plant pathogenic fungi (*F. oxysporum* and *S. minor*) following exposure (5 days) to isolates of *A. sarcoides* from the Yarra Ranges, Victoria.

| | Fusarium oxysporum (% Inhibition) | Sclerotinia minor (% Inhibition) |
|---|---|---|
| Yarra Ranges 7 | 22.7% $^{ab}$ | 77.3% $^b$ |
| Yarra Ranges 10 | 26.1% $^{cd}$ | 71.0% $^a$ |
| Yarra Ranges 11 | 31.8% $^e$ | 85.0% $^c$ |
| Yarra Ranges 12 | 22.7% $^{ab}$ | 81.2% $^{bc}$ |
| Yarra Ranges 13 | 21.6% $^a$ | 83.1% $^c$ |
| Yarra Ranges 15 | 23.9% $^{abc}$ | 81.2% $^{bc}$ |
| LSD (p = 0.05) | 3.1% | 3.9% |
| F Pr. | <0.001 | <0.001 |

EXAMPLE 5

Metabolite Production

A. Qualitative Analysis of Major Non-Polar Fungal Gases

Gases were analysed in the head space above cultures of *Nodulisporium*. The isolate was cultured under microaerophilic conditions, which consisted of growing the fungus on PDA slopes (39 g/L) (Amyl Media Pty Ltd) in 20 ml glass vials, with an agar:air ratio of 1:2.5. Vials were sealed with a screw cap lid with PTFE septum, and grown for 22 days at room temperature.

A head space solid phase microextraction (SPME) was performed to capture volatiles produced by *Nodulisporium*. A StableFlex fibre (Supelco) consisting of a matrix of divinylbenzene/carboxen (DVB/CAR) on polydimethylsiloxane (PDMS) (50/30 um) was used to absorb volatiles from the head space of vials. Automated sampling was performed by an Agilent GC Sampler combined with Gerstel Maestro software. The fibre was conditioned (baked at 250° C.) daily for 20 minutes prior to commencement of activities and for 2 minutes between each sample. For each sample the fibre was inserted into the vial and incubated at room temperature for 5 minutes to absorb volatiles, after which the fibre was inserted into a splitless injection port of an Agilent 7890 GC System where the contents was thermally desorbed (250° C. for 6 mins) onto a capillary column (Agilent HP-5 ms, 30 m×250 um id., 0.25 um film thickness) coupled with a deactivated fused silica guard (Agilent, 6.02 m.×250 um id.). The column oven was programmed as follows: 40° C. (3.5 min), 5° C./min to 200° C., hold at 200° C. (2 min). The carrier gas was helium with a constant flow rate of 1.2 mL/min. The GC was interfaced with an Agilent 7000 GC/MS triple quadruple mass selective detector (mass spectrometer, MS) operating in electron impact ionization mode at 70 eV. The temperature of the transfer line was held at 280° C. during the chromatographic run. The source temperature was 280° C. Acquisitions were carried out over a mass range of 35-450 mz, with a scan time of 300 ms.

Initial identification of the volatiles produced by the *Nodulisporium* isolates was made through library comparison using standard chemical databases. Secondary confirmatory identification was made by comparing mass spectral data of authentic standards with data of the fungal volatiles. All chemical names in this patent application follow the nomenclature of the standard chemical databases. In all cases, uninoculated control vials were also analysed and the compounds found therein were subtracted from those appearing in the vials supporting fungal growth. Tentative identification of the fungal volatiles was based on observed mass spectral data as compared to those in these chemical databases and those of authentic standards (where possible).

Figure 9:
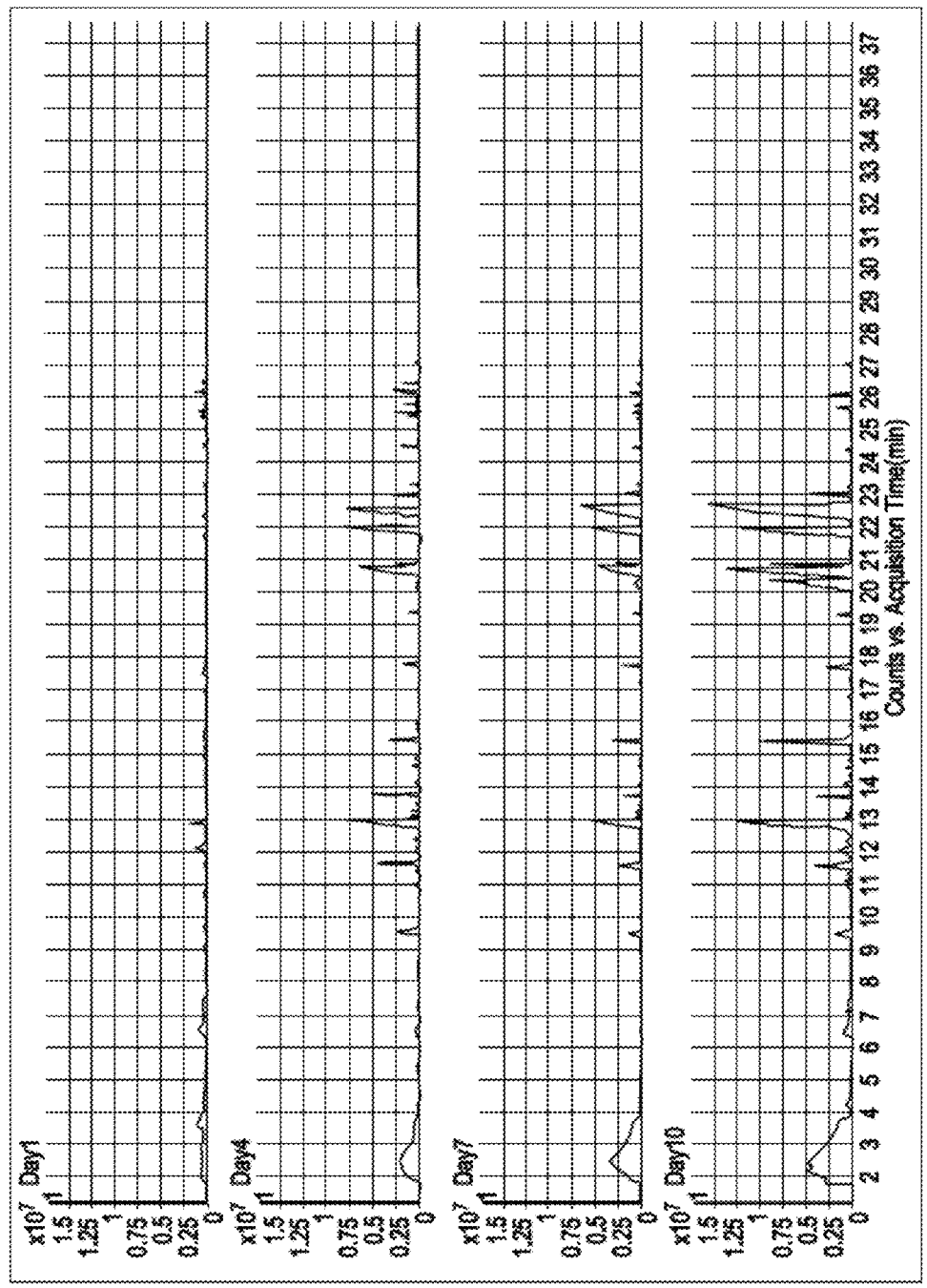
FIG. 9 shows a GC/MS headspace analysis of volatile compounds produced by *Nodulisporium* sp. (Dandenong Ranges 1) when grown on PDA for 1, 4, 7, 10, 13, 16, 19 and 22 days growth. Each total ion chromatograph (TIC) represents one day.
Figure 9:
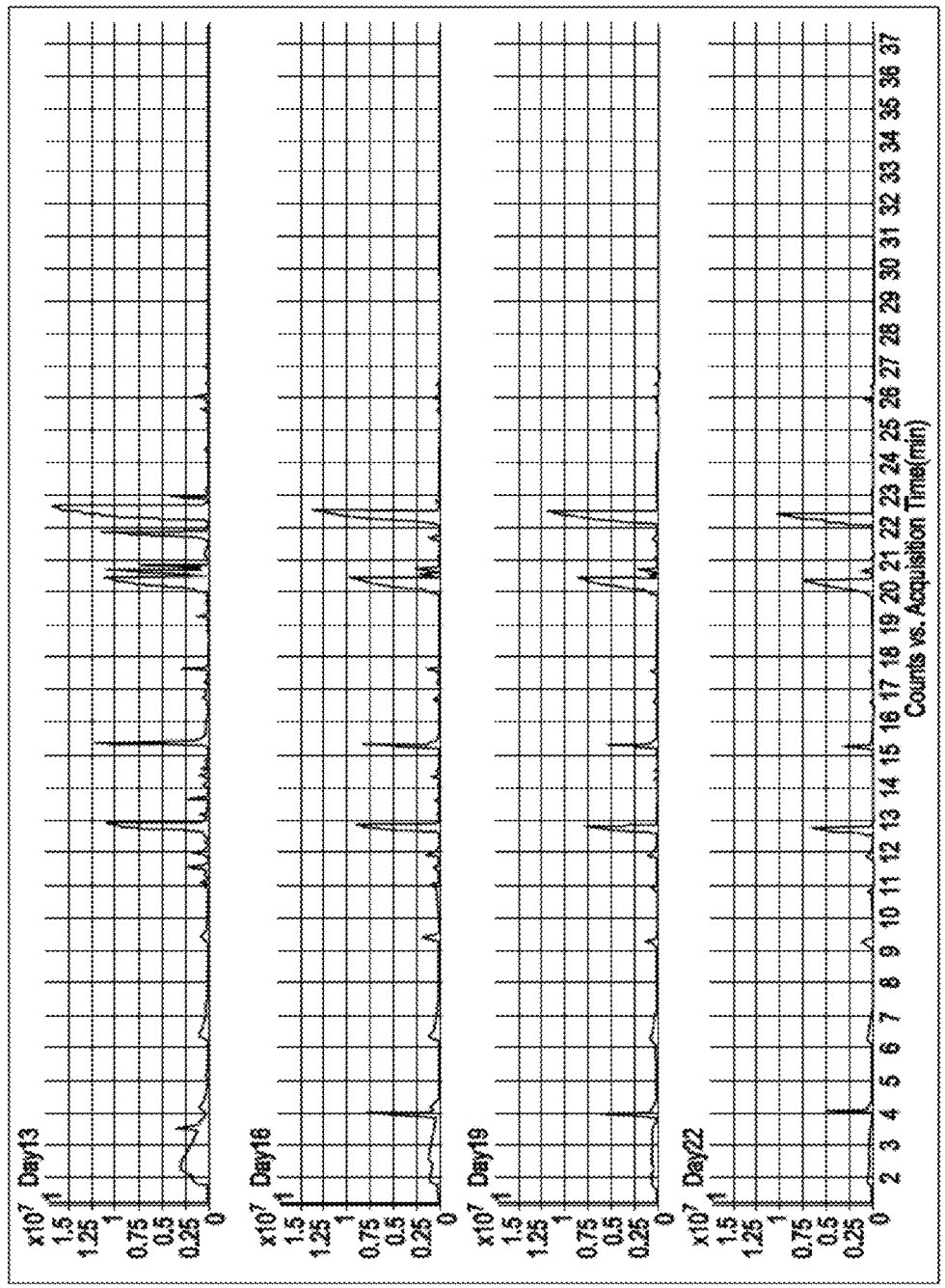
Figure 10:
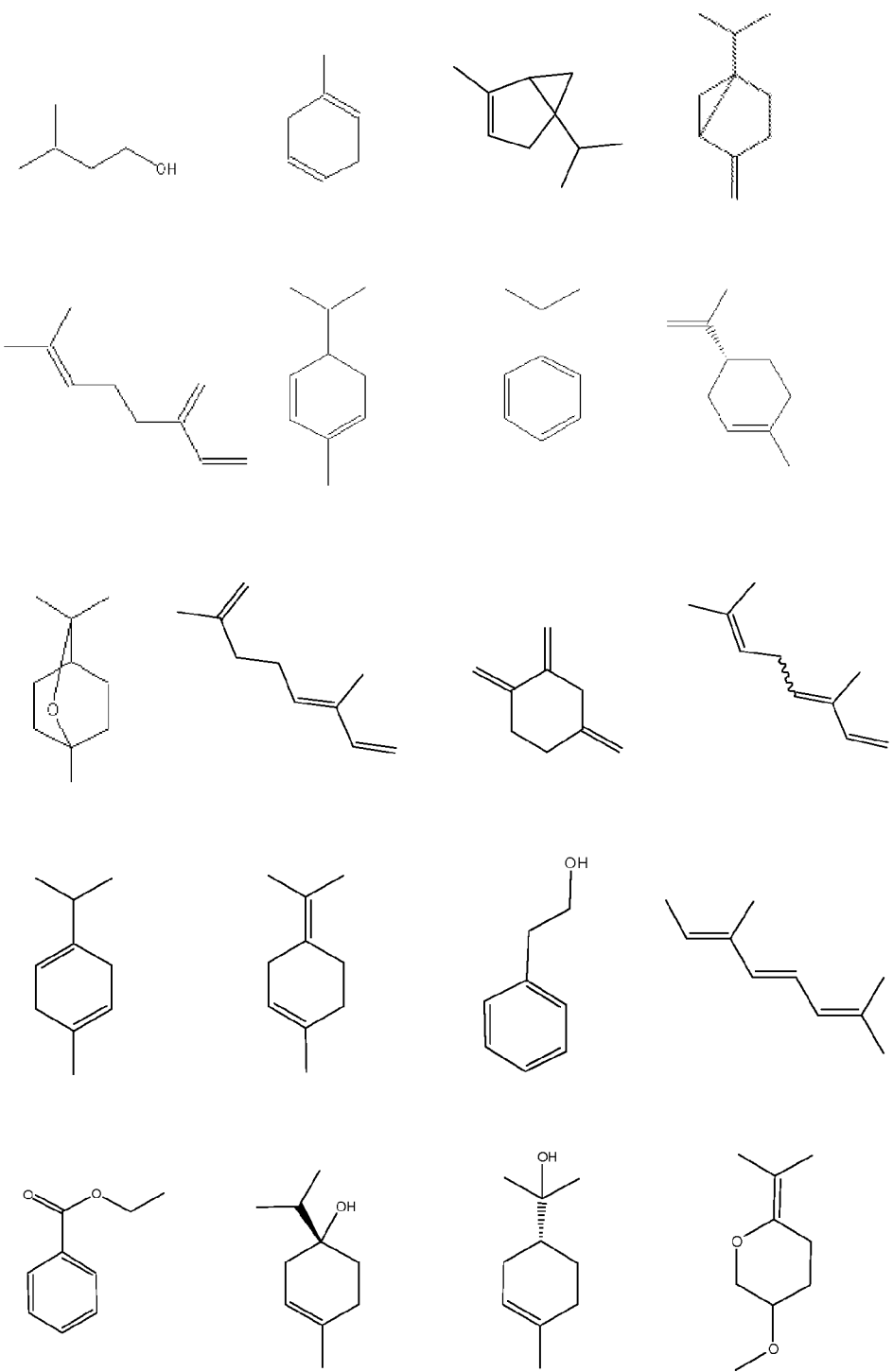
FIG. 10 shows the chemical structures of volatile compounds produced by *Nodulisporium* sp. (Dandenong Ranges 1). Names of compounds (from left to right, line by line) are as follows.
Figure 10:
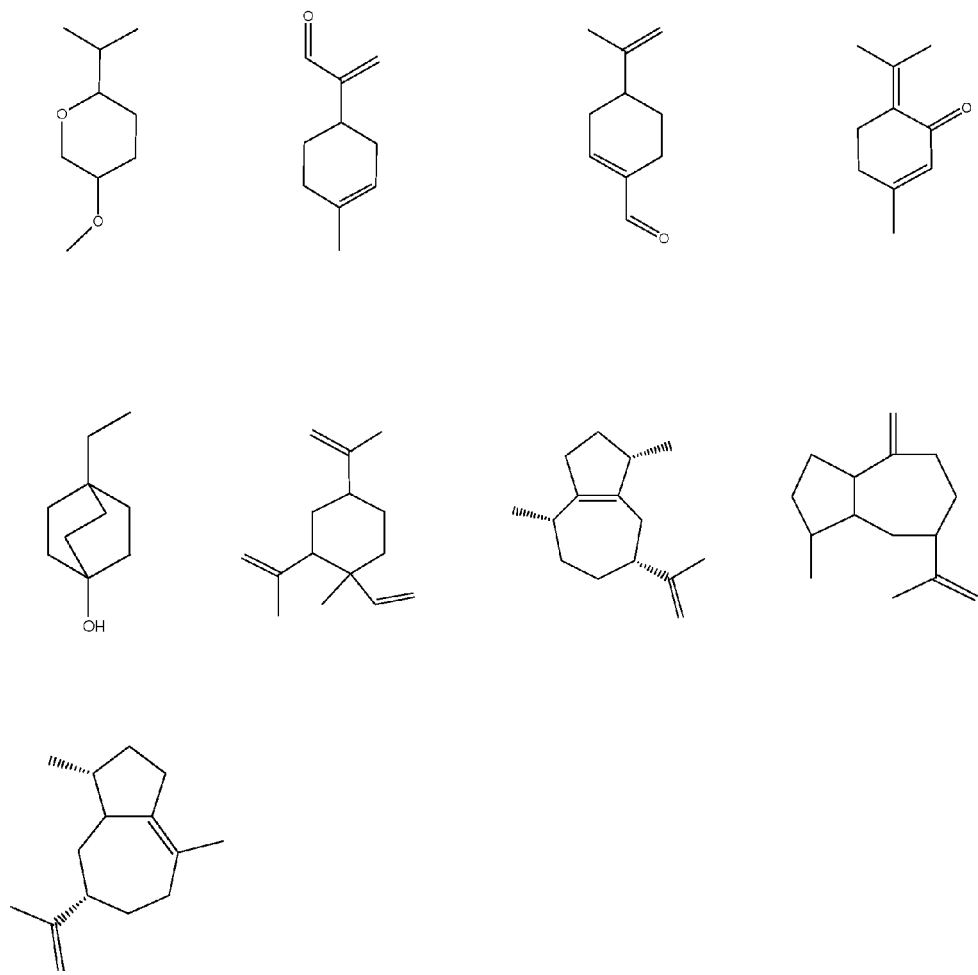

The GC-MS analysis (0-37.5 mins) identified 58 volatile metabolites produced by *Nodulisporium* when grown for 1-22 days on PDA at room temperature (Table 4, FIGS. 9 and 10). The metabolites produced by *Nodulisporium* were representatives of a number of structural classes, with the terpenes predominating, accounting for over 82% of the compounds produced by *Nodulisporium*. There were 21 monoterpenes (α-Thujene, β-Sabinene, β-Myrcene, α-Phellendrene, α-Terpinene, p-Cymene, (R)-(+)-Limonene, Eucalyptol, α-Ocimene, β-Ocimene, γ-Terpinene, α-Terpinolene, Allo-Ocimene, (−)-Terpinen-4-ol, α-Terpineol, 2H-pyran, tetrahydro-2-(propan-2-ylidene)-5-methoxy, 2H-pyran,tetrahydro-2-isopropyl-5-methoxy, 3-Cyclohexene-1-acetaldehyde,4-methyl-α-methylene-, 1-Cyclohexene-1-carboxaldehyde,4-(1-methylethenyl)-, p-Mentha-1,4(8)-dien-3-one (isomers), Bicyclo[2.2.2]octan-1-ol,4-ethyl,) and four sesquiterpenes (β-Elemene, α-Guajene, Bicyclo[5.3.0] decane,2 methylene-5-(1-methylvinyl)-8-methyl, δ-Guaijene) produced by *Nodulisporium*. A further 16 monoterpene-like compounds and seven sesquiterpene-like compounds were produced by *Nodulisporium*. (Table 4 FIGS. 9 and 10). These terpenes had masses consistent with mono and sesquiterpenes, and were structurally similar based on their ion fragmentation. Fragmentation patterns also indicated the presence of a cyclohexane, cyclohexene or pyran ring as the primary structure), which is consistent with cyclic monoterpenes.

TABLE 4

GC-MS headspace analysis of the volatile compounds produced by *Nodulisporium* (Dandenong Ranges 1) when grown on PDA for 1-22 days at room temperature.

|  | RT | Peak Name | Standard | Formula | Mass | Area |
|---|---|---|---|---|---|---|
| 1 | 4.098 | 1 Butanol, 3-methyl- |  | $C_5H_{12}O$ | 88 | + |
| 2 | 5.032 | 1,4-Cyclohexadiene, 1-methyl- |  | $C_7H_{10}$ | 94 | + |
| 3 | 9.312 | α-Thujene |  | $C_{10}H_{16}$ | 136 | + |
| 4 | 10.868 | β-Sabinene |  | $C_{10}H_{16}$ | 136 | + |
| 5 | 11.198 | Unknown |  |  | 126 | + |
| 6 | 11.425 | β-Myrcene | Y | $C_{10}H_{16}$ | 136 | +++ |
| 7 | 11.806 | α-Phellandrene | Y | $C_{10}H_{16}$ | 136 | + |
| 8 | 12.217 | α-Terpinene | Y | $C_{10}H_{16}$ | 136 | + |
| 9 | 12.578 | ρ-Cymene | Y | $C_{10}H_{14}$ | 134 | + |
| 10 | 12.575 | (R)-(+)-Limonene | Y | $C_{10}H_{16}$ | 136 | + |
| 11 | 12.825 | Eucalyptol | Y | $C_{10}H_{18}O$ | 154 | ++++ |
| 12 | 12.941 | α-Ocimene |  | $C_{10}H_{16}$ | 136 | + |
| 13 | 13.075 | Cyclohexane, 1,2,4-tris(methylene)- |  | $C_9H_{12}$ | 120 | + |
| 14 | 13.249 | β-Ocimene | Y | $C_{10}H_{16}$ | 136 | + |
| 15 | 13.558 | γ-Terpinene | Y | $C_{10}H_{16}$ | 136 | +++ |
| 16 | 13.906 | Unknown[#] |  |  | 138 | + |
| 17 | 13.969 | Unknown[#] |  |  | 136 | + |
| 18 | 14.268 | Unknown[#] |  |  | 140 | + |
| 19 | 14.469 | α-Terpinolene | Y | $C_{10}H_{16}$ | 136 | + |
| 20 | 14.581 | Unknown[#] |  |  | 142 | + |
| 21 | 14.787 | Unknown[#] |  |  | 138 | + |
| 22 | 14.934 | Unknown[#] |  |  | 136 | + |
| 23 | 15.261 | Phenylethyl alcohol |  | $C_8H_{10}O$ | 122 | ++++ |
| 24 | 15.546 | Unknown[#] |  |  | 138 | + |
| 25 | 15.725 | Allo-Ocimene |  | $C_{10}H_{16}$ | 136 | + |
| 26 | 16.864 | Unknown[#] |  |  | 136 | + |
| 27 | 16.972 | Benzoic acid ethyl ester |  | $C_9H_{10}O_2$ | 150 | + |
| 28 | 17.159 | (−)-Terpinen-4-ol |  | $C_{10}H_{18}O$ | 154 | + |
| 29 | 17.566 | α-Terpineol | Y | $C_{10}H_{18}O$ | 154 | +++ |
| 30 | 18.679 | Unknown[#] |  |  | 180 | + |
| 31 | 19.171 | Unknown[#] |  |  | 150 | ++ |
| 32 | 19.470 | Unknown[#] |  |  | 152 | + |
| 33 | 19.899 | Unknown[#] |  |  | 152 | + |
| 34 | 19.987 | 2H-pyran, tetrahydro-2-(propan-2-ylidene)-5-methoxy |  | $C_9H_{16}O_2$ | 156 | ++++ |
| 35 | 20.124 | 2H-pyran, tetrahydro-2-isopropyl-5-methoxy |  | $C_9H_{18}O_2$ | 158 | ++++ |
| 36 | 20.287 | Unknown[#] |  |  | 152 | + |
| 37 | 20.457 | Unknown[#] |  |  | 154 | + |
| 38 | 20.506 | 3-Cyclohexene-1-acetaldehyde, 4-methyl-α-methylene- |  | $C_{10}H_{14}O$ | 150 | ++++ |
| 39 | 20.676 | 1-Cyclohexene-1-carboxaldehyde, 4-(1-methylethenyl)- |  | $C_{10}H_{14}O$ | 150 | ++++ |
| 40 | 21.074 | Unknown[#] |  |  | 152 | + |
| 41 | 21.159 | Unknown[#] |  |  | 148 | + |
| 42 | 21.744 | ρ-Mentha-1,4(8)-dien-3-one (isomer) |  | $C_{10}H_{14}O$ | 150 | ++++ |
| 43 | 22.526 | Bicyclo[2.2.2]octan-1-ol,4-ethyl |  | $C_{10}H_{18}O$ | 154 | +++++ |
| 44 | 22.849 | ρ-Mentha-1,4(8)-dien-3-one (isomer) |  | $C_{10}H_{14}O$ | 150 | +++ |
| 45 | 23.086 | Unknown |  |  | 168 | + |
| 46 | 23.129 | β-Elemene | Y | $C_{15}H_{24}$ | 204 | + |
| 47 | 24.297 | α-Guajene |  | $C_{15}H_{24}$ | 204 | + |
| 48 | 25.203 | Unknown^ |  |  | 204 | + |
| 49 | 25.364 | Unknown^ |  |  | 204 | + |
| 50 | 25.440 | Unknown^ |  |  | 204 | + |
| 51 | 25.493 | Unknown^ |  |  | 204 | + |
| 52 | 25.580 | Bicyclo[5.3.0]decane, 2 methylene-5-(1-methylvinyl)-8-methyl |  | $C_{15}H_{24}$ | 204 | + |

TABLE 4-continued

GC-MS headspace analysis of the volatile compounds produced by *Nodulisporium* (Dandenong Ranges 1) when grown on PDA for 1-22 days at room temperature.

| | RT | Peak Name | Standard | Formula | Mass | Area |
|---|---|---|---|---|---|---|
| 53 | 25.712 | Unknown^ | | | 204 | + |
| 54 | 25.806 | Unknown^ | | | 204 | + |
| 55 | 25.998 | δ-Guaijene | | $C_{15}H_{24}$ | 204 | ++ |
| 56 | 26.262 | Unknown^ | | | 204 | + |
| 57 | 26.870 | Unknown | | | 238 | + |
| 58 | 26.959 | Unknown | | | 238 | + |

Fragmentation pattern suggests a monoterpene-like compound derived from of a cyclohexane/ene or pyran substructure
^Fragmentation pattern suggests a sesquiterpene-like compound

EXAMPLE 6

Gene Regulation

Genome Sequencing

The genome of *Nodulisporium* sp. (Dandenong Ranges 1) was sequenced using the Genome Sequencer FLX Titanium (GS FLX Titanium), using standard and modified protocols for this technology. A shotgun library of the fungal isolate was prepared from 5 μg of intact genomic DNA, as per the DNeasy Plant Mini Prep (Qiagen) protocol. Following library preparation, the resulting single stranded (ss) DNA library showed a fragment distribution between 500 and 2000 bp, with an average of 750 bp. The optimal amount of ssDNA library input for the emulsion PCR (emPCR) was determined empirically through two small-scale titrations leading to 1.7 molecules per bead used for the large-scale approach. The large-scale emPCR generated 4,602,000 DNA-carrying beads for the two-region-sized 70×75 mm PicoTiterPlate (PTP). One region was subsequently loaded with 2,000,000 DNA-carrying beads. During the sequencing run a total of 200 cycles of nucleotide flows (flow order TACG) were performed, which were assessed via a pipeline of 454 Life Sciences/Roche Diagnostics software Version 1.1.03. The output consisted of a Standard Flowgram Format (sff) file that provided information about read flowgrams, basecalls, and per base quality scores. The sff file was subsequently used to assemble (de novo) high quality reads into contiguous sequences using the 454 Life Sciences/Roche Diagnostics software, Newbler v2.3 (gsAssembler).

The GS FLX Titanium sequencing run yielded 663,514 high quality reads, with an average read length of over 420 bp. A total of 6,938 contigs were assembled de novo, of which 6,165 were larger than 500 bp. Overall, contigs contained around 33.9 Mb of sequence, at sequencing depth of ×6.0. The contig size (x̄/n50) was 5.4/8.6 kbp. The largest contig was 47.4 kbp.

In addition, the genome of *Nodulisporium* sp. (Dandenong Ranges 1) was sequenced using the Illumina HiSeq platform using standard and adapted protocols for this technology. A paired end library of the isolate was prepared from 2 ug of intact genomic DNA as per the DNeasy Plant Mini Prep (Qiagen) protocol. DNA was sheared to fragments of 200-700 bp, end-repaired, A-tailed and ligated to Illumina paired end adaptors. The ligated fragments were size selected at 400 and 600 bp on agarose gels, ligated again with multiplex adaptors and amplified to the desired concentration by qPCR and PCR. Finally, libraries were titrated (KAPA) to accurately measure the number of competent molecules present. Library concentrations were adjusted and sequenced on the Illumina HiSeq 2000, with read lengths of 90-100 bp. Raw sequences were filtered for low quality and short length, and trimmed of adapter sequence and paired-end read overlap. The Illumina HiSeq sequencing run yielded 23,354,002 raw reads, of which 11,677,001 were deemed of high quality.

High quality reads from both the GS FLX Titanium and Illumina HiSeq sequencing runs were then assembled with Velvet to construct contigs. A total of 4299 contigs were assembled de novo, of which 1543 were greater than 1 kb (large contigs). The total number of bases in large contigs totalled 37.8 MB with an estimated sequencing depth of ×25.0. The contig n50 was 101.5 kbp with the largest contig measuring 397.3 kbp.

Gene Prediction

The gene prediction program Augustus was used to predict coding domains in the contigs of *Nodulisporium*, according to manufacturer's instructions. In Augustus, trained models of a closely related species, *Aspergillus oryzae*, was used to predict coding regions in contigs of *Nodulisporium*. A total of 9,958 coding regions were predicted for *Nodulisporium* from the assembly.

Gene Annotation

The predicted genes were then compared against the Conserved Domain Database (CDD) and the non-redundant protein database (NRPD) to determine putative function. The comparison was completed using the NCBI alignment tools RPS-BLAST (CDD) and BLAST-P (NRPD) Of the 9958 predicted genes for *Nodulisporium* 6525 were found to contain functional coding domains when compared against the CDD (evalue>1e-5).

An analysis of the specific function of coding domains identified a number of unique genes in *Nodulisporium*, which are involved in the regulation of key secondary metabolites. A total of 8 putative genes were found to contain non-plant terpene synthase domains (FIG. 11, Table 6). The average length of the putative non-plant terpene synthase genes from *Nodulisporium* was 376 amino acids. The eight gene sequences are represented in FIGS. 12-19 (amino acid sequences) and FIGS. 20-27 (nucleic acid sequences).

TABLE 6

Features of putative non-plant terpene synthase genes from *Nodulisporium* (bp—base pairs; aa—amino acid).

| Contig | Contig Length (bp) | Gene | Gene Length (bp) | Gene Length (aa) | Evalue* |
|---|---|---|---|---|---|
| 297 | 15247 | g226 | 1017 | 339 | $4.66 \times 10^{-58}$ |
| 58 | 91070 | g1080 | 1095 | 365 | $8.06 \times 10^{-16}$ |
| 1132 | 179839 | g2861 | 879 | 293 | $2.75 \times 10^{-19}$ |
| 4952 | 55485 | g4788 | 1623 | 541 | $5.15 \times 10^{-7}$ |
| 334 | 34511 | g5351 | 1119 | 373 | $3.66 \times 10^{-28}$ |

TABLE 6-continued

Features of putative non-plant terpene synthase genes from
*Nodulisporium* (bp—base pairs; aa—amino acid).

| Contig | Contig Length (bp) | Gene | Gene Length (bp) | Gene Length (aa) | Evalue* |
|---|---|---|---|---|---|
| 4952 | 55485 | g6654 | 1044 | 348 | $1.81 \times 10^{-8}$ |
| 364 | 85750 | g9560 | 939 | 313 | $5.99 \times 10^{-51}$ |
| 789 | 225983 | g11102 | 1251 | 417 | $3.76 \times 10^{-23}$ |

*Evalue represents sequence similarity between amino acid gene sequences of *Nodulisporium* and sequences within the Conserved Domain Database (NCBI), generated via a RPS-BLAST comparison When the 8 putative terpene synthase genes were compared against the NRPD, sequences were found to be highly similar to terpene synthases from the fungi *Leptosphaeria maculans, Trichoderma reesei, Aspergillus* species and *Penicillium* species, and the bacterium *Nostoc punctiforme* (Table 7). Sequences from *Penicillium rocquerfortii* and *Aspergillus terreus* are known to regulate the production of sesquiterpenes, providing evidence to suggest g226 and g9560 may regulate the production of the sesquiterpenes identified in the volatile bioactive compounds. The remaining genes may regulate the production of the monoterpenes in *Nodulisporium*.

TABLE 7

Sequence similarity between the 8 putative terpene synthase genes from *Nodulisporium* and sequences from the Non-redundant Protein Database. The top two matches are presented.

| Gene | Genbank Accession | Terpene Synthase | Organism | E value |
|---|---|---|---|---|
| g226 | Q03471.1 | Terpene Synthase (Sesqui-) | *Penicillium rocquertfortii* | $1.6 \times 10^{-118}$ |
| g226 | 1D\|1\|A | Terpene Synthase (Sesqui-) | *Penicillium rocquertfortii* | $2.8 \times 10^{-116}$ |
| g1080 | \|XP_002849193.1 | Hypothetical Protein | *Arthroderma otae* | $4.6 \times 10^{-29}$ |
| g1080 | CBY01604.1 | Terpene Synthase | *Leptosphaeria maculans* | $7.9 \times 10^{20}$ |
| g2681 | XP_002479429.1 | Hypothetical Protein | *Talaromyces stipitatus* | $3.2 \times 10^{44}$ |
| g2681 | XP_001826046.2 | Terpene Synthase | *Aspergillus oryzae* | $7.4 \times 10^{38}$ |
| g4788 | XP_001400832.2 | Hypothetical Protein | *Aspergillus niger* | $5.9 \times 10^{-47}$ |
| g4788 | \|XP_001262485.1 | Hypothetical Protein | *Neosartorya fischeri* | $2.9 \times 10^{-46}$ |
| g5351 | EGR44655.1 | Terpene Synthase | *Trichoderma reesei* | $8.9 \times 10^{-166}$ |
| g5351 | XP_002149866.1 | Terpene Synthase | *Penicillium marneffei* | $3.2 \times 10^{-130}$ |
| g6654 | XP_002390417.1 | Hypothetical Protein | *Moniliophthora perniciosa* | $5.0 \times 10^{-72}$ |
| g6654 | XP_001550978.1 | Hypothetical Protein | *Botryotinia fuckeliana* | $1.6 \times 10^{-41}$ |
| g9560 | 2E4O\|A | Terpene Synthase (Sesqui-) | *Aspergillus terreus* | $6.2 \times 10^{-125}$ |
| g9560 | Q03471.1 | Terpene Synthase (Sesqui-) | *Penicillium rocquertfortii* | $1.9 \times 10^{-100}$ |
| g11102 | EGR47124.1 | Hypothetical Protein | *Trichoderma reesei* | $8.0 \times 10^{-51}$ |
| g11102 | EFQ28833.1 | Hypothetical Protein | *Glomerella graminicola* | $8.9 \times 10^{-40}$ |

*Evalue represents sequence similarity between amino acid gene sequences of *Nodulisporium* and sequences within the Non-redundant Protein Database (NCBI), generated via a BLAST-P comparison It is widely regarded genes regulating fungal secondary metabolism are commonly found in clusters, including those regulating terpene synthesis (e.g. gibberellin—7 genes, trichothecene—11 genes). All of the putative terpene synthases identified in *Nodulisporium* were located on large contigs (>15247 bp) enabling flanking genes to be comprehensively evaluated. The putative function of common flanking genes included cytochrome p450 oxidases (add oxygen functional groups), transporters (transmembrane proteins for antibiotic resistance) and protein kinases (gene regulation). For instance, g5351 is located alongside a putative p450, a transporter and a polyprenyl synthase (precursor compounds to terpenes). Similarly g4788 and 6654 are located on the same contig, 3 genes apart. One of the genes separating the putative terpene synthases is a putative transporter. These flanking genes provide further evidence to suggest that the putative terpene synthases are regulating mono- and sesquiterpene synthesis.

REFERENCES

1. Edgar R C (2004) MUSCLE: multiple sequence alignment with high accuracy and high throughput. *Nucleic Acids Research* 32, 1792-1797.
2. Felsenstein J (1985) Confidence limits on phylogenies: An approach using the bootstrap. *Evolution* 39:783-791.
3. Kimura M. (1980). A simple method for estimating evolutionary rates of base substitution through comparative studies of nucleotide sequences. *Journal of Molecular Evolution.* 16:111-120.
4. Marchler-Bauer A, Anderson J, Chitsaz F, Derbyshire M, DeWeese-Scott C, Fong J, Geer L, Geer R, Gonzales N, Gwadz M, He S, Hurwitz D, Jackson J, Ke Z, Lanczycki C, Liebert C, Liu C, Lu F, Lu S, Marchler G, Mullokandov M, Song J, Tasneem A, Thanki N, Yamashita R, Zhang D, Zhang N and Bryant S (2009) CDD: specific functional annotation with the Conserved Domain Database. *Nucleic Acids Research* 37, D205-10.
5. Nei M and Kumar S (2000) *Molecular Evolution and Phylogenetics*. Oxford University Press, New York.
6. Payne R W, Murray D A, Harding S A, Baird D B. and Soutar D M. (2008). *GenStat for Windows* (11th Edition) *Introduction*. VSN International, Hemel Hempstead.
7. Pruitt K D, Tatusova T and Maglott D R (2007) NCBI reference sequences (RefSeq): a curated non-redundant sequence database of genomes, transcripts and proteins. *Nucleic Acids Research* 35, D61-D65.
8. Saitou N, Nei M. (1987). The Neighbor-joining Method: A New Method for Reconstructing Phylogenetic Trees. *Molecular Biology and Evolution.* 4:406-425.
9. Stanke M, Keller O, Gunduz I, Hayes A, Waack S and Morgerstern B (2006) AUGUSTUS: ab initio prediction of alternative transcripts. *Nucleic Acids Research* 34, W435-W439.
10. Tamura K, Dudley J, Nei M. and Kumar S. (2007) MEGA4: Molecular Evolutionary Genetics Analysis (MEGA) software version 4.0. *Molecular Biology and Evolution.* 24:1596-1599.
11. van Zijll de Jong E, Guthridge K M, Spangenberg G C and Forster J W (2003). Development and characterization of EST-derived simple sequence repeats (SSR) for pasture grass endophytes. *Genome.* 46:277-290.

12. White T J, Bruns T Lee S, and Taylor J. 1990. Amplification and direct sequencing of fungal ribosomal RNA genes for phylogenetics, p. 315-322. In M. A. Innis, D. H. Gelfand, J. J. Sninsky, and T. J. White (ed.), PCR protocols: a guide to methods and applications. Academic Press, Inc., New York, N.Y.

The invention claimed is:

1. A genetic construct including a nucleic acid encoding a terpene synthase, said terpene synthase-encoding nucleic acid including a nucleic acid sequence selected from the group consisting of SEQ ID NOS: 11 to 18 and functionally active terpene synthase-encoding variants thereof having at least 90% identity to one of SEQ ID NOS: 11 to 18.

2. The genetic construct according to claim 1, wherein said functionally active variants have at least 95% identity to one of SEQ ID NOS: 11 to 18.

3. The genetic construct according to claim 1, wherein said functionally active variants have at least 98% identity to one of SEQ ID NOS: 11 to 18.

4. A genetic construct including a nucleic acid encoding a terpene synthase, wherein said terpene synthase-encoding nucleic acid includes a nucleic acid sequence selected from the group consisting of SEQ ID NOS: 11 to 18.

5. The genetic construct according to claim 4, wherein said terpene synthase encoding nucleic acid includes the nucleic acid sequence of SEQ ID NO: 14.

6. A fungus transformed with the genetic construct according to claim 1.

7. The fungus according to claim 6, wherein said fungus is selected from the group consisting of *Nodulisporiumi* spp. and *Ascocoryne* spp.

8. The fungus according to claim 6, wherein said fungus consists of a *Nodulisporiumi* spp. that produces at least one volatile terpenoid compound when grown in potato dextrose culture medium.

9. The fungus according to claim 6, wherein said fungus consists of an *Ascocoryne* spp. that produces at least organic compound that is liquid at room temperature when grown in potato dextrose culture medium.

10. The fungus according to claim 7, wherein said fungus is selected from the group consisting of Dandenong Ranges isolate 1, Yana Ranges isolates 7, 10, 11, 12, 13 and 15 and Otway Ranges isolates 1, 3, 4 and 5.

11. A plant inoculated with the fungus according to claim 6, said plant comprising a fungus-free host plant stably infected with said fungus.

12. A method of producing an organic compound, said method including growing the fungus according to claim 6 in a culture medium under conditions suitable to produce said organic compound, and recovering the organic compound produced by the fungus.

13. The method according to claim 12, wherein said culture medium includes a source of carbohydrates, and wherein said fungus is grown under aerobic or anaerobic conditions.

14. The method according to claim 13, wherein said culture medium includes potato dextrose.

15. The method according to claim 12, wherein said organic compound is recovered from fungal cells, from the culture medium, or from air space associated with the culture medium or fungus.

16. The method according to claim 12, wherein said organic compound is a terpene selected from the group consisting of monoterpenes and sesquiterpenes.

17. The method according to claim 16, wherein said organic compound is selected from the group consisting of α-Thujene, β-Sabinene, β-Myrcene, α-Phellendrene, α-Terpinene, p-Cymene, (R)-(+)-Limonene, Eucalyptol, α-Ocimene, β-Ocimene, γ-Terpinene, α-Terpinolene, Allo-Ocimene, (−)-Terpinen-4-ol, α-Terpineol, 2H-pyran,tetrahydro-2-(propan-2-ylidene)-5-methoxy, 2H-pyran,tetrahydro-2-isopropyl-5-methoxy, 3-Cyclohexene-1-acetaldehyde,4-methyl-α-methylene-, 1-Cyclohexene-1-carboxaldehyde,4-(1-methylethenyl)-, p-Mentha-1,4(8)-dien-3-one (isomers), Bicyclo[2.2.2]octan-1-ol,4-ethyl, β-Elemene, α-Guajene, Bicyclo[5.3.0]decane,2 methylene-5-(1-methylvinyl)-8-methyl and 6-Guaijene, and derivatives and salts thereof.

* * * * *

UNITED STATES PATENT AND TRADEMARK OFFICE
CERTIFICATE OF CORRECTION

PATENT NO.       : 9,222,096 B2
APPLICATION NO.  : 14/119247
DATED            : December 29, 2015
INVENTOR(S)      : Spangenberg et al.

Page 1 of 1

It is certified that error appears in the above-identified patent and that said Letters Patent is hereby corrected as shown below:

In the Claims:

Column 58, lines 61 - 64, Claim 10 should read: -- The fungus according to claim 7, wherein said fungus is selected from the group consisting of Dandenong Ranges isolate 1, Yarra Ranges isolates 7, 10, 11, 12, 13 and 15 and Otway Ranges isolates 1, 3, 4 and 5. --

Signed and Sealed this
Twenty-third Day of August, 2016

Michelle K. Lee
*Director of the United States Patent and Trademark Office*

```
                              SEQUENCE LISTING

<160> NUMBER OF SEQ ID NOS: 26

<210> SEQ ID NO 1
<211> LENGTH: 291
<212> TYPE: PRT
<213> ORGANISM: Nodulisporium

<400> SEQUENCE: 1

Trp Ala Pro Leu Ile His Pro Leu Ser Glu Arg Val Thr Arg Glu Val
1               5                   10                  15

Asp Ser Tyr Phe Leu Gln His Trp Pro Phe Pro Asp Glu Lys Ser Arg
            20                  25                  30

Lys Lys Phe Val Ala Ala Gly Phe Ser Arg Val Thr Cys Phe Tyr Phe
        35                  40                  45

Pro Lys Ala Leu Asn Asp Arg Ile His Phe Ala Cys Arg Leu Leu Thr
    50                  55                  60

Val Leu Phe Leu Ile Asp Asp Leu Leu Glu Tyr Met Ser Leu Glu Asp
65                  70                  75                  80

Gly Lys Ala Tyr Asn Glu Lys Leu Ile Pro Ile Ser Arg Gly Asp Val
                85                  90                  95

Leu Pro Asp Arg Ser Val Pro Val Glu Tyr Ile Thr Tyr Asp Leu Trp
            100                 105                 110

Glu Ser Met Arg Ala His Asp Arg Val Met Ala Asp Asp Ile Leu Glu
        115                 120                 125

Pro Val Phe Thr Phe Gln Arg Ala Gln Thr Asp Ser Val Arg Leu Glu
    130                 135                 140

Ala Met Asp Leu Gly Lys Tyr Leu Glu Tyr Arg Glu Lys Asp Val Gly
145                 150                 155                 160

Lys Ala Leu Leu Gly Ala Leu Met Arg Phe Ser Met Gly Leu Val Val
                165                 170                 175

Pro Pro Glu Asp Leu Ala Ile Ala Arg Gln Ile Asp Phe Asn Cys Ala
            180                 185                 190

Arg His Leu Ser Val Leu Asn Asp Ile Trp Ser Phe Glu Lys Glu Leu
        195                 200                 205

Leu Ala Ser Lys Asn Ala His Glu Glu Gly Val Leu Cys Ser Ala
    210                 215                 220

Val Ser Ile Leu Ala Glu Gln Val Gly Ile Ser Ile Asp Gly Ala Lys
225                 230                 235                 240

Arg Ile Leu Tyr Tyr Leu Cys Arg Glu Trp Glu His Arg His Glu Thr
                245                 250                 255

Leu Val Lys Glu Met Leu Gln Val Arg Asp Thr Pro Ala Leu Arg Ser
            260                 265                 270

Tyr Val Lys Gly Leu Glu Tyr Gln Met Ile Gly Asn Glu Ala Trp Ser
        275                 280                 285

Arg Thr Thr
    290

<210> SEQ ID NO 2
<211> LENGTH: 299
<212> TYPE: PRT
<213> ORGANISM: Artificial Sequence
<220> FEATURE:
<223> OTHER INFORMATION: type terpene synthase
```

<400> SEQUENCE: 2

Phe Pro Tyr Arg Leu Asn Pro Tyr Val Lys Glu Ala Gln Asp Glu Tyr
1               5                   10                  15

Leu Glu Trp Val Leu Glu Glu Met Leu Ile Pro Ser Glu Lys Ala Glu
            20                  25                  30

Lys Arg Phe Leu Ser Ala Asp Phe Gly Asp Leu Ala Ala Leu Phe Tyr
        35                  40                  45

Pro Asp Ala Asp Asp Glu Arg Leu Met Leu Ala Asp Leu Met Ala
    50                  55                  60

Trp Phe Leu Val Phe Asp Asp Leu Leu Asp Arg Asp Gln Lys Ser Pro
65                  70                  75                  80

Glu Asp Gly Glu Ala Gly Val Thr Arg Leu Leu Asp Ile Leu Arg Gly
                85                  90                  95

Asp Gly Leu Asp Ser Pro Asp Asp Ala Thr Pro Leu Glu Phe Gly Leu
            100                 105                 110

Ala Asp Gly Trp Arg Arg Thr Leu Ala Arg Met Ser Ala Glu Trp Phe
        115                 120                 125

Asn Arg Phe Ala His Tyr Thr Glu Asp Tyr Phe Asp Ala Tyr Ile Trp
130                 135                 140

Glu Gly Lys Asn Arg Leu Asn Gly His Val Pro Asp Val Ala Glu Tyr
145                 150                 155                 160

Leu Glu Met Arg Arg Phe Asn Ile Gly Ala Asp Pro Cys Leu Gly Leu
                165                 170                 175

Ser Glu Phe Ile Gly Gly Pro Glu Val Pro Ala Ala Val Arg Leu Asp
            180                 185                 190

Pro Val Met Arg Ala Leu Glu Ala Leu Ala Ser Asp Ala Ile Ala Leu
        195                 200                 205

Val Asn Asp Ile Tyr Ser Tyr Glu Lys Glu Ile Lys Ala Asn Gly Glu
210                 215                 220

Val His Asn Leu Val Lys Val Leu Ala Glu His Gly Leu Ser Glu
225                 230                 235                 240

Leu Leu Ala Ile Ser Val Val Arg Asp Met His Asn Glu Arg Ile Thr
                245                 250                 255

Gln Phe Glu Glu Leu Glu Ala Ser Lys Ile Leu Ser Gly Asp Leu Glu
            260                 265                 270

Glu Glu Ser Pro Ala Val Arg Ala Tyr Val Glu Gly Leu His Asn Trp
        275                 280                 285

Ile Ser Gly Asn Leu Asp Trp His Arg Thr Ser
    290                 295

<210> SEQ ID NO 3
<211> LENGTH: 339
<212> TYPE: PRT
<213> ORGANISM: Nodulisporium

<400> SEQUENCE: 3

Met Ser Val Ala Val Glu Thr Arg Thr Ala Pro Thr Val Thr Leu Ser
1               5                   10                  15

Thr Ser Lys Pro Leu Ile Lys Glu Thr Trp Lys Ile Pro Ala Ser Gly
            20                  25                  30

Trp Thr Pro Met Ile His Pro Arg Ala Glu Glu Val Ser Arg Glu Val
        35                  40                  45

Asp Asn Tyr Phe Leu Glu His Trp Asn Phe Pro Asp Asp Gly Ala Lys
    50                  55                  60

```
Ser Thr Phe Leu Lys Ala Gly Phe Ser Arg Val Thr Cys Leu Tyr Phe
 65                  70                  75                  80

Pro Leu Ala Lys Asp Asp Arg Ile His Phe Ala Cys Arg Leu Leu Thr
                 85                  90                  95

Val Leu Phe Leu Ile Asp Asp Ile Leu Glu Glu Met Ser Phe Ala Asp
                100                 105                 110

Gly Glu Ala Leu Asn Asn Arg Leu Ile Glu Leu Ser Lys Gly Pro Glu
                115                 120                 125

Tyr Ala Thr Pro Asp Arg Ser Ile Pro Ala Glu Tyr Val Ile Tyr Asp
        130                 135                 140

Leu Trp Glu Ser Met Arg Lys His Asp Leu Glu Leu Ala Asn Glu Val
145                 150                 155                 160

Leu Glu Pro Thr Phe Val Phe Met Arg Ser Gln Thr Asp Arg Val Arg
                165                 170                 175

Leu Ser Ile Lys Glu Leu Gly Glu Tyr Leu Arg Tyr Arg Glu Lys Asp
                180                 185                 190

Val Gly Lys Ala Leu Leu Ser Ala Leu Met Arg Tyr Ser Met Glu Leu
        195                 200                 205

Arg Pro Thr Ala Glu Glu Leu Ala Leu Lys Pro Leu Glu Glu Asn
210                 215                 220

Cys Ser Lys His Ile Ser Ile Val Asn Asp Ile Tyr Ser Phe Glu Lys
225                 230                 235                 240

Glu Val Ile Ala Ala Lys Thr Gly His Glu Glu Gly Ser Phe Leu Cys
                245                 250                 255

Ser Ala Val Lys Val Val Ala Thr Glu Thr Thr Leu Gly Ile Ser Ala
        260                 265                 270

Thr Lys Arg Val Leu Trp Ser Met Val Arg Gly Trp Glu Leu Val His
275                 280                 285

Asp Ala Met Cys Glu Ala Leu Leu Ala Ala Gly Thr Ser Ser Gln
        290                 295                 300

Thr Val Lys Asp Tyr Met Arg Gly Leu Gln Tyr Gln Met Ser Gly Asn
305                 310                 315                 320

Glu Leu Trp Ser Cys Thr Thr Pro Arg Tyr Ile Glu Ala Ile Asp Gln
                325                 330                 335

Ala Ala Arg

<210> SEQ ID NO 4
<211> LENGTH: 365
<212> TYPE: PRT
<213> ORGANISM: Nodulisporium

<400> SEQUENCE: 4

Met Ser Thr Asn Asn Gln Ala Asp Ile Gln Ala Leu Leu Ala Lys Cys
1               5                   10                  15

Val Gly Gln Lys Val Lys Ile Pro Asp Leu Phe Ala Leu Cys Pro Trp
                20                  25                  30

Asp Val Glu Ile Thr Pro Trp Asn Ala Lys Leu Glu Lys Glu Ile Glu
            35                  40                  45

Gln Trp Arg Ser Arg Trp Ile Ile Asp Pro Val Ser Leu Lys Arg Asn
        50                  55                  60

Arg Ile Val Asp Pro Gly Leu Phe Ala Arg Ala Gly Ala Pro Arg Ala
 65                  70                  75                  80

Ser Phe Asp Gly Gln Leu Ile Val Ala Leu Trp Ala Ala Trp Thr Phe
                 85                  90                  95
```

Tyr Trp Asp Asp Ala His Asp Phe Gly Glu Phe Asp Lys Pro Glu
            100                 105                 110

Glu Val Val Ala His Cys Ala Gln Thr Ile Glu Leu Phe Arg Gln Ser
            115                 120                 125

Leu Tyr Asn Glu Asn Pro Leu Ala Ile Asp Pro Ala Lys Ile Ser Pro
        130                 135                 140

Asp Tyr Leu Thr Val Gln Ser Val His Glu Trp Ala Ala Val Val Gly
145                 150                 155                 160

Glu Lys Cys Val Ser Pro Ser Leu Lys Asp Trp Leu Phe Lys Val Phe
                165                 170                 175

Ala Asp Thr Cys Ile Gly Ile Ser Arg Val Gln His Glu Phe Glu Ser
            180                 185                 190

Lys Thr Ile Leu Asp Leu Asp Thr Tyr Gln Lys Ile Arg Arg Asp Ser
        195                 200                 205

Ser Gly Ser Leu Thr Thr Leu Ala Cys Ile Leu Tyr Ala Asp Asn Val
    210                 215                 220

Ala Phe Pro Asp Trp Phe Asp His Glu Leu Val Leu Lys Ala Ala
225                 230                 235                 240

Asp Leu Thr Asp Ile Ile Ile Trp Val Val Asn Asp Ile Thr Ser Ala
                245                 250                 255

Arg His Glu Leu Gln Cys Lys His Ile Asp Asn Tyr Val Pro Leu Leu
            260                 265                 270

Val Tyr His Lys Gly Leu Thr Pro Gln Glu Ala Val Asp Glu Ala Gly
        275                 280                 285

Arg Val Ala His Gln Ala Tyr Leu Asp Phe Glu Ala Leu Glu Pro Gln
    290                 295                 300

Leu Phe Gln Leu Gly Asp Ser Arg Gly Cys Ala His Glu Met Gly Lys
305                 310                 315                 320

Phe Ile Asp Ser Cys Lys Phe Glu Cys Ser Gly Ile Ile Asn Trp His
                325                 330                 335

Tyr Glu Val Lys Arg Tyr Val Pro Trp Lys Pro Gly Met Asp Arg Asp
            340                 345                 350

Ser Leu Tyr Val Val Leu Gly Glu Asp Leu Pro Thr Glu
        355                 360                 365

<210> SEQ ID NO 5
<211> LENGTH: 293
<212> TYPE: PRT
<213> ORGANISM: Nodulisporium

<400> SEQUENCE: 5

Met Gln Gly Thr Arg Val Ala His Phe Gly Ala Ser Trp Trp Pro Tyr
1               5                   10                  15

Ala Ser Phe Glu Thr Leu Phe Ile Ala Thr Cys Leu Ser Leu Trp Leu
            20                  25                  30

Phe Ile Trp Asp Asp Glu Thr Asp Ser Leu Glu Phe Ser Asp Leu Ser
        35                  40                  45

Asn Asp Phe Glu Arg Ser Cys Met Phe Arg Arg Glu Thr Met Ala Tyr
    50                  55                  60

Ile Glu His Ser Leu Lys Ser Asp Asp Ser Glu Ile Leu Ser Gln Ile
65                  70                  75                  80

Ser Gly Asn Pro Ile Ile Thr Asn Phe Lys Glu Val Gly Glu Ala Ile
                85                  90                  95

Arg Ser Ser Cys Asn Glu Glu Gln Thr Ala Thr Phe Leu His Ala Leu

```
            100                 105                 110
Asp Phe Phe Val Lys Met Cys Glu Glu Glu Gln His Leu Gln Leu Ser
            115                 120                 125

Gln Gly Leu Pro Thr Ile Asp Gln Tyr Ile Lys Arg Arg Met Gly Ser
            130                 135                 140

Ser Gly Val Glu Val Cys Leu Ala Ile Gln Glu Tyr Cys Phe Gly Met
145                 150                 155                 160

Thr Ile Pro Ser Glu Tyr Met Gln Cys Glu Pro Met Lys Thr Ile Trp
                    165                 170                 175

His Glu Thr Asn Leu Ile Ile Ala Thr Met Asn Asp Met Met Ser Ile
                180                 185                 190

Lys Lys Glu Val Asp Asn Ser Gln Val Asp Thr Leu Val Pro Leu Leu
            195                 200                 205

Phe Val Gln Leu Gly Ser Val Gln Glu Ala Ile Asp Lys Val Ala Glu
            210                 215                 220

Met Thr Arg Ser Ala Val Gln Arg Phe Glu Asp Ala Glu Arg Asp Ile
225                 230                 235                 240

Lys Thr Leu Tyr Ala Ser Asn Pro Glu Leu Leu Ser Asp Leu Thr Lys
                245                 250                 255

Phe Ile Asp Gly Cys Lys His Ala Cys Thr Gly Asn Met Thr Trp Ser
                260                 265                 270

Leu Thr Ser Gly Arg Tyr Lys Leu Ser Thr Pro Asp Ser Asp Gly Phe
            275                 280                 285

Ile Arg Ile Lys Leu
            290

<210> SEQ ID NO 6
<211> LENGTH: 541
<212> TYPE: PRT
<213> ORGANISM: Nodulisporium

<400> SEQUENCE: 6

Met Ser Leu Pro Ile Pro Thr Glu Gly Asn Ala Leu Arg Asp Ala Pro
1               5                   10                  15

Phe Ser Gly Val Thr Glu Lys Glu Arg Asp Tyr Val Thr Glu Thr Gly
            20                  25                  30

Leu Ala Gly Trp Gln Asp Thr Gln Asp Ala Arg Asn Ala Tyr Gln Trp
        35                  40                  45

Ile Leu Thr Glu Glu Asn Cys Glu Ser Ser Val Arg Ser Ser Glu
    50                  55                  60

Asp Ser Val Leu Glu Asn Asn Ala Glu Thr Leu Ala Ser Leu Gly Glu
65                  70                  75                  80

His Leu Arg Asp Asp Ser Glu Ala Lys Leu Gly Thr Ser Ser Asn Pro
                85                  90                  95

Thr Ser Ile Arg Val Gln Gln Thr Thr Thr Met Ala Leu Ser Lys Asp
            100                 105                 110

Gln Lys Thr Ser Ser Arg Val Leu Val Ala Tyr Leu Arg Tyr Thr Ala
            115                 120                 125

Leu Ala Tyr Gln Thr Ile His Thr Pro Leu Thr Gly Val Leu Glu Gln
        130                 135                 140

Val Ala Glu Val Gly Ala Asp Ala Ile Pro Arg His Gln His Leu Pro
145                 150                 155                 160

Thr Lys Phe Asn Met Pro Leu Asp Ile Arg Pro Thr Thr Cys Ala Phe
                165                 170                 175
```

```
Asp Pro Val Gly Ile Ser Phe Ser Ser Asp Thr Ala Lys Gln Glu Ser
            180                 185                 190

Phe Glu Phe Leu Arg Glu Ala Ile Ser Gln Thr Ile Pro Gly Leu Glu
        195                 200                 205

Asn Cys Asn Val Phe Asp Pro Arg Ser Val Gly Val Pro Trp Pro Thr
    210                 215                 220

Ser Leu Pro Gly Ala Ala Gln Ser Lys Tyr Trp Arg Asp Cys Glu Glu
225                 230                 235                 240

Ala Val Glu Asp Leu Met Asn Ala Ile Gly Ala Lys Pro Gly Glu
            245                 250                 255

Gln Gly Ser Leu Pro Ala Glu Met Ala Ser Val Gly Leu Lys Ala Ala
            260                 265                 270

Lys Arg Lys Glu Leu Phe Asp Thr Ser Val Thr Ala Pro Met Asn Met
        275                 280                 285

Phe Pro Ala Ala Asn Gly Pro Arg Ala Arg Ile Met Gly Lys Ala Asn
        290                 295                 300

Leu Leu Ile Phe Met His Asp Val Ile Glu Ser Glu Thr Val Glu
305                 310                 315                 320

Ile Pro Thr Ile Ile Asp Ser Ala Leu Ala Asp Thr Val Gly Asp Val
            325                 330                 335

Lys Gly Ala Asp Ile Leu Trp Lys Asn Thr Ile Phe Lys Glu Tyr Ala
            340                 345                 350

Glu Glu Thr Ile Lys Val Asp Pro Val Val Gly Pro Val Phe Leu Lys
        355                 360                 365

Gly Ile Leu Asn Trp Val Gln His Thr Arg Asp Lys Leu Pro Gly Ser
370                 375                 380

Met Thr Phe Asn Ser Leu Asn Glu Tyr Ile Asp Tyr Arg Ile Gly Asp
385                 390                 395                 400

Phe Ala Val Asp Phe Cys Asp Ala Ala Ile Met Leu Thr Cys Glu Ile
            405                 410                 415

Phe Leu Thr Pro Ala Asp Met Glu Pro Leu Arg Lys Leu His Arg Leu
        420                 425                 430

Tyr Met Thr His Phe Ser Leu Thr Asn Asp Leu Tyr Ser Tyr Asn Lys
        435                 440                 445

Glu Leu Trp Ala Phe Glu Gln Asn Gly Ser Ala Leu Val Asn Ala Val
450                 455                 460

Arg Val Leu Glu Leu Leu Asp Thr Ser Pro Arg Gly Ala Lys Val
465                 470                 475                 480

Ile Leu Arg Ala Phe Leu Trp Asp Leu Glu Leu Gln Val Asn Glu Glu
            485                 490                 495

Leu Thr Lys Leu Ser Gln Ser Asn Leu Thr Pro Ala Gln Trp Arg Phe
        500                 505                 510

Ala Arg Gly Met Val Glu Val Leu Ala Gly Asn Thr Tyr Tyr Ser Ala
        515                 520                 525

Thr Cys Leu Arg Tyr Ala Lys Pro Gly Leu Arg Gly Val
530                 535                 540

<210> SEQ ID NO 7
<211> LENGTH: 373
<212> TYPE: PRT
<213> ORGANISM: Nodulisporium

<400> SEQUENCE: 7

Met Ala Pro Asp Ile Asp Gln Ile Trp Pro Ser Thr Leu Asp Val Pro
1               5                   10                  15
```

Ala Ser Ala Ile Asp Glu Arg Lys Ala Leu Val Asn Arg Ala Leu Asn
        20                  25                  30

Gln Lys Ile Leu Val Pro Asn Ile Leu Ser Leu Met Pro Ala Trp Ile
            35                  40                  45

Ser Glu Leu Gln Pro Asp Ile Asp Glu Ile Asn Lys Glu Ile Asp Glu
 50                  55                  60

Trp Leu Leu Ile Val Asn Val Ala Gly Ala Lys Lys Ala Lys His Arg
 65                  70                  75                  80

Ala Arg Gly Asn Tyr Thr Phe Leu Thr Ala Val Tyr Pro His Cys
                85                  90                  95

Lys Lys Asp Lys Met Leu Thr Leu Ser Lys Phe Leu Tyr Trp Ile Phe
            100                 105                 110

Phe Trp Asp Asp Glu Ile Asp Asn Gly Gly Glu Leu Thr Glu Asp Glu
        115                 120                 125

Glu Gly Thr Gln Gln Cys Cys Asp Glu Thr Asn Lys Cys Ile Asp Asp
130                 135                 140

Cys Leu Gly Pro Asn Pro Asn Tyr Thr Pro Pro Asn Ser Arg Gly
145                 150                 155                 160

Thr Val Glu Met Phe Tyr Pro Ile Leu Arg Asp Leu Arg Ala Gly Leu
                165                 170                 175

Gly Pro Ile Ser Thr Glu Arg Leu Arg Leu Glu Leu His Asp Tyr Val
            180                 185                 190

Asn Gly Val Gly Arg Gln Gln Lys Val Arg Gln Gly Asp Arg Leu Pro
        195                 200                 205

Asp Pro Trp Tyr His Phe Gln Ile Arg Ser Asp Val Gly Val Ile
210                 215                 220

Pro Ser Ile Thr Gln Asn Glu Tyr Ala Met Glu Phe Glu Leu Pro Glu
225                 230                 235                 240

His Val Arg Arg His Glu Ala Met Glu Phe Ile Val Leu Glu Cys Thr
                245                 250                 255

Lys Leu Thr Ile Leu Leu Asn Asp Val Leu Ser Leu Gln Lys Glu Phe
            260                 265                 270

Arg Val Ser Gln Leu Glu Asn Leu Val Leu Phe Met Asn Lys Tyr
        275                 280                 285

Asp Leu Thr Leu Gln Ala Ala Ile Asp Lys Ile Leu Asp Leu Ile Arg
290                 295                 300

Glu His Tyr Ala Ile Cys Val Ala Ala Glu Glu Arg Leu Pro Trp Ser
305                 310                 315                 320

Lys Asp Asp Glu Lys Leu Asn Lys Asp Ile Arg Glu Tyr Val Arg Gly
                325                 330                 335

Cys Gln Arg Leu Ala Thr Gly Thr Ala Tyr Trp Ser Tyr Ser Cys Glu
            340                 345                 350

Arg Tyr Phe Lys Gln Thr Gln Leu Asn Asp Lys Trp Glu Val Leu Leu
        355                 360                 365

Asp Leu Ser Tyr Glu
    370

<210> SEQ ID NO 8
<211> LENGTH: 348
<212> TYPE: PRT
<213> ORGANISM: Nodulisporium

<400> SEQUENCE: 8

Met Asn Phe Ser Phe Lys Ile Thr Leu Lys Lys Pro Thr Phe Ser Gly

```
              1               5                  10                 15
            Leu Gln Ser Phe Phe Pro Arg His Lys Pro Ser Ile Ser Gln Ser Ser
                            20                 25                 30

Ser Ser Ser Thr Ser Ser Thr Ser Ser Ile Lys Leu Glu Thr Thr Ser
                            35                 40                 45

Thr Pro Gln Cys Ile Thr Thr Phe Pro Val Tyr Val His Arg Asp Glu
                50                     55                     60

Ala Gln Ile Ser Gln Gly Ala Leu Asp Ala Arg Ser Asn Phe Gln His
             65                 70                 75                 80

Leu Leu Pro Asp Ala Glu Tyr Arg Pro His Ser Ala Gly Pro His Gly
                            85                 90                 95

Asn Phe Phe Ala Ile Cys Trp Pro Asp Ser Lys Met Glu Arg Ala Lys
                           100                105                110

Leu Ala Thr Glu Ile Ile Glu Thr Leu Trp Leu Tyr Asp Asp Val Ile
                           115                120                125

Glu Asp Ile Pro His Thr Gly Ala Leu Glu Ala His Ala Ser Val Arg
                130                135                140

Asp Ser Leu Val Gly Lys Pro Glu Lys Thr Gln Ser Lys Gly Arg Ile
            145                150                155                160

Ala Thr Leu Phe Lys Thr Phe Gly Glu Arg Val Ser Gln Met Asp Lys
                           165                170                175

Asp Gly Ala Pro Arg Val Ile Gly Ser Leu Lys Ser Tyr Leu Asp Asn
                           180                185                190

Tyr Asp Ser Gln Lys Thr Pro Phe Ser Thr Ile Ala Glu Tyr Thr Glu
                           195                200                205

Phe Arg Ile Val Asn Val Gly Phe Gly Ile Met Glu Ser Phe Met Gln
                210                215                220

Trp Thr Leu Gly Ile His Leu Asp Glu Asp Thr Glu Leu Ser Arg
            225                230                235                240

Asp Tyr Tyr Ser Ser Cys Gly Arg Val Met Gly Leu Thr Asn Asp Leu
                           245                250                255

Tyr Ser Trp Lys Val Glu Arg Ile Glu Pro Gly Asp Arg Gln Trp Asn
                           260                265                270

Ala Val Pro Ile Ile Met Lys Gln Tyr Asn Ile Arg Glu Lys Asp Ala
                           275                280                285

Thr Val Phe Leu Arg Gly Leu Ile Met Tyr His Glu Gln Glu Thr Arg
                           290                295                300

Arg Leu Gly Leu Glu Leu Leu Arg Lys Thr Gly Glu Ser Pro Lys Met
            305                310                315                320

Ile Gln Tyr Val Gly Ala Met Gly Leu Met Leu Gly Gly Asn Cys Tyr
                           325                330                335

Trp Ser Ser Thr Cys Pro Arg Tyr Asn Pro Glu Pro
                           340                345

<210> SEQ ID NO 9
<211> LENGTH: 310
<212> TYPE: PRT
<213> ORGANISM: Nodulisporium

<400> SEQUENCE: 9

Met Ser Leu Ala Ser Ser Phe Gly Asp Tyr Pro Ser Ser His Trp Ala
 1               5                  10                 15

Pro Leu Ile His Pro Leu Ser Glu Arg Val Thr Arg Glu Val Asp Ser
                20                 25                 30
```

```
Tyr Phe Leu Gln His Trp Pro Phe Pro Asp Glu Lys Ser Arg Lys Lys
                 35                  40                  45

Phe Val Ala Ala Gly Phe Ser Arg Val Thr Cys Phe Tyr Phe Pro Lys
 50                  55                  60

Ala Leu Asn Asp Arg Ile His Phe Ala Cys Arg Leu Leu Thr Val Leu
 65                  70                  75                  80

Phe Leu Ile Asp Asp Leu Leu Glu Tyr Met Ser Leu Glu Asp Gly Lys
                 85                  90                  95

Ala Tyr Asn Glu Lys Leu Ile Pro Ile Ser Arg Gly Asp Val Leu Pro
                100                 105                 110

Asp Arg Ser Val Pro Val Glu Tyr Ile Thr Tyr Asp Leu Trp Glu Ser
                115                 120                 125

Met Arg Ala His Asp Arg Val Met Ala Asp Ile Leu Glu Pro Val
        130                 135                 140

Phe Thr Phe Gln Arg Ala Gln Thr Asp Ser Val Arg Leu Glu Ala Met
145                 150                 155                 160

Asp Leu Gly Lys Tyr Leu Glu Tyr Arg Glu Lys Asp Val Gly Lys Ala
                165                 170                 175

Leu Leu Gly Ala Leu Met Arg Phe Ser Met Gly Leu Val Val Pro Pro
                180                 185                 190

Glu Asp Leu Ala Ile Ala Arg Gln Ile Asp Phe Asn Cys Ala Arg His
                195                 200                 205

Leu Ser Val Leu Asn Asp Ile Trp Ser Phe Glu Lys Glu Leu Leu Ala
        210                 215                 220

Ser Lys Asn Ala His Glu Glu Gly Val Leu Cys Ser Ala Val Ser
225                 230                 235                 240

Ile Leu Ala Glu Gln Val Gly Ile Ser Ile Asp Gly Ala Lys Arg Ile
                245                 250                 255

Leu Tyr Tyr Leu Cys Arg Glu Trp Glu His Arg His Glu Thr Leu Val
                260                 265                 270

Lys Glu Met Leu Gln Val Arg Asp Thr Pro Ala Leu Arg Ser Tyr Val
                275                 280                 285

Lys Gly Leu Glu Tyr Gln Met Ile Gly Asn Glu Ala Trp Ser Arg Thr
                290                 295                 300

Thr Leu Arg Tyr Leu Ala
305                 310

<210> SEQ ID NO 10
<211> LENGTH: 417
<212> TYPE: PRT
<213> ORGANISM: Nodulisporium

<400> SEQUENCE: 10

Met Ala Arg Pro Lys Arg Ile Thr Thr Thr Leu Leu Ser Leu Ala Arg
  1               5                  10                  15

Arg Thr Gln Ser Lys Ile Ser Ser Ile Leu Phe Pro Ser Pro Leu Pro
                 20                  25                  30

Ala Glu Gly Ser Ser Gly Ala Val Val Gln Tyr Ala Pro Glu Lys Lys
                 35                  40                  45

Pro Gly Ala Gln Gln Gly Leu Cys Gly Glu Ala Leu Val Leu Ala Ser
 50                  55                  60

Gln Leu Asp Gly Gln Thr Phe Arg Leu Pro Asp Leu Trp Lys Val Leu
 65                  70                  75                  80

Ala Asp Trp Pro Leu Ala Ala Asn Pro His Ala Glu Arg Leu Glu Gly
                 85                  90                  95
```

Leu Val Asn Ser Ile Leu Glu Arg His Ile Thr Ser Glu Lys Lys Leu
                100                 105                 110

Arg Ala Leu Lys Gln Ala Asn Phe Ala Arg Leu Ile Ser Leu Trp Tyr
            115                 120                 125

Pro Asp Ala Glu Trp Pro Glu Leu Glu Ala Ala Thr Ala Tyr Ser Val
130                 135                 140

Trp Ile Phe Val Trp Asp Asp Glu Val Asp Ala Gly Asp Thr Asp Val
145                 150                 155                 160

Ser Leu Asp Glu Glu Leu Ser Arg Ala Tyr Tyr Lys Lys Ser Leu Ser
                165                 170                 175

Thr Ile His Arg Leu Leu Gly Leu Asp Asp Ala Gly Asp Asp Gln
            180                 185                 190

Gly Gly Ser Glu Glu Glu Glu Thr Leu His Pro Asn Met Val Leu Phe
                195                 200                 205

Gly Asp Ala Ala Arg Ser Leu Arg Ser Ser Thr Asp Lys Ile Gln Arg
210                 215                 220

Glu Arg Phe Tyr Arg Glu Met Glu Asn Phe Met Ile Gln Val Gly Val
225                 230                 235                 240

Glu His Ser His Arg Met Arg Gly Ser Ile Pro Thr Val Asp Lys Tyr
                245                 250                 255

Met Glu Ile Arg Ser Gly Ser Val Gly Cys Ala Pro Gln Ile Ala Ile
            260                 265                 270

Thr Asp Phe Met Leu Lys Ile Arg Leu Pro Glu Ser Ile Met Glu Ser
            275                 280                 285

Ala Ala Met Lys Ala Leu Trp Arg Glu Thr Val Val Ile Cys Leu Ile
            290                 295                 300

Leu Asn Asp Val Tyr Ser Val Gln Lys Glu Ile Ala Gln Gly Ser Leu
305                 310                 315                 320

Leu Asn Leu Val Pro Val Ile Phe Lys Asn Cys Ile Pro Glu Lys Gln
                325                 330                 335

Asn Leu Asp Thr Val Thr Ala Asp Val Glu Val Ala Leu Gln Gly Ser
            340                 345                 350

Ile Arg Gly Phe Glu Asp Ala Ala Ala Ser Leu Gly Gln Met Val Ala
            355                 360                 365

Asp Asp Ala Gln Leu Asp Lys Asp Val Gln Ser Phe Ile Arg Trp Cys
370                 375                 380

Arg Tyr Phe Ile Thr Gly Val Gln Gln Trp Ser Ile Glu Ser Ala Arg
385                 390                 395                 400

Tyr Gly Met Ala Glu Cys Leu Gln Glu Asp Gly Ser Leu Ser Ile Val
                405                 410                 415

Leu

<210> SEQ ID NO 11
<211> LENGTH: 1017
<212> TYPE: DNA
<213> ORGANISM: Nodulisporium

<400> SEQUENCE: 11
atgtctgtcg cagtagaaac ccgcacggcc cccaccgtta ctctaagcac ttctaagccc    60
cttatcaagg agacttggaa gatccccgcc tctggctgga cgcccatgat ccaccctaga   120
gctgaggagg tctctcgtga ggtagacaac tacttcctcg agcactggaa cttccccgac   180
gacggcgcca aatctacttt cctcaaggcg ggcttctctc gtgttacttg cctttacttc   240

```
cctctagcca aggatgacag aatacacttt gcctgccgtc tccttaccgt cctgttcttg      300
attgatgata ttctcgagga gatgtccttc gctgatggcg aggccctcaa caacagactg      360
attgaactct ccaagggtcc cgagtatgcc accctgacc ggtccatccc ggccgagtat       420
gtcatctacg acctgtggga gagcatgcgc aagcacgatc tcgagctcgc caatgaggtt      480
ctcgagccca cctttgtctt catgcgctcg caaaccgacc gtgtccgact gagcatcaag      540
gagctcggcg agtacctgcg atatcgtgag aaggatgtcg gcaaggctct tctatcagcc      600
ctcatgcgct actccatgga attgcgcccc acggcggaag agctggcagc gctcaagccc      660
ctagaagaga actgctccaa gcacatctcc atcgtcaacg acatctacag cttcgagaag      720
gaagtgatcg cggccaagac gggccacgag gagggatcct tcctatgctc tgccgtcaag      780
gtcgtcgcga cggagacgac gctaggcatc tcagcgcacca aacgcgtgct gtggtccatg     840
gtgcgcgagt gggagctcgt ccacgacgcc atgtgcgagg ccctcctcgc cgccgccggc      900
accagcagcc agaccgtcaa ggactacatg cgcggcctgc agtaccagat gagcggaaac      960
gagctgtgga gctgcacgac cccgcgctac atcgaggcta tcgaccaggc cgcccga        1017
```

<210> SEQ ID NO 12
<211> LENGTH: 1095
<212> TYPE: DNA
<213> ORGANISM: Nodulisporium

<400> SEQUENCE: 12

```
atgtctacaa ataaccaagc cgacatccag gcacttctcg ccaagtgtgt aggccaaaag      60
gtcaagattc cggatctctt cgccctgtgt ccgtgggatg tggagataac cccttggaat     120
gcaaagctgg agaaggaaat agagcagtgg cgatcgagat ggattataga cccggtaagc     180
ctcaagcgta accgtatcgt cgatccgggt ctattcgcga gagccggtgc tccgagggct     240
tcttttgatg gccagttgat tgttgctttg tgggctgctt ggaccttcta ctgggacgat     300
gctcacgatt tcggcgaatt tgacgacaag cccgaggaag tagtcgctca ttgcgcacag     360
acaattgagc tcttccgcca gagtctgtac aatgagaacc cattggctat cgaccccgcc     420
aagatctctc ccgactacct taccgtccag tcagtccacg agtgggcagc agtggtggga     480
gaaaagtgtg tttcgccctc cttgaaggac tggctcttca aggtcttcgc agacacttgt     540
atagggattt cccgagtcca acacgagttc gagagtaaaa cgatactaga tcttgatacg     600
tatcagaaga tacgcaggga ctcgagcggt tcattgacca ctctggcatg cattctatac      660
gccgataatg ttgctttccc agattggttc ttcgaccacg aactcgttct aaaagccgcg      720
gatctaactg atatcattat ctgggttgtc aacgatatta cgtctgcacg acacgaactc      780
caatgcaagc acatcgacaa ctacgtaccg ctcctagtct accacaaggg tcttacgccg      840
caagaagccg tcgatgaggc aggcagggtt gcgcaccaag cctacctaga cttcgaggcg      900
ctggaaccgc aactctttca gcttggggac agccgcggct gcgctcacga gatggggaag      960
tttatcgata gttgtaaatt tgagtgttcg ggtattatta ctggcactta cgaggttaag     1020
cgctatgttc cttggaagcc tggtatggat cgtgatagcc tgtatgttgt gttgggtgaa     1080
gatctaccaa ctgag                                                      1095
```

<210> SEQ ID NO 13
<211> LENGTH: 879
<212> TYPE: DNA
<213> ORGANISM: Nodulisporium

<400> SEQUENCE: 13

```
atgcaaggta ccagggtagc ccattttggt gcttcttggt ggccctacgc atcgttcgag    60
acactgttca ttgcgacgtg cctttcactt tggctcttca tctgggacga cgaaactgac   120
tcactcgaat tctccgacct cagtaacgac tttgaacgat catgcatgtt tagaagagag   180
acaatggcat acatagagca cagtcttaaa tctgatgact ctgagatact ctctcagata   240
tcaggcaacc ccatcattac taacttcaaa gaggttgggg aagcaatcag atcgtcatgc   300
aatgaagaac agaccgccac cttcttacac gctttggatt tcttcgtgaa atgtgtgag    360 gaggagcagc acctgcagct aagccaaggg ctaccgacaa tcgaccaata tattaagcgc   420
cgaatgggat ctagtggggt ggaagtttgc ctggccattc aggaatactg cttcggcatg   480
acaattccga gtgaatacat gcaatgcgag ccgatgaaga cgatttggca tgagaccaac   540
ctaataattg ctacaatgaa cgatatgatg tctatcaaga aagaggttga taattcacaa   600
gttgatactc tggtcccact gctcttcgtc cagcttggtt cggtccagga ggccattgac   660
aaggttgcag agatgacaag atctgctgtc cagcgctttg aggacgctga gagagacata   720
aagacacttt atgcttccaa tccagaactc ctaagtgacc tcaccaaatt catcgatggg   780
tgtaagcatg cctgtacggg aaacatgact tggagcttga cttccggtcg gtacaagcta   840
agtaccccag attctgatgg cttcatcagg ataaaatta                          879
```

<210> SEQ ID NO 14
<211> LENGTH: 1623
<212> TYPE: DNA
<213> ORGANISM: Nodulisporium

<400> SEQUENCE: 14

```
atgtcgttgc cgataccgac agaaggaaac gctctaaggg acgcgccatt ttcgggtgtc    60
accgagaagg agagagatta tgtaaccgag acagggcttg caggctggca ggatacgcaa   120
gatgcgagaa atgcgtatca gtggatcctc acggaagaaa actgcgagtc tagtgacgtg   180
aggtcaagcg aggactctgt gctggaaaat aacgccgaaa cttttggcgag cttgggtgaa   240 catcttcgcg atgattccga ggctaagcta ggtacgtctt cgaaccccac gtccattcgt   300
gtccagcaaa caaccacgat ggctttgtct aaggaccaaa agaccagtag cagggtccta   360
gtagcatacc tgcgttacac tgcttttagcc taccagacta tacatacgcc gctgacgggc   420
gttctcgaac aagttgccga agtaggtgca gacgcaatac ctagacatca acaccttcca   480
acaaagttca acatgccact agatatccga cccacaacct gcgcgttcga tcccgttggg   540
atctcattca gctcagacac tgccaagcaa gagagcttcg agttcctaag agaggccatc   600
tctcagacca taccaggact cgagaactgc aatgtcttcg atccgcgctc tgtgggagta   660
ccatggccaa cctcgctgcc cggcgcagcc cagagcaagt attggagaga ctgcgaagaa   720
gcagtagaag atctgatgaa cgcaatcgtc ggcgcgaagc caggcgagca gggctccctg   780
ccagcagaga tggccagtgt aggcttgaag gcagcgaaac gaaaggaact cttcgataca   840
tctgtcaccg ccccgatgaa catgtttccc gcagcgaacg gtccacgagc gaggataatg   900
ggtaaagcaa acttgcttat ctttatgcat gatgatgtta ttgaatccga gacggtcgag   960
ataccaacca taattgactc cgccctcgcc gacacagttg gcgacgtcaa aggtgcagat  1020
atactctgga gaacaccat cttcaaagaa tatgcggagg agaccatcaa ggtagaccct  1080
gttgtcggac cggtcttctt gaaaggcata ctgaactggg tacaacacac gcgtgacaag  1140
ctgcccggct ctatgacatt caattctcta aatgaataca tcgattaccg aatcggggat  1200
```

```
ttcgctgtcg acttctgcga cgcagccatc atgttgacat gtgaaatctt tctaacaccg    1260
gccgacatgg agcctctcag gaagcttcac agactttaca tgactcactt ctcgttgacg    1320
aacgacctct attcttataa caaagaactc tgggcctttg agcaaaacgg ctctgcgctc    1380
gtgaacgccg tccgagttct ggagctgctc ctggacacct cccctcgagg agcgaaggtt    1440
atccttcgag ctttcctgtg ggacctcgag ctccaggtca atgaagaact cacaaaactc    1500
tcccagagca acctaacacc agcccagtgg cgcttcgcac ggggcatggt cgaggtgctt    1560
gcgggaaaca catactactc cgcgacttgt ctacgatacg cgaagccggg attgcgagga    1620
gtc                                                                  1623

<210> SEQ ID NO 15
<211> LENGTH: 1119
<212> TYPE: DNA
<213> ORGANISM: Nodulisporium

<400> SEQUENCE: 15
atggcacccg acatagatca gatctggcca tctacattgg atgtgccagc cagcgccatc      60
gatgaacgca aagccctggt taatagagcg ttgaaccaaa agattctagt cccgaacatc     120
ctgtctttaa tgccagcatg gatcagcgag ttgcaaccgg acattgatga aatcaataag     180
gaaatagacg agtggcttct aatcgtcaat gtggccgggg ctaagaaagc gaaacatcga     240
gctcgtggaa attacacatt tcttacggct gtttactatc ctcattgtaa gaaggataag     300
atgcttaccc tgtcgaagtt tctttactgg atattcttct gggatgatga atcgacaac      360 ggtggagaac tgaccgagga cgaggagggc acacaacaat gctgtgatga gacaaacaaa     420
tgcattgacg actgtctcgg gcctaaccc aactacacgc cccctccaaa ctcgcgaggg      480
acagtcgaga tgttctaccc gattctacga gatcttcgag caggcctcgg cccaatctca     540
acagaacggc ttcgtctcga gctccacgac tacgtgaacg gagtaggaag acagcagaag     600
gttcgccaag gagatcgcct gccggatccg tggtatcact tccagattcg atctgacgat     660
gtcggtgtca tccccagtat cacacagaat gaatacgcca tggaattcga gctcccggag     720
catgtccgca gacatgaggc catggagttc attgttctgg agtgcactaa actcaccatc     780
ctccttaacg acgtgctctc tctacaaaaa gaatttcgcg tgtctcagct tgagaacctt     840
gtccttcttt tcatgaacaa gtacgatctc cccttcaag cagccatcga taagatccta      900
gatctcatcc gcgagcacta tgcaatctgt gttgcggccg aggagaggct tccttggagc     960
aaagacgacg agaagctgaa caaggatatc agagaatatg ttcgtggctg ccagaggctg    1020
gctactggca ctgcttactg gagttactcg tgcgagcggt attttaagca aacgcaacta    1080
aatgataaat gggaggtcct tctggatcta tcctatgaa                            1119

<210> SEQ ID NO 16
<211> LENGTH: 1044
<212> TYPE: DNA
<213> ORGANISM: Nodulisporium

<400> SEQUENCE: 16
atgaacttca gcttcaaaat tactctcaag aagccgacat tcagcggact tcaaagcttc      60
tttcctagac acaagccttc aataagccag tcttcatcat cttcaacttc ttcaacctct     120
tcaatcaagc ttgagaccac gtcaacgcct caatgcatta caacattccc tgtttacgtt     180
caccgagacg aagctcaaat ttcccaaggt gccttggacg ctcggagcaa ctttcaacac     240
ctccttccag atgctgaata tcgacctcat tcagccgggc cacatggcaa tttctttgcc     300
```

```
atctgttggc cagacagcaa aatggaaagg gcaaaactag ccactgaaat catcgagacg      360
ttgtggctat atgatgacgt tatcgaggat ataccacaca cggggggcctt ggaagcacac     420 gccagcgtcc gcgactcatt ggtaggaaag cccgagaaaa cacagtccaa gggtcggatt     480
gctacccttt tcaaaacctt cggtgagcgc gtgagtcaga tggacaaaga cggggcgccg     540
cgtgtcattg gctctcttaa gtcgtacctt gacaattacg acagccaaaa gaccccattc     600
tccacgattg cggaatatac agagtttaga atagtaaacg ttggatttgg gattatggaa     660
agttttatgc agtggaccct tggtatccat ctggatgaag atgagacaga gctgtctcgg     720
gactattact cctcctgtgg gcgagttatg gggttgacca acgacttgta ttcatggaag     780
gtcgagcgga tagaacctgg tgatcgacaa tggaatgccg tgccaatcat catgaagcag     840
tacaacatac gcgagaagga tgctacagta ttcctcagag ggttgattat gtaccatgaa     900
caagagacac gccgacttgg tctagagctt ttaaggaaaa ccggggaatc gccgaagatg     960
atccagtatg tgggcgcgat gggactgatg ctgggtggaa attgttactg gagctcgact    1020
tgcccgcgct acaatccgga gccg                                            1044
```

<210> SEQ ID NO 17
<211> LENGTH: 939
<212> TYPE: DNA
<213> ORGANISM: Nodulisporium

<400> SEQUENCE: 17

```
atgtctttgg catcgtcgtt tggggattat cccagctcgc actgggcgcc actgatacac      60
cccctttctg agagggtcac gcgggaagtc gacagctact tcctgcagca ttggcctttc     120
cccgatgaga aatcgaggaa gaaattcgtc gcagctgggt tctcgcgtgt aacgtgcttc     180
tacttcccta aagctctcaa cgaccgaatt cattttgctt gtcgactact tacagtcctg     240
tttctcatcg atgacctcct tgagtacatg tctttggaag atgggaaagc atataatgaa     300
aagctcatcc ctatttcccg cggtgacgta ctgccggatc gatcagtccc cgtggaatac     360
atcacgtatg acttatggga aagcatgaga gcacatgacc gcgttatggc agatgacata     420
ctcgagcccg tattcacatt ccagagggca caaactgact ccgtgcgcct ggaggccatg     480
gacctaggaa aatatctcga atatcgagag aaagatgttg gcaaggcact acttggagcc     540
ttgatgagat tctccatggg ccttgtcgtg cctccagagg acctcgctat tgcaaggcag     600
attgatttta actgtgcaag gcacctttca gttctgaatg acatatggag ctttgaaaaa     660
gagctgctgg catccaagaa tgcacacgaa gaaggtggtg tgttgtgctc ggccgtatct     720
atcttagctg agcaggtcgg aatatcaatt gatggagcaa aacgtatact atactacctc     780
tgtcgtgaat gggagcatcg acacgagacg ctagttaagg agatgctcca ggtccgagac     840
acaccagcct taagatcata tgtcaagggg cttgagtacc agatgatcgg gaacgaggcg     900
tggagcagga ctacactgag gtatctggcc ccaacagat                             939
```

<210> SEQ ID NO 18
<211> LENGTH: 1251
<212> TYPE: DNA
<213> ORGANISM: Nodulisporium

<400> SEQUENCE: 18

```
atggcgaggc ccaagcgaat caccacgaca ctgctgagtc tcgcgcggcg gacgcagtca      60
aagatatcat ctatcctatt cccgtccccc ctgcccgcgg aagggagctc aggcgccgtc     120
```

```
gtccaatacg ctcccgagaa gaagcccggc gcacagcagg gtctctgcgg tgaggcgttg      180
gtcttagctt ctcagctcga cgggcaaaca ttccgcctcc cagacctgtg gaaggtctta      240
gcagactggc ctctggccgc caacccgcac gcggagcggc tcgagggtct cgtcaacagc      300
atactagagc gccacatcac cagcgagaag aagctcaggg ctctaaaaca ggctaacttt      360
gcccgtctca tctccctctg gtatcccgac gcagaatggc ccgagctgga ggcggcaaca      420
gcctactctg tgtggatctt cgtgtgggac gacgaagtcg acgccggtga tactgacgtg      480
tctctcgacg aggagctctc gagagcctat tacaagaaat ctctcagcac gatccaccgc      540
ctcttaggtt tagatgatgc tggcggagat gaccaggggg gctccgagga ggaggagaca      600
ttgcatccca acatggtcct gtttggcgat gcagcacgca gcctgcgcag ctcaacagac      660
aagatccagc gggagcgatt ctaccgcgag atggagaact tcatgatcca agtgggtgta      720
gagcacagtc accgcatgcg cggctccatc cccaccgtgg acaaatacat ggagatacgc      780
tccgggtctg ttggttgtgc gccccagatc gccataccg attttatgct aaagatccga      840
ctccccgagt ccatcatgga atctgcggcc atgaaagcgc tctggagaga gacggttgta      900
atatgtctta ttcttaacga tgtttactct gttcagaaag aaatagcgca agggtcattg      960
ttaaacctag tcccagtaat attcaagaac tgcattcctg aaaagcagaa cctcgatacg      1020
gtaacggcgg atgtcgaggt agcgctgcag ggaagcataa ggggtttcga ggacgcagcg      1080
gcgtccctcg gtcagatggt ggctgatgac gcgcaactag acaaggatgt ccagtctttc      1140
attagatggt gccgctactt catcaccggg gtccagcaat ggagtataga atcggctcgg      1200
tacggcatgg cggagtgttt gcaagaggat ggctcgctca gcatagtgct g               1251
```

<210> SEQ ID NO 19
<211> LENGTH: 24
<212> TYPE: DNA
<213> ORGANISM: Artificial Sequence
<220> FEATURE:
<223> OTHER INFORMATION: primer sequence

<400> SEQUENCE: 19
cagtccaaat caggcggtag caga                                              24

<210> SEQ ID NO 20
<211> LENGTH: 24
<212> TYPE: DNA
<213> ORGANISM: Artificial Sequence
<220> FEATURE:
<223> OTHER INFORMATION: primer sequence

<400> SEQUENCE: 20
tgagaaggat cggaatcgag tggt                                              24

<210> SEQ ID NO 21
<211> LENGTH: 24
<212> TYPE: DNA
<213> ORGANISM: Artificial Sequence
<220> FEATURE:
<223> OTHER INFORMATION: primer sequence

<400> SEQUENCE: 21
tgctcctcgt cgacagtttc aagt                                              24

<210> SEQ ID NO 22
<211> LENGTH: 24
<212> TYPE: DNA
<213> ORGANISM: Artificial Sequence

```
<220> FEATURE:
<223> OTHER INFORMATION: primer sequence

<400> SEQUENCE: 22
cttcatattg gttgtgctgg accc                                              24

<210> SEQ ID NO 23
<211> LENGTH: 24
<212> TYPE: DNA
<213> ORGANISM: Artificial Sequence
<220> FEATURE:
<223> OTHER INFORMATION: primer sequence

<400> SEQUENCE: 23
aacccgctcc tacactcgcc caat                                              24

<210> SEQ ID NO 24
<211> LENGTH: 24
<212> TYPE: DNA
<213> ORGANISM: Artificial Sequence
<220> FEATURE:
<223> OTHER INFORMATION: primer sequence

<400> SEQUENCE: 24
tcggtagccg agcagcctgc cttg                                              24

<210> SEQ ID NO 25
<211> LENGTH: 20
<212> TYPE: DNA
<213> ORGANISM: Artificial Sequence
<220> FEATURE:
<223> OTHER INFORMATION: primer sequence

<400> SEQUENCE: 25
tttccgaccc gccagacacc                                                   20

<210> SEQ ID NO 26
<211> LENGTH: 20
<212> TYPE: DNA
<213> ORGANISM: Artificial Sequence
<220> FEATURE:
<223> OTHER INFORMATION: primer sequence

<400> SEQUENCE: 26
ccggtcctgc gattcctcca                                                   20
```